(12) United States Patent
Bonutti et al.

(10) Patent No.: US 10,076,377 B2
(45) Date of Patent: Sep. 18, 2018

(54) FIXATION SYSTEMS AND METHODS

(71) Applicant: P Tech, LLC, Effingham, IL (US)

(72) Inventors: Peter M. Bonutti, Delray Beach, FL (US); Matthew J. Cremens, Effingham, IL (US)

(73) Assignee: P Tech, LLC, Effingham, IL (US)

( * ) Notice: Subject to any disclaimer, the term of this patent is extended or adjusted under 35 U.S.C. 154(b) by 373 days.

(21) Appl. No.: 13/831,826

(22) Filed: Mar. 15, 2013

(65) Prior Publication Data

US 2014/0194907 A1    Jul. 10, 2014

Related U.S. Application Data

(60) Provisional application No. 61/749,261, filed on Jan. 5, 2013.

(51) Int. Cl.
*A61B 17/04* (2006.01)
*A61B 17/68* (2006.01)
(Continued)

(52) U.S. Cl.
CPC ...... *A61B 17/8866* (2013.01); *A61B 17/0401* (2013.01); *A61B 17/12109* (2013.01);
(Continued)

(58) Field of Classification Search
CPC . A61B 17/7022; A61B 17/8861; A61B 17/82; A61B 17/842; A61B 17/58–17/88; A61B 17/0401; A61B 2017/0414; A61B 2017/0404; A61B 2017/0406; A61B 2017/0408; A61B 2017/044; A61B 2017/0446; A61B 2017/0448;
(Continued)

(56) References Cited

U.S. PATENT DOCUMENTS

| 319,296 | A | 6/1885 | Molesworth |
|---|---|---|---|
| 668,878 | A | 2/1901 | Jensen |

(Continued)

FOREIGN PATENT DOCUMENTS

| CA | 2641580 | 8/2007 |
|---|---|---|
| CA | 2680827 | 9/2008 |

(Continued)

OTHER PUBLICATIONS

Copending U.S. Appl. No. 11/932,907—RCE Response dated Sep. 15, 2011.
(Continued)

*Primary Examiner* — Christopher L Templeton
*Assistant Examiner* — George J Ulsh
(74) *Attorney, Agent, or Firm* — Senniger Powers LLP

(57) ABSTRACT

Embodiments may include fixation devices and methods for securing first and second body tissue portions. Fixation devices may include a base component, an insert component, and a flexible member. The base component may include a passage. The insert component may be positionable within at least a portion of the passage. The elongate member may be configured to be positioned through the first and second body tissue portions. The elongate member may be tensioned and pinched between the base component and insert component to secure the first and second portions.

34 Claims, 57 Drawing Sheets

(51) Int. Cl.
*A61B 17/88* (2006.01)
*A61F 2/08* (2006.01)
*A61B 17/12* (2006.01)
*A61B 17/74* (2006.01)
*A61B 17/80* (2006.01)
*A61B 17/00* (2006.01)

(52) U.S. Cl.
CPC ...... *A61B 17/12131* (2013.01); *A61B 17/683* (2013.01); *A61F 2/0805* (2013.01); *A61F 2/0811* (2013.01); *A61B 17/0487* (2013.01); *A61B 17/1219* (2013.01); *A61B 17/12168* (2013.01); *A61B 17/744* (2013.01); *A61B 17/80* (2013.01); *A61B 17/8872* (2013.01); *A61B 2017/00659* (2013.01); *A61B 2017/0404* (2013.01); *A61B 2017/0406* (2013.01); *A61B 2017/0411* (2013.01); *A61B 2017/0414* (2013.01); *A61B 2017/0417* (2013.01); *A61B 2017/0453* (2013.01); *A61B 2017/0496* (2013.01); *A61F 2002/0835* (2013.01); *A61F 2002/0852* (2013.01); *A61F 2002/0858* (2013.01); *A61F 2002/0882* (2013.01)

(58) Field of Classification Search
CPC ...... A61B 2017/045; A61B 2017/0458; A61B 17/0487; A61B 2017/0496; A61B 2017/0453; A61B 17/744; A61B 17/683; A61F 5/04; A61F 2002/0847; A61F 2002/0864; A61F 2002/087; A61F 2002/0882; A61F 2/0811
USPC .............................. 606/86 R, 232
See application file for complete search history.

(56) References Cited

U.S. PATENT DOCUMENTS

| | | |
|---|---|---|
| 668,879 A | 2/1901 | Miller |
| 702,789 A | 6/1902 | Gibson |
| 862,712 A | 8/1907 | Collins |
| 2,121,193 A | 12/1932 | Hanicke |
| 2,187,852 A | 8/1936 | Friddle |
| 2,178,840 A | 11/1939 | Lorenian |
| 2,199,025 A | 4/1940 | Conn |
| 2,235,419 A | 3/1941 | Callahan |
| 2,248,054 A | 7/1941 | Becker |
| 2,270,188 A | 1/1942 | Longfellow |
| 2,518,276 A | 8/1950 | Braward |
| 2,557,669 A | 6/1951 | Lloyd |
| 2,566,499 A | 9/1951 | Richter |
| 2,621,653 A | 12/1952 | Briggs |
| 2,725,053 A | 11/1955 | Bambara |
| 2,830,587 A | 4/1958 | Everett |
| 3,204,635 A | 9/1965 | Voss et al. |
| 3,311,110 A * | 3/1967 | Singerman ....... A61B 17/06004 29/510 |
| 3,347,234 A | 10/1967 | Voss |
| 3,367,809 A | 2/1968 | Soloff |
| 3,391,690 A | 7/1968 | Armao |
| 3,477,429 A | 11/1969 | Sampson |
| 3,513,848 A | 5/1970 | Winston et al. |
| 3,518,993 A | 7/1970 | Blake |
| 3,577,991 A | 5/1971 | Wilkinson |
| 3,596,292 A | 8/1971 | Erb et al. |
| 3,608,539 A | 9/1971 | Miller |
| 3,625,220 A | 12/1971 | Engelsher |
| 3,648,705 A | 3/1972 | Lary |
| 3,653,388 A | 4/1972 | Tenckhoff |
| 3,656,476 A | 4/1972 | Swinney |
| 3,657,056 A | 4/1972 | Winston et al. |
| 3,678,980 A | 7/1972 | Gutshall |
| 3,709,218 A | 1/1973 | Halloran |
| 3,711,347 A | 1/1973 | Wagner et al. |
| 3,760,808 A | 9/1973 | Bleuer |
| 3,788,318 A | 1/1974 | Kim et al. |
| 3,789,852 A | 2/1974 | Kim et al. |
| 3,802,438 A | 4/1974 | Wolvek |
| 3,807,394 A | 4/1974 | Attenborough |
| 3,809,075 A | 5/1974 | Matles |
| 3,811,449 A | 5/1974 | Gravlee et al. |
| 3,825,010 A | 7/1974 | McDonald |
| 3,833,003 A | 9/1974 | Taricco |
| 3,835,849 A | 9/1974 | McGuire |
| 3,842,824 A | 10/1974 | Neufeld |
| 3,857,396 A | 12/1974 | Hardwick |
| 3,867,932 A | 2/1975 | Huene |
| 3,875,652 A | 4/1975 | Arnold |
| 3,898,992 A | 8/1975 | Balamuth |
| 3,918,442 A | 11/1975 | Nikolaev et al. |
| 3,968,800 A | 7/1976 | Vilasi |
| 4,023,559 A | 5/1977 | Gaskell |
| 4,064,566 A | 12/1977 | Fletcher et al. |
| 4,089,071 A | 5/1978 | Kainberz et al. |
| 4,156,574 A | 5/1979 | Boben |
| 4,164,794 A | 8/1979 | Spector et al. |
| 4,171,544 A | 10/1979 | Hench et al. |
| 4,183,102 A | 1/1980 | Guiset |
| 4,199,864 A | 4/1980 | Ashman |
| 4,200,939 A | 5/1980 | Oser |
| 4,210,148 A | 7/1980 | Stivala |
| 4,213,816 A | 7/1980 | Morris |
| 4,235,233 A | 11/1980 | Mouwen |
| 4,235,238 A | 11/1980 | Ogiu et al. |
| 4,257,411 A | 3/1981 | Cho |
| 4,265,231 A | 5/1981 | Scheller, Jr. et al. |
| 4,281,649 A | 8/1981 | Derweduwen |
| 4,291,698 A | 9/1981 | Fuchs |
| 4,309,488 A | 1/1982 | Heide et al. |
| 4,320,762 A | 3/1982 | Bentov |
| 4,351,069 A | 9/1982 | Ballintyn et al. |
| 4,364,381 A | 12/1982 | Sher et al. |
| 4,365,356 A | 12/1982 | Broemer et al. |
| 4,388,921 A | 6/1983 | Sutter et al. |
| 4,395,798 A | 8/1983 | McVey |
| 4,409,974 A | 10/1983 | Freedland |
| 4,414,166 A | 11/1983 | Charlson et al. |
| 4,437,191 A | 3/1984 | Van der Zat et al. |
| 4,437,362 A | 3/1984 | Hurst |
| 4,444,180 A | 4/1984 | Schneider et al. |
| 4,448,194 A | 5/1984 | DiGiovanni et al. |
| 4,456,005 A | 6/1984 | Lichty |
| 4,461,281 A | 7/1984 | Carson |
| 4,484,570 A * | 11/1984 | Sutter et al. ............ 606/282 |
| 4,493,317 A | 1/1985 | Klaue |
| 4,495,664 A | 1/1985 | Bianquaert |
| 4,501,031 A | 2/1985 | McDaniel et al. |
| 4,504,268 A | 3/1985 | Herlitze |
| 4,506,681 A | 3/1985 | Mundell |
| 4,514,125 A | 4/1985 | Stol |
| 4,526,173 A | 7/1985 | Sheehan |
| 4,532,926 A | 8/1985 | O'Holla |
| 4,535,772 A | 8/1985 | Sheehan |
| 4,547,327 A | 10/1985 | Bruins et al. |
| 4,556,350 A | 12/1985 | Bernhardt et al. |
| 4,566,138 A | 1/1986 | Lewis et al. |
| 4,589,868 A | 5/1986 | Dretler |
| 4,590,928 A | 5/1986 | Hunt et al. |
| 4,597,379 A | 7/1986 | Kihn et al. |
| 4,599,085 A | 7/1986 | Riess et al. |
| 4,601,893 A | 7/1986 | Cardinal |
| 4,606,335 A | 8/1986 | Wedeen |
| 4,621,640 A | 11/1986 | Mulhollan et al. |
| 4,630,609 A | 12/1986 | Chin |
| 4,632,100 A | 12/1986 | Somers |
| 4,632,101 A | 12/1986 | Freedland |
| 4,645,503 A | 2/1987 | Lin et al. |
| 4,657,460 A | 4/1987 | Bien |
| 4,659,268 A | 4/1987 | Del Mundo et al. |
| 4,662,063 A | 5/1987 | Collins et al. |
| 4,662,068 A | 5/1987 | Polonsky |
| 4,662,887 A | 5/1987 | Turner et al. |
| 4,669,473 A | 6/1987 | Richards et al. |

(56) References Cited

U.S. PATENT DOCUMENTS

| | | |
|---|---|---|
| 4,685,458 A | 8/1987 | Leckrone |
| 4,691,741 A | 9/1987 | Affa |
| 4,705,040 A | 11/1987 | Mueller et al. |
| 4,706,670 A | 11/1987 | Andersen et al. |
| 4,708,139 A | 11/1987 | Dunbar, IV |
| 4,713,077 A | 12/1987 | Small |
| 4,716,901 A | 1/1988 | Jackson et al. |
| 4,718,909 A | 1/1988 | Brown |
| 4,722,331 A | 2/1988 | Fox |
| 4,722,948 A | 2/1988 | Sanderson |
| 4,724,584 A | 2/1988 | Kasai |
| 4,738,255 A | 4/1988 | Goble et al. |
| 4,739,751 A | 4/1988 | Sapega et al. |
| 4,741,330 A | 5/1988 | Hayhurst |
| 4,743,257 A | 5/1988 | Tormala |
| 4,749,585 A | 6/1988 | Greco et al. |
| 4,750,492 A | 6/1988 | Jacobs |
| 4,768,507 A | 9/1988 | Fischell |
| 4,772,286 A | 9/1988 | Goble et al. |
| 4,776,328 A | 10/1988 | Frey et al. |
| 4,776,738 A | 10/1988 | Winston |
| 4,776,851 A | 10/1988 | Bruchman et al. |
| 4,781,182 A | 11/1988 | Purnell et al. |
| 4,790,303 A | 12/1988 | Steffee |
| 4,792,336 A | 12/1988 | Hiavacek et al. |
| 4,817,591 A | 4/1989 | Klause |
| 4,822,224 A | 4/1989 | Carl et al. |
| 4,823,794 A | 4/1989 | Pierce |
| 4,832,025 A | 5/1989 | Coates |
| 4,832,026 A | 5/1989 | Jones |
| 4,834,752 A | 5/1989 | Van Kampen |
| 4,841,960 A | 6/1989 | Garner |
| 4,843,112 A | 6/1989 | Gerhart |
| 4,846,812 A | 7/1989 | Walker et al. |
| 4,862,882 A | 9/1989 | Venturi et al. |
| 4,869,242 A | 9/1989 | Galluzzo |
| 4,870,957 A | 10/1989 | Goble et al. |
| 4,883,048 A | 11/1989 | Purnell et al. |
| 4,890,612 A | 1/1990 | Kensey |
| 4,895,148 A | 1/1990 | Bays et al. |
| 4,898,156 A | 2/1990 | Gatturna et al. |
| 4,899,729 A | 2/1990 | Gill et al. |
| 4,899,744 A | 2/1990 | Fujitsuka et al. |
| 4,901,721 A | 2/1990 | Hakki |
| 4,921,479 A | 5/1990 | Grayzel |
| 4,922,897 A | 5/1990 | Sapega et al. |
| 4,924,866 A | 5/1990 | Yoon |
| 4,932,960 A | 6/1990 | Green et al. |
| 4,935,026 A | 6/1990 | Drews |
| 4,935,028 A | 6/1990 | Drews |
| 4,945,625 A | 8/1990 | Winston |
| 4,946,468 A | 8/1990 | Li |
| 4,950,285 A | 8/1990 | Wilk |
| 4,954,126 A | 9/1990 | Wallsten |
| 4,955,910 A | 9/1990 | Bolesky |
| 4,957,498 A | 9/1990 | Caspari et al. |
| 4,961,741 A | 10/1990 | Hayhurst |
| 4,963,151 A | 10/1990 | Ducheyne et al. |
| 4,966,583 A | 10/1990 | Debbas |
| 4,968,315 A | 11/1990 | Gatturna |
| 4,968,317 A | 11/1990 | Tormala |
| 4,969,888 A | 11/1990 | Scholten et al. |
| 4,969,892 A | 11/1990 | Burton et al. |
| 4,990,161 A | 2/1991 | Kampner |
| 4,994,071 A | 2/1991 | MacGregor |
| 4,997,445 A | 3/1991 | Hodorek |
| 4,998,539 A | 3/1991 | Delsanti |
| 5,002,550 A | 3/1991 | Li |
| 5,002,563 A | 3/1991 | Pyka et al. |
| 5,009,652 A | 4/1991 | Morgan et al. |
| 5,009,663 A | 4/1991 | Broome |
| 5,009,664 A | 4/1991 | Sievers |
| 5,013,316 A | 5/1991 | Goble et al. |
| 5,019,090 A | 5/1991 | Pinchuk |
| 5,021,059 A | 6/1991 | Kensey et al. |
| 5,035,713 A | 7/1991 | Friis |
| 5,037,404 A | 8/1991 | Gold et al. |
| 5,037,422 A | 8/1991 | Hayhurst et al. |
| 5,041,093 A | 8/1991 | Chu |
| 5,041,114 A | 8/1991 | Chapman et al. |
| 5,041,129 A | 8/1991 | Hayhurst et al. |
| 5,046,513 A | 9/1991 | Gatturna et al. |
| 5,047,055 A | 9/1991 | Bao et al. |
| 5,051,049 A | 9/1991 | Wills |
| 5,053,046 A | 10/1991 | Janese |
| 5,053,047 A | 10/1991 | Yoon |
| 5,059,193 A | 10/1991 | Kuslich |
| 5,059,206 A | 10/1991 | Winters |
| 5,061,274 A | 10/1991 | Kensey |
| 5,061,286 A | 10/1991 | Lyle |
| 5,064,286 A | 10/1991 | Lyle |
| 5,069,674 A | 12/1991 | Fearnot et al. |
| 5,078,731 A | 1/1992 | Hayhurst |
| 5,078,744 A | 1/1992 | Chvapil |
| 5,078,745 A | 1/1992 | Rhenter et al. |
| 5,084,050 A | 1/1992 | Draenert |
| 5,084,051 A | 1/1992 | Tormala et al. |
| 5,085,660 A | 2/1992 | Lin |
| 5,085,661 A | 2/1992 | Moss |
| 5,098,433 A | 3/1992 | Freedland |
| 5,098,434 A | 3/1992 | Serbousek |
| 5,098,436 A | 3/1992 | Ferrante et al. |
| 5,100,405 A | 3/1992 | McLaren |
| 5,100,417 A | 3/1992 | Cerier et al. |
| 5,102,417 A | 4/1992 | Palmaz |
| 5,102,421 A | 4/1992 | Anspach, Jr. |
| 5,108,399 A | 4/1992 | Eitenmuller et al. |
| 5,120,175 A | 6/1992 | Arbegast et al. |
| 5,123,520 A | 6/1992 | Schmid et al. |
| 5,123,914 A | 6/1992 | Cope |
| 5,123,941 A | 6/1992 | Lauren et al. |
| 5,133,732 A | 7/1992 | Wiktor |
| RE34,021 E | 8/1992 | Mueller |
| 5,141,520 A | 8/1992 | Goble et al. |
| 5,147,362 A | 9/1992 | Goble |
| 5,154,720 A | 10/1992 | Trott et al. |
| 5,156,613 A | 10/1992 | Sawyer |
| 5,156,616 A | 10/1992 | Meadows et al. |
| 5,158,566 A | 10/1992 | Pianetti |
| 5,158,934 A | 10/1992 | Ammann et al. |
| 5,163,960 A | 11/1992 | Bonutti |
| 5,171,251 A | 12/1992 | Bregen et al. |
| 5,176,682 A | 1/1993 | Chow |
| 5,179,964 A | 1/1993 | Cook |
| 5,180,385 A | 1/1993 | Sontag |
| 5,180,388 A | 1/1993 | DiCarlo |
| 5,183,464 A | 2/1993 | Dubrul et al. |
| 5,192,287 A | 3/1993 | Fournier et al. |
| 5,192,326 A | 3/1993 | Bao et al. |
| 5,197,166 A | 3/1993 | Meier et al. |
| 5,197,971 A | 3/1993 | Bonutti |
| 5,203,784 A | 4/1993 | Ross et al. |
| 5,203,787 A | 4/1993 | Noblitt |
| 5,208,950 A | 5/1993 | Merritt |
| 5,209,776 A | 5/1993 | Bass et al. |
| 5,217,493 A | 6/1993 | Raad et al. |
| 5,219,359 A | 6/1993 | McQuilkin et al. |
| 5,226,899 A | 7/1993 | Lee et al. |
| 5,234,006 A | 8/1993 | Eaton et al. |
| 5,234,425 A | 8/1993 | Fogarty et al. |
| 5,234,443 A | 8/1993 | Phan |
| 5,236,438 A | 8/1993 | Wilk |
| 5,236,445 A | 8/1993 | Hayhurst |
| 5,242,902 A | 9/1993 | Murphy et al. |
| 5,254,113 A | 10/1993 | Wilk |
| 5,258,007 A | 11/1993 | Spetzler et al. |
| 5,258,015 A | 11/1993 | Li et al. |
| 5,258,016 A | 11/1993 | DiPoto et al. |
| 5,261,886 A | 11/1993 | Chesterfield |
| 5,266,325 A | 11/1993 | Kuzma et al. |
| 5,269,783 A | 12/1993 | Sander |
| 5,269,785 A | 12/1993 | Bonutti |
| 5,269,809 A | 12/1993 | Hayhurst et al. |
| 5,281,235 A | 1/1994 | Haber et al. |

(56) References Cited

U.S. PATENT DOCUMENTS

| | | |
|---|---|---|
| 5,282,832 A | 2/1994 | Toso et al. |
| 5,290,281 A | 3/1994 | Tschakaloff |
| 5,304,119 A | 4/1994 | Balaban et al. |
| 5,306,280 A | 4/1994 | Bregen et al. |
| 5,306,301 A | 4/1994 | Graf et al. |
| 5,315,741 A | 5/1994 | Dubberke |
| 5,318,588 A | 6/1994 | Horzewski et al. |
| 5,320,611 A | 6/1994 | Bonutti et al. |
| 5,324,308 A | 6/1994 | Pierce |
| 5,328,480 A | 7/1994 | Melker et al. |
| 5,329,846 A | 7/1994 | Bonutti |
| 5,329,924 A | 7/1994 | Bonutti |
| 5,330,468 A | 7/1994 | Burkhart |
| 5,330,476 A | 7/1994 | Hiot et al. |
| 5,330,486 A | 7/1994 | Wilk |
| 5,336,231 A | 8/1994 | Adair |
| 5,336,240 A | 8/1994 | Metzler et al. |
| 5,339,799 A | 8/1994 | Kami et al. |
| 5,349,956 A | 9/1994 | Bonutti |
| 5,352,229 A | 10/1994 | Goble et al. |
| 5,354,298 A | 10/1994 | Lee et al. |
| 5,354,302 A | 10/1994 | Ko |
| 5,366,480 A | 11/1994 | Corriveaau et al. |
| 5,370,646 A | 12/1994 | Reese et al. |
| 5,370,660 A | 12/1994 | Weinstein et al. |
| 5,372,146 A | 12/1994 | Branch |
| 5,374,235 A | 12/1994 | Ahrens |
| 5,376,126 A | 12/1994 | Lin |
| 5,382,254 A | 1/1995 | McGarry et al. |
| 5,383,883 A | 1/1995 | Wilk et al. |
| 5,383,905 A | 1/1995 | Golds et al. |
| 5,391,173 A | 2/1995 | Wilk |
| 5,395,308 A | 3/1995 | Fox et al. |
| 5,397,311 A | 3/1995 | Walker et al. |
| 5,400,805 A | 3/1995 | Warren |
| 5,403,312 A | 4/1995 | Yates et al. |
| 5,403,348 A | 4/1995 | Bonutti |
| 5,405,359 A | 4/1995 | Pierce |
| 5,411,523 A | 5/1995 | Goble |
| 5,413,585 A | 5/1995 | Pagedas |
| 5,417,691 A | 5/1995 | Hayhurst |
| 5,417,701 A | 5/1995 | Holmes |
| 5,417,712 A | 5/1995 | Whittaker et al. |
| 5,423,796 A | 6/1995 | Shikhman et al. |
| 5,431,670 A | 7/1995 | Holmes |
| 5,439,470 A | 8/1995 | Li |
| 5,441,538 A | 8/1995 | Bonutti |
| 5,443,512 A | 8/1995 | Parr et al. |
| 5,447,503 A | 9/1995 | Miller |
| 5,449,372 A | 9/1995 | Schmaltz et al. |
| 5,449,382 A | 9/1995 | Dayton |
| 5,451,235 A | 9/1995 | Lock |
| 5,453,090 A | 9/1995 | Martinez et al. |
| 5,456,722 A | 10/1995 | McLeod et al. |
| 5,458,653 A | 10/1995 | Davison |
| 5,462,561 A | 10/1995 | Voda |
| 5,464,424 A | 11/1995 | O'Don |
| 5,464,426 A | 11/1995 | Bonutti |
| 5,464,427 A | 11/1995 | Curtis et al. |
| 5,470,337 A | 11/1995 | Moss |
| 5,472,444 A | 12/1995 | Huebner et al. |
| 5,474,554 A | 12/1995 | Ku |
| 5,478,351 A | 12/1995 | Meade et al. |
| 5,478,353 A | 12/1995 | Yoon |
| 5,480,403 A | 1/1996 | Lee et al. |
| 5,486,197 A | 1/1996 | Le et al. |
| 5,487,844 A | 1/1996 | Fujita |
| 5,488,958 A | 2/1996 | Topel et al. |
| 5,496,292 A | 3/1996 | Burnham |
| 5,496,318 A | 3/1996 | Howland |
| 5,496,335 A | 3/1996 | Thomason et al. |
| 5,496,348 A | 3/1996 | Bonutti |
| 5,500,000 A | 3/1996 | Feagin et al. |
| 5,501,700 A | 3/1996 | Hirata |
| 5,504,977 A | 4/1996 | Weppner |
| 5,505,735 A | 4/1996 | Li |
| 5,507,754 A | 4/1996 | Green et al. |
| 5,522,844 A | 6/1996 | Johnson |
| 5,522,845 A | 6/1996 | Wenstrom, Jr. |
| 5,522,846 A | 6/1996 | Bonutti |
| 5,527,341 A | 6/1996 | Gogolewski et al. |
| 5,527,342 A | 6/1996 | Pietrzak et al. |
| 5,527,343 A | 6/1996 | Bonutti |
| 5,529,075 A | 6/1996 | Clark |
| 5,531,759 A | 7/1996 | Kensey et al. |
| 5,534,012 A | 7/1996 | Bonutti |
| 5,534,028 A | 7/1996 | Bao et al. |
| 5,540,718 A | 7/1996 | Bartlett |
| 5,542,423 A | 8/1996 | Bonutti |
| 5,545,178 A | 8/1996 | Kensey et al. |
| 5,545,180 A | 8/1996 | Le et al. |
| 5,545,206 A | 8/1996 | Carson |
| 5,549,630 A | 8/1996 | Bonutti |
| 5,549,631 A | 8/1996 | Bonutti |
| 5,556,402 A | 9/1996 | Xu |
| 5,569,252 A | 10/1996 | Justin et al. |
| 5,569,305 A | 10/1996 | Bonutti |
| 5,569,306 A | 10/1996 | Thal |
| 5,573,517 A | 11/1996 | Bonutti et al. |
| 5,573,538 A | 11/1996 | Laboureau |
| 5,573,542 A | 11/1996 | Stevens |
| 5,575,801 A | 11/1996 | Habermeyer |
| 5,578,046 A | 11/1996 | Liu |
| 5,580,344 A | 12/1996 | Hasson |
| 5,584,835 A | 12/1996 | Greenfield |
| 5,584,839 A | 12/1996 | Gieringer |
| 5,584,860 A | 12/1996 | Goble et al. |
| 5,584,862 A | 12/1996 | Bonutti |
| 5,591,206 A | 1/1997 | Moufarrege |
| 5,593,422 A | 1/1997 | Muijs Van De Moer et al. |
| 5,593,425 A | 1/1997 | Bonutti et al. |
| 5,593,625 A | 1/1997 | Riebel et al. |
| 5,601,557 A | 2/1997 | Hayhurst |
| 5,601,558 A | 2/1997 | Torrie et al. |
| 5,601,595 A | 2/1997 | Schwartz |
| 5,607,427 A | 3/1997 | Tschakaloff |
| 5,609,595 A | 3/1997 | Pennig |
| 5,618,314 A | 4/1997 | Harwin et al. |
| 5,620,461 A | 4/1997 | Muijs Van De Moer et al. |
| 5,626,612 A | 5/1997 | Bartlett |
| 5,626,614 A | 5/1997 | Hart |
| 5,626,718 A | 5/1997 | Philippe et al. |
| 5,630,824 A | 5/1997 | Hart |
| 5,634,926 A | 6/1997 | Jobe |
| 5,628,751 A | 7/1997 | Sander et al. |
| 5,643,274 A | 7/1997 | Sander et al. |
| 5,643,293 A | 7/1997 | Kogasaka et al. |
| 5,643,295 A | 7/1997 | Yoon |
| 5,643,321 A | 7/1997 | McDevitt |
| 5,645,553 A | 7/1997 | Kolesa et al. |
| 5,645,597 A | 7/1997 | Krapiva |
| 5,645,599 A | 7/1997 | Samani |
| 5,649,955 A | 7/1997 | Hashimoto et al. |
| 5,649,963 A | 7/1997 | McDevitt |
| 5,651,377 A | 7/1997 | O'Donnell, Jr. |
| 5,658,313 A | 8/1997 | Thal |
| 5,660,225 A | 8/1997 | Saffran |
| 5,662,658 A | 9/1997 | Wenstrom, Jr. |
| 5,665,089 A | 9/1997 | Dall et al. |
| 5,665,109 A | 9/1997 | Yoon |
| 5,667,513 A | 9/1997 | Torrie et al. |
| 5,669,917 A | 9/1997 | Sauer et al. |
| 5,674,240 A | 10/1997 | Bonutti |
| 5,681,310 A | 10/1997 | Yuan et al. |
| 5,681,333 A | 10/1997 | Burkhart et al. |
| 5,681,351 A | 10/1997 | Jamiolkowski et al. |
| 5,681,352 A | 10/1997 | Clancy, III et al. |
| 5,685,820 A | 11/1997 | Riek et al. |
| 5,688,283 A | 11/1997 | Knapp |
| 5,690,654 A | 11/1997 | Ovil |
| 5,690,655 A | 11/1997 | Hart et al. |
| 5,690,676 A | 11/1997 | DiPoto et al. |
| 5,693,055 A | 12/1997 | Zahiri et al. |
| 5,697,950 A | 12/1997 | Fucci et al. |

(56) References Cited

U.S. PATENT DOCUMENTS

| | | |
|---|---|---|
| 5,702,397 A | 12/1997 | Gonle et al. |
| 5,702,462 A | 12/1997 | Oberlander |
| 5,707,395 A | 1/1998 | Li |
| 5,713,903 A | 2/1998 | Sander et al. |
| 5,713,921 A | 2/1998 | Bonutti |
| 5,718,717 A | 2/1998 | Bonutti |
| 5,720,747 A | 2/1998 | Burke |
| 5,725,541 A | 3/1998 | Anspach, III et al. |
| 5,725,556 A | 3/1998 | Moser et al. |
| 5,725,582 A | 3/1998 | Bevan |
| 5,730,747 A | 3/1998 | Ek et al. |
| 5,733,306 A | 3/1998 | Bonutti |
| 5,720,753 A | 4/1998 | Sander et al. |
| 5,735,875 A | 4/1998 | Bonutti et al. |
| 5,735,877 A | 4/1998 | Pagedas |
| 5,735,899 A | 4/1998 | Schwartz et al. |
| 5,741,282 A | 4/1998 | Anspach, III et al. |
| 5,752,952 A | 5/1998 | Adamson |
| 5,752,974 A | 5/1998 | Rhee et al. |
| 5,755,809 A | 5/1998 | Cohen et al. |
| 5,762,458 A | 6/1998 | Wang et al. |
| 5,766,221 A | 6/1998 | Benderev et al. |
| 5,769,894 A | 6/1998 | Ferragamo |
| 5,772,672 A | 6/1998 | Toy et al. |
| 5,776,151 A | 7/1998 | Chan |
| 5,779,706 A | 7/1998 | Tschakaloff |
| 5,782,862 A | 7/1998 | Bonutti |
| 5,785,713 A | 7/1998 | Jobe |
| 5,792,096 A | 8/1998 | Rentmeester et al. |
| 5,797,931 A | 8/1998 | Bito et al. |
| 5,800,537 A | 9/1998 | Bell |
| 5,807,403 A | 9/1998 | Beyar et al. |
| 5,810,849 A | 9/1998 | Kontos |
| 5,810,853 A | 9/1998 | Yoon |
| 5,810,884 A | 9/1998 | Kim |
| 5,814,072 A | 9/1998 | Bonutti |
| 5,814,073 A | 9/1998 | Bonutti |
| 5,817,107 A | 10/1998 | Schaller |
| 5,823,994 A | 10/1998 | Sharkey et al. |
| 5,824,009 A | 10/1998 | Fukuda et al. |
| 5,830,125 A | 11/1998 | Scribner et al. |
| 5,836,897 A | 11/1998 | Sakural et al. |
| 5,839,899 A | 11/1998 | Robinson |
| 5,843,084 A | 12/1998 | Hart |
| 5,843,178 A | 12/1998 | Vanney et al. |
| 5,845,645 A | 12/1998 | Bonutti |
| 5,851,185 A | 12/1998 | Berns |
| 5,865,834 A | 2/1999 | McGuire |
| 5,866,634 A | 2/1999 | Tokushige |
| 5,868,749 A | 2/1999 | Reed |
| 5,874,235 A | 2/1999 | Chan |
| 5,879,372 A | 3/1999 | Bartlett |
| 5,891,166 A | 4/1999 | Schervinsky |
| 5,891,168 A | 4/1999 | Thal |
| 5,893,880 A | 4/1999 | Egan et al. |
| 5,897,574 A | 4/1999 | Bonutti |
| 5,899,911 A | 5/1999 | Carter |
| 5,899,921 A | 5/1999 | Caspari et al. |
| 5,906,579 A | 5/1999 | Vander Salm et al. |
| 5,906,625 A | 5/1999 | Bito et al. |
| 5,908,429 A | 6/1999 | Yoon |
| 5,911,721 A | 6/1999 | Nicholson et al. |
| 5,918,604 A | 7/1999 | Whelan |
| 5,919,193 A | 7/1999 | Slavitt |
| 5,919,194 A | 7/1999 | Anderson |
| 5,919,208 A | 7/1999 | Valenti |
| 5,919,215 A | 7/1999 | Wiklund et al. |
| 5,921,986 A | 7/1999 | Bonutti |
| 5,925,064 A | 7/1999 | Meyers et al. |
| 5,928,244 A | 7/1999 | Tovey et al. |
| 5,928,267 A | 7/1999 | Bonutti et al. |
| 5,931,838 A | 8/1999 | Vito |
| 5,931,869 A | 8/1999 | Boucher et al. |
| 5,940,942 A | 8/1999 | Fong |
| 5,941,900 A | 8/1999 | Bonutti |
| 5,941,901 A | 8/1999 | Egan |
| 5,944,750 A | 8/1999 | Tanner |
| 5,945,002 A | 9/1999 | Bonutti |
| 5,947,982 A | 9/1999 | Duran |
| 5,948,000 A | 9/1999 | Larsen et al. |
| 5,948,001 A | 9/1999 | Larsen |
| 5,951,590 A | 9/1999 | Goldfarb |
| 5,957,953 A | 9/1999 | DiPoto et al. |
| 5,961,499 A | 10/1999 | Bonutti |
| 5,961,521 A | 10/1999 | Roger |
| 5,961,554 A | 10/1999 | Janson et al. |
| 5,964,765 A | 10/1999 | Fenton, Jr. et al. |
| 5,964,769 A | 10/1999 | Wagner et al. |
| 5,968,046 A | 10/1999 | Castleman |
| 5,968,047 A | 10/1999 | Reed |
| 5,948,002 A | 11/1999 | Bonutti |
| 5,980,520 A | 11/1999 | Vancaillie |
| 5,980,559 A | 11/1999 | Bonutti |
| 5,984,929 A | 11/1999 | Bashiri et al. |
| 5,989,282 A | 11/1999 | Bonutti |
| 5,993,458 A | 11/1999 | Vaitekunas et al. |
| 5,993,477 A | 11/1999 | Vaitekunas et al. |
| 6,007,567 A | 12/1999 | Bonutti |
| 6,007,580 A | 12/1999 | Lehto et al. |
| 6,010,525 A | 1/2000 | Bonutti et al. |
| 6,010,526 A | 1/2000 | Sandstrom et al. |
| 6,017,321 A | 1/2000 | Boone |
| 6,033,429 A | 3/2000 | Magovern |
| 6,033,430 A | 3/2000 | Bonutti |
| 6,045,551 A | 4/2000 | Bonutti |
| 6,050,998 A | 4/2000 | Fletcher et al. |
| 6,056,751 A | 5/2000 | Fenton, Jr. |
| 6,056,772 A | 5/2000 | Bonutti |
| 6,056,773 A | 5/2000 | Bonutti |
| 6,059,797 A | 5/2000 | Mears |
| 6,059,817 A | 5/2000 | Bonutti et al. |
| 6,059,827 A | 5/2000 | Fenton |
| 6,063,095 A | 5/2000 | Wang et al. |
| 6,066,151 A | 5/2000 | Miyawaki et al. |
| 6,066,160 A | 5/2000 | Colvin et al. |
| 6,066,166 A | 5/2000 | Bischoff et al. |
| 6,068,637 A | 5/2000 | Popov et al. |
| 6,068,648 A | 5/2000 | Cole |
| 6,077,277 A | 6/2000 | Mollenauer et al. |
| 6,077,292 A | 6/2000 | Bonutti |
| 6,080,161 A | 6/2000 | Eaves, III et al. |
| 6,083,522 A | 7/2000 | Chu et al. |
| 6,086,593 A | 7/2000 | Bonutti |
| 6,086,608 A | 7/2000 | Ek et al. |
| 6,090,072 A | 7/2000 | Kratoska et al. |
| 6,099,531 A | 8/2000 | Bonutti |
| 6,099,537 A | 8/2000 | Sugai et al. |
| 6,099,550 A | 8/2000 | Yoon |
| 6,099,552 A | 8/2000 | Adams |
| 6,102,850 A | 8/2000 | Wang et al. |
| 6,106,545 A | 8/2000 | Egan |
| 6,117,160 A | 9/2000 | Bonutti |
| 6,120,536 A | 9/2000 | Ding et al. |
| 6,125,574 A | 10/2000 | Ganaja et al. |
| 6,126,677 A | 10/2000 | Ganaja et al. |
| 6,139,320 A | 10/2000 | Hahn |
| RE36,974 E | 11/2000 | Bonutti |
| 6,149,669 A | 11/2000 | Li |
| 6,152,949 A | 11/2000 | Bonutti |
| 6,155,756 A | 12/2000 | Mericle et al. |
| 6,159,224 A | 12/2000 | Yoon |
| 6,159,234 A | 12/2000 | Bonutti et al. |
| 6,171,299 B1 | 1/2001 | Bonutti |
| 6,171,307 B1 | 1/2001 | Bonutti |
| 6,174,324 B1 | 1/2001 | Egan et al. |
| 6,179,840 B1 | 1/2001 | Bowman |
| 6,179,850 B1 | 1/2001 | Goradia |
| 6,187,008 B1 | 2/2001 | Hamman |
| 6,190,400 B1 | 2/2001 | Van De Moer et al. |
| 6,190,401 B1 | 2/2001 | Green |
| 6,200,322 B1 | 3/2001 | Branch et al. |
| 6,217,591 B1 | 4/2001 | Egan et al. |
| 6,224,593 B1 | 5/2001 | Ryan |
| 6,224,630 B1 | 5/2001 | Bao et al. |

(56) References Cited

U.S. PATENT DOCUMENTS

| | | |
|---|---|---|
| 6,228,086 B1 | 5/2001 | Wahl et al. |
| 6,231,592 B1 | 5/2001 | Bonutti et al. |
| 6,238,395 B1 | 5/2001 | Bonutti |
| 6,238,396 B1 | 5/2001 | Bonutti |
| 6,258,091 B1 | 7/2001 | Sevrain et al. |
| 6,264,675 B1 | 7/2001 | Brotz |
| 6,267,761 B1 | 7/2001 | Ryan |
| 6,273,717 B1 | 8/2001 | Hahn et al. |
| 6,280,474 B1 | 8/2001 | Cassidy et al. |
| 6,286,746 B1 | 9/2001 | Egan et al. |
| 6,287,325 B1 | 9/2001 | Bonutti |
| 6,293,961 B2 | 9/2001 | Schwartz et al. |
| 6,306,159 B1 | 10/2001 | Schwartz et al. |
| 6,309,405 B1 | 10/2001 | Bonutti |
| 6,312,448 B1 | 11/2001 | Bonutti |
| 6,338,730 B1 | 1/2002 | Bonutti et al. |
| 6,340,365 B2 | 1/2002 | Dittrich et al. |
| 6,348,056 B1 | 2/2002 | Bates et al. |
| 6,358,271 B1 | 3/2002 | Egan et al. |
| 6,364,897 B1 | 4/2002 | Bonutti |
| 6,368,325 B1 | 4/2002 | McKinley et al. |
| 6,368,343 B1 | 4/2002 | Bonutti et al. |
| 6,371,957 B1 | 4/2002 | Amrein et al. |
| 6,409,742 B1 | 6/2002 | Fulton, III |
| 6,409,743 B1 | 6/2002 | Fenton, Jr. |
| 6,419,704 B1 | 7/2002 | Ferree |
| 6,423,088 B1 | 7/2002 | Fenton |
| 6,425,919 B1 | 7/2002 | Lambrecht |
| 6,428,562 B2 | 8/2002 | Bonutti |
| 6,432,115 B1 | 8/2002 | Mollenauer et al. |
| 6,447,516 B1 | 9/2002 | Bonutti |
| 6,450,985 B1 | 9/2002 | Schoelling et al. |
| 6,461,360 B1 | 10/2002 | Adam |
| 6,468,293 B2 | 10/2002 | Bonutti et al. |
| 6,475,230 B1 | 11/2002 | Bonutti |
| 6,488,196 B1 | 12/2002 | Fenton |
| 6,500,195 B2 | 12/2002 | Bonutti |
| 6,503,259 B2 | 1/2003 | Huxel et al. |
| 6,530,933 B1 | 3/2003 | Yeung et al. |
| 6,535,764 B2 | 3/2003 | Imran et al. |
| 6,544,267 B1 | 4/2003 | Cole et al. |
| 6,545,390 B1 | 4/2003 | Hahn et al. |
| 6,547,792 B1 | 4/2003 | Tsuji et al. |
| 6,551,304 B1 | 4/2003 | Whalen et al. |
| 6,551,343 B1 | 4/2003 | Tormala |
| 6,554,852 B1 | 4/2003 | Oberlander |
| 6,527,774 B2 | 5/2003 | Lieberman |
| 6,558,390 B2 | 5/2003 | Cragg |
| 6,568,313 B2 | 5/2003 | Fukui et al. |
| 6,569,187 B1 | 5/2003 | Bonutti |
| 6,572,635 B1 | 6/2003 | Bonutti |
| D477,776 S | 7/2003 | Pontaoe |
| 6,557,426 B2 | 7/2003 | Reinemann et al. |
| 6,585,750 B2 | 7/2003 | Bonutti |
| 6,592,609 B1 | 7/2003 | Bonutti |
| 6,594,517 B1 | 7/2003 | Nevo |
| 6,585,764 B2 | 8/2003 | Wright et al. |
| 6,602,293 B1 | 8/2003 | Bierman |
| 6,610,080 B2 | 8/2003 | Morgan |
| 6,605,090 B1 | 9/2003 | Trieu et al. |
| 6,618,910 B1 | 9/2003 | Pontaoe |
| 6,623,487 B1 | 9/2003 | Goshert |
| 6,626,944 B1 | 9/2003 | Taylor |
| 6,623,486 B1 | 10/2003 | Weaver |
| 6,632,245 B2 | 10/2003 | Kim |
| 6,635,073 B2 | 10/2003 | Bonutti |
| 6,638,279 B2 | 10/2003 | Bonutti |
| 6,641,592 B1 | 11/2003 | Sauer et al. |
| 6,645,227 B2 | 11/2003 | Fallin et al. |
| 6,666,877 B2 | 12/2003 | Morgan et al. |
| 6,669,705 B2 | 12/2003 | Westhaver et al. |
| 6,679,888 B2 | 1/2004 | Green et al. |
| 6,685,750 B1 | 2/2004 | Plos et al. |
| 6,699,240 B2 | 3/2004 | Francischelli |
| 6,702,821 B2 | 3/2004 | Bonutti |
| 6,705,179 B1 | 3/2004 | Mohtasham |
| 6,709,457 B1 | 3/2004 | Otte |
| 6,719,765 B2 | 4/2004 | Bonutti |
| 6,719,795 B1 | 4/2004 | Cornwall |
| 6,719,797 B1 | 4/2004 | Ferree |
| 6,722,552 B2 | 4/2004 | Fenton |
| 6,733,531 B1 | 5/2004 | Trieu |
| 6,764,514 B1 | 7/2004 | Li et al. |
| 6,770,078 B2 | 8/2004 | Bonutti |
| 6,780,198 B1 | 8/2004 | Gregoire et al. |
| 6,786,989 B2 | 9/2004 | Torriani et al. |
| 6,796,003 B1 | 9/2004 | Marvel |
| 6,818,010 B2 | 11/2004 | Eichhorn et al. |
| 6,823,871 B2 | 11/2004 | Schmieding |
| 6,830,589 B2 | 12/2004 | Erickson |
| 6,860,885 B2 | 3/2005 | Bonutti |
| 6,878,167 B2 | 4/2005 | Ferree |
| 6,893,434 B2 | 5/2005 | Fenton et al. |
| 6,899,722 B2 | 5/2005 | Bonutti |
| 6,890,334 B2 | 7/2005 | Brace et al. |
| 6,913,666 B1 | 7/2005 | Aeschlimann et al. |
| 6,916,321 B2 | 7/2005 | TenHuisen |
| 6,921,264 B2 | 7/2005 | Mayer et al. |
| 6,923,824 B2 | 8/2005 | Morgan et al. |
| 6,932,835 B2 | 8/2005 | Bonutti |
| 6,942,684 B2 | 9/2005 | Bonutti |
| 6,944,111 B2 | 9/2005 | Nakamura et al. |
| 6,955,540 B2 | 10/2005 | Mayer et al. |
| 6,955,683 B2 | 10/2005 | Bonutti |
| 6,958,077 B2 | 10/2005 | Suddaby |
| 6,981,983 B1 | 1/2006 | Rosenblatt et al. |
| 6,997,940 B2 | 2/2006 | Bonutti |
| 7,001,411 B1 | 2/2006 | Dean |
| 7,004,959 B2 | 2/2006 | Bonutti |
| 7,008,226 B2 | 3/2006 | Mayer et al. |
| 7,033,379 B2 | 4/2006 | Peterson |
| 7,048,755 B2 | 5/2006 | Bonutti |
| 7,066,960 B1 | 6/2006 | Dickman |
| 7,087,073 B2 | 8/2006 | Bonutti |
| 7,090,111 B2 | 8/2006 | Egan et al. |
| 7,094,251 B2 | 8/2006 | Bonutti |
| 7,104,996 B2 | 9/2006 | Bonutti |
| 7,128,763 B1 | 10/2006 | Blatt |
| 7,018,380 B2 | 12/2006 | Cole |
| 7,147,652 B2 | 12/2006 | Bonutti et al. |
| 7,160,405 B2 | 1/2007 | Aeschlimann et al. |
| 7,179,259 B1 | 2/2007 | Gibbs |
| 7,192,448 B2 | 3/2007 | Ferree |
| 7,217,279 B2 | 5/2007 | Reese |
| 7,217,290 B2 | 5/2007 | Bonutti |
| 7,241,297 B2 | 7/2007 | Shaolian et al. |
| 7,250,051 B2 | 7/2007 | Francischelli |
| 7,252,685 B2 | 8/2007 | Bindseil et al. |
| 7,273,497 B2 | 9/2007 | Ferree |
| 7,326,200 B2 | 2/2008 | Trieu |
| 7,329,263 B2 | 2/2008 | Bonutti |
| 7,335,205 B2 | 2/2008 | Aeschliamann |
| 7,429,266 B2 | 9/2008 | Bonutti |
| 7,445,634 B2 | 11/2008 | Trieu |
| 7,481,825 B2 | 1/2009 | Bonutti |
| 7,481,831 B2 | 1/2009 | Bonutti |
| 7,510,895 B2 | 3/2009 | Rateman |
| 7,597,705 B2 | 10/2009 | Forsberg et al. |
| 7,854,750 B2 | 12/2010 | Bonutti |
| 7,879,072 B2 | 2/2011 | Bonutti |
| 7,891,691 B2 | 2/2011 | Bearey |
| 7,967,820 B2 | 6/2011 | Bonutti |
| 8,128,669 B2 | 3/2012 | Bonutti |
| 8,140,982 B2 | 3/2012 | Hamilton, II et al. |
| 8,147,514 B2 | 4/2012 | Bonutti |
| 8,162,977 B2 | 4/2012 | Bonutti et al. |
| 8,487,844 B2 | 7/2013 | Koyama |
| 8,771,314 B2 | 7/2014 | Crombie |
| 8,845,699 B2 | 9/2014 | Bonutti |
| 2001/0002440 A1 | 5/2001 | Bonutti |
| 2001/0008971 A1 | 7/2001 | Schwartz |
| 2001/0009250 A1 | 7/2001 | Herman et al. |
| 2001/0041916 A1 | 11/2001 | Bonutti |
| 2001/0056287 A1 | 12/2001 | Bonutti |

(56) References Cited

U.S. PATENT DOCUMENTS

| | | |
|---|---|---|
| 2002/0016593 A1 | 2/2002 | Hearn et al. |
| 2002/0016633 A1 | 2/2002 | Lin et al. |
| 2002/0019649 A1 | 2/2002 | Sikora |
| 2002/0026244 A1 | 2/2002 | Trieu |
| 2002/0029067 A1 | 3/2002 | Bonutti |
| 2002/0029083 A1 | 3/2002 | Zucherman et al. |
| 2002/0029084 A1 | 3/2002 | Paul et al. |
| 2002/0045902 A1 | 4/2002 | Bonutti |
| 2002/0058966 A1 | 5/2002 | Tormala |
| 2002/0062153 A1 | 5/2002 | Paul et al. |
| 2002/0087189 A1 | 7/2002 | Bonutti |
| 2002/0103495 A1 | 8/2002 | Cole |
| 2002/0120269 A1 | 8/2002 | Lange |
| 2002/0123750 A1 | 9/2002 | Eisermann et al. |
| 2002/0161439 A1 | 10/2002 | Strobel |
| 2002/0183762 A1 | 12/2002 | Anderson et al. |
| 2002/0188301 A1 | 12/2002 | Dallara et al. |
| 2003/0039196 A1 | 2/2003 | Nakamura et al. |
| 2003/0040758 A1 | 2/2003 | Wang et al. |
| 2003/0065361 A1 | 4/2003 | Dreyfuss |
| 2003/0083667 A1 | 5/2003 | Ralph |
| 2003/0097148 A1 | 5/2003 | Valimaa |
| 2003/0105474 A1 | 6/2003 | Bonutti |
| 2003/0118518 A1 | 6/2003 | Hahn et al. |
| 2003/0125749 A1 | 7/2003 | Yuan |
| 2003/0158555 A1 | 8/2003 | Sanders |
| 2003/0158582 A1 | 8/2003 | Bonutti et al. |
| 2003/0167072 A1 | 8/2003 | Oberlander |
| 2003/0181800 A1 | 9/2003 | Bonutti |
| 2003/0195514 A1 | 10/2003 | Trieu |
| 2003/0195530 A1 | 10/2003 | Thill |
| 2003/0195565 A1 | 10/2003 | Bonutti |
| 2003/0204204 A1 | 10/2003 | Bonutti |
| 2003/0208203 A1 | 11/2003 | Lim |
| 2003/0216742 A1 | 11/2003 | Wetzler et al. |
| 2003/0225438 A1 | 12/2003 | Bonutti et al. |
| 2003/0229361 A1 | 12/2003 | Jackson |
| 2004/0010287 A1 | 1/2004 | Bonutti |
| 2004/0024459 A1 | 2/2004 | Ferree |
| 2004/0030341 A1 | 2/2004 | Aeschlimann et al. |
| 2004/0034357 A1 | 2/2004 | Beane et al. |
| 2004/0039392 A1 | 2/2004 | Trieu |
| 2004/0220616 A1 | 2/2004 | Bonutti |
| 2004/0230223 A1 | 2/2004 | Bonutti |
| 2004/0049207 A1 | 3/2004 | Goldfarb |
| 2004/0097939 A1 | 5/2004 | Bonutti |
| 2004/0098050 A1 | 5/2004 | Foerster et al. |
| 2004/0102788 A1 | 5/2004 | Huebner |
| 2004/0116963 A1 | 6/2004 | Lattouf |
| 2004/0138703 A1 | 7/2004 | Alleyne |
| 2004/0138705 A1 | 7/2004 | Heino |
| 2004/0143334 A1 | 7/2004 | Ferree |
| 2004/0167548 A1 | 8/2004 | Bonutti |
| 2004/0172063 A1 | 9/2004 | Li |
| 2004/0186471 A1 | 9/2004 | Trieu |
| 2004/0225325 A1 | 11/2004 | Bonutti |
| 2004/0236374 A1 | 11/2004 | Bonutti et al. |
| 2005/0033362 A1 | 2/2005 | Grafton |
| 2005/0033366 A1 | 2/2005 | Cole |
| 2005/0038514 A1 | 2/2005 | Helm et al. |
| 2005/0043733 A1 | 2/2005 | Eisermann |
| 2005/0043796 A1 | 2/2005 | Grant et al. |
| 2005/0070765 A1 | 3/2005 | Abdelgany |
| 2005/0071012 A1 | 3/2005 | Serhan et al. |
| 2005/0075644 A1 | 4/2005 | DiPoto |
| 2005/0090827 A1 | 4/2005 | Gedebou |
| 2005/0096699 A1 | 5/2005 | Wixey et al. |
| 2005/0113928 A1 | 5/2005 | Cragg et al. |
| 2005/0125072 A1 | 6/2005 | Kolb |
| 2005/0126680 A1 | 6/2005 | Aeschlimann et al. |
| 2005/0143826 A1 | 6/2005 | Zucherman et al. |
| 2005/0240227 A1 | 6/2005 | Bonutti |
| 2005/0149024 A1 | 7/2005 | Ferrante et al. |
| 2005/0149029 A1 | 7/2005 | Bonutti |
| 2005/0203521 A1 | 9/2005 | Bonutti |
| 2005/0216059 A1 | 9/2005 | Bonutti |
| 2005/0216087 A1 | 9/2005 | Zucherman et al. |
| 2005/0222620 A1 | 10/2005 | Bonutti |
| 2005/0234460 A1 | 10/2005 | Miller |
| 2005/0240190 A1 | 10/2005 | Gall et al. |
| 2005/0246021 A1 | 11/2005 | Ringeisen et al. |
| 2005/0256582 A1 | 11/2005 | Ferree |
| 2005/0261684 A1 | 11/2005 | Shaolian et al. |
| 2005/0267481 A1 | 12/2005 | Carl et al. |
| 2005/0267534 A1 | 12/2005 | Bonutti |
| 2005/0283246 A1 | 12/2005 | Cauthen |
| 2006/0009846 A1 | 1/2006 | Trieu |
| 2006/0009855 A1 | 1/2006 | Goble et al. |
| 2006/0015101 A1 | 1/2006 | Warburton et al. |
| 2006/0015108 A1 | 1/2006 | Bonutti |
| 2006/0024357 A1 | 2/2006 | Carpenter et al. |
| 2006/0026244 A1 | 2/2006 | Watson |
| 2006/0142799 A1 | 2/2006 | Bonutti |
| 2006/0200199 A1 | 2/2006 | Bonutti |
| 2006/0229623 A1 | 2/2006 | Bonutti |
| 2006/0064095 A1 | 3/2006 | Senn et al. |
| 2006/0167495 A1 | 3/2006 | Bonutti |
| 2006/0089646 A1 | 4/2006 | Bonutti |
| 2006/0122600 A1 | 6/2006 | Cole |
| 2006/0122704 A1 | 6/2006 | Vresilovic et al. |
| 2006/0235470 A1 | 7/2006 | Bonutti |
| 2006/0241695 A1 | 7/2006 | Bonutti |
| 2006/0265009 A1 | 7/2006 | Bonutti |
| 2006/0265011 A1 | 7/2006 | Bonutti |
| 2006/0189982 A1 | 8/2006 | Lange |
| 2006/0212073 A1 | 9/2006 | Bonutti |
| 2006/0217765 A1 | 9/2006 | Bonutti |
| 2006/0235413 A1 | 10/2006 | Denham |
| 2006/0264953 A1 | 11/2006 | Falahee |
| 2007/0032825 A1 | 2/2007 | Bonutti et al. |
| 2007/0088362 A1 | 4/2007 | Bonutti et al. |
| 2007/0118129 A1 | 5/2007 | Fraser et al. |
| 2007/0198555 A1 | 8/2007 | Friedman et al. |
| 2007/0233092 A1 | 10/2007 | Falahee |
| 2007/0265561 A1 | 11/2007 | Yeung |
| 2007/0270833 A1 | 11/2007 | Bonutti |
| 2008/0021474 A1 | 1/2008 | Bonutti et al. |
| 2008/0039845 A1 | 2/2008 | Bonutti |
| 2008/0039873 A1 | 2/2008 | Bonutti |
| 2008/0046090 A1 | 2/2008 | Paul et al. |
| 2008/0195145 A1 | 2/2008 | Bonutti |
| 2008/0097448 A1 | 4/2008 | Binder et al. |
| 2008/0108897 A1 | 5/2008 | Bonutti et al. |
| 2008/0108916 A1 | 5/2008 | Bonutti |
| 2008/0114399 A1 | 5/2008 | Bonutti |
| 2008/0132950 A1 | 6/2008 | Lange |
| 2008/0140116 A1 | 6/2008 | Bonutti |
| 2008/0140117 A1 | 6/2008 | Bonutti |
| 2008/0269753 A1 | 10/2008 | Cannestra |
| 2008/0269808 A1 | 10/2008 | Gall et al. |
| 2008/0288070 A1* | 11/2008 | Lo ............... A61B 17/0401 623/13.14 |
| 2009/0024161 A1 | 1/2009 | Bonutti |
| 2009/0138014 A1 | 1/2009 | Bonutti |
| 2009/0093684 A1 | 4/2009 | Schorer |
| 2009/0194969 A1 | 8/2009 | Bearey |
| 2010/0211120 A1 | 2/2010 | Bonutti |
| 2010/0262185 A1* | 10/2010 | Gelfand ......... A61B 17/0401 606/232 |
| 2011/0060375 A1 | 3/2011 | Bonutti |
| 2011/0295253 A1 | 12/2011 | Bonutti et al. |
| 2012/0130492 A1* | 5/2012 | Eggli ................. A61F 2/08 623/13.14 |
| 2012/0165841 A1 | 6/2012 | Bonutti |
| 2012/0191140 A1 | 7/2012 | Bonutti |
| 2012/0215233 A1 | 8/2012 | Bonutti et al. |

FOREIGN PATENT DOCUMENTS

| | | |
|---|---|---|
| CA | 2698057 | 3/2009 |
| DE | 1903016 | 10/1964 |
| DE | 1903316 | 10/1964 |
| DE | 1903016 | 8/1970 |
| DE | 3517204 | 11/1986 |

(56) References Cited

FOREIGN PATENT DOCUMENTS

| | | |
|---|---|---|
| DE | 3722538 | 1/1989 |
| DE | 9002844 U1 | 1/1991 |
| EP | 784454 | 5/1996 |
| EP | 773004 | 5/1997 |
| EP | 1614525 | 1/2006 |
| EP | 1988837 | 8/2007 |
| EP | 2134294 | 12/2009 |
| FR | 2717368 | 3/1994 |
| FR | 2696338 | 4/1994 |
| FR | 2728779 | 1/1995 |
| FR | 2736257 | 7/1995 |
| FR | 2750031 | 6/1996 |
| FR | 2771621 | 11/1997 |
| FR | 2785171 | 10/1998 |
| GB | 2093701 A | 9/1982 |
| GB | 2306110 A | 4/1997 |
| JP | 8140982 | 6/1996 |
| SU | 184396 | 7/1966 |
| WO | 91/12779 | 9/1991 |
| WO | 93/23094 | 11/1993 |
| WO | WO1994008642 | 4/1994 |
| WO | 95/16398 | 6/1995 |
| WO | WO 95/31941 | 11/1995 |
| WO | WO1996014802 | 5/1996 |
| WO | WO1997012779 | 4/1997 |
| WO | 97/49347 | 12/1997 |
| WO | WO 97/49347 | 12/1997 |
| WO | WO1998011838 | 3/1998 |
| WO | WO1998026720 | 6/1998 |
| WO | WO2002053011 | 7/2002 |
| WO | 2007/092869 | 8/2007 |
| WO | 2007/092869 A2 | 8/2007 |
| WO | 2008/116203 | 9/2008 |
| WO | 2009/029908 | 3/2009 |
| WO | 2009124215 | 10/2009 |
| WO | WO2010099222 | 2/2010 |

OTHER PUBLICATIONS

Copending U.S. Appl. No. 11/258,795 Non-Final Office Action dated Apr. 26, 2011.
Copending U.S. Appl. No. 11/689,670, RCE Response dated Sep. 19, 2011.
European Search Report dated Sep. 10, 2012 for EP08732724.3.
Copending U.S. Appl. No. 10/614,352, Final Office Action dated Jul. 12, 2010.
Copending U.S. Appl. No. 11/932,602 Final Response to Office Action dated Jun. 10, 2011.
Copending U.S. Appl. No. 11/671,556 Response filed Aug. 23, 2010.
Co-pending U.S. Appl. No. 11/438,537, Supplemental Final Rejection dated Sep. 25, 2009.
Arthrex, Protect your graft, Am J Sports Med, vol. 22, No. 4, Jul.-Aug. 1994.
Barrett et al, T-Fix endoscopic meniscal repair: technique and approach to different types of tears, Apr. 1995, Arthroscopy vol. 11 No. 2 p. 245-51.
Cope, Suture Anchor for Visceral Drainage, AJR, vol. 148 p. 160-162, Jan. 1986.
Gabriel, Arthroscopic Fixation Devices, Wiley Enc. of Biomed Eng., 2006.
Innovasive, We've got you covered, Am J Sports Med, vol. 26, No. 1, Jan.-Feb. 1998.
510k—TranSet Fracture Fixation System, Feb. 24, 2004, k033717.
510k—Linvatec Biomaterials modification of Duet and impact Suture Anchor, Nov. 19, 2004, k042966.
510k, arthrex pushlock, Jun. 29, 2005, K051219.
510k, mitek micro anchor, Nov. 6, 1996, K962511.
510k, Multitak Suture System, Jan. 10, 1997, K964324.
510k, Modified Mitek 3.5mm Absorbable Suture Anchor System, Jun. 9, 1997, K970896.
510K, Summary for Arthrex Inc.'s Bio-Interference Screw, Jul. 9, 1997, K971358.
510k, Surgicraft Bone Tie, Sep. 25, 1998, K982719.
Karlsson et al, Repair of Bankart lesions with a suture anchor in recurrent dislocation of the shoulder, Scand. j. of Med & Science in Sports, 1995, 5:170-174.
Madjar et al, Minimally Invasive Pervaginam Procedures, for the Treatment of Female Stress Incontinence . . . , Artificial Organs, 22 (10) 879-885, 1998.
Nowak et al, Comparative Study of Fixation Techniques in the Open Bankart Operation Using Either a Cannulated Screw or Suture-Anchors, Acta Orthopcedica Belgica, vol. 64—Feb. 1998.
Packer et al, Repair of Acute Scapho-Lunate Dissociation Facilitated by the "Tag." Suture Anchor, Journal of Hand Surgery (British and European vol. 1994) 19B: 5: 563-564.
Richmond, Modificatio of the Bankart reconstruction with a suture anchor, Am J Sports Med, vol. 19, No. 4, p. 343-346, 1991.
Shea et al, Technical Note: Arthroscopic Rotator Cuff Repair Using a Transhumeral Approach to Fixation, Arthroscopy: The Journal of Arthroscopic and Related Surgery, vol. 14, No. 1 Jan.-Feb. 1998: pp. 118-122.
Tfix, Acufex just tied the knot . . . , Am. J. Sports Med., vol. 22, No. 3, May-Jun. 1994.
Wong et al, Case Report: Proper Insertion Angle Is Essential to Prevent Intra-Articular Protrusion of a Knotless Suture Anchor in Shoulder Rotator Cuff Repair, Arthroscopy: The Journal of Arthroscopic and Related Surgery, vol. 26, No. 2 Feb. 2010: pp. 286-290.
Cobb et al, Late Correction of Malunited Intercondylar Humeral Fractures Intra-Articular Osteotomy and Tricortical Bone Grafting, J BoneJointSurg [Br] 1994; 76-B:622-6.
Fellinger, et al, Radial avulsion of the triangular fibrocartilage complex in acute wrist trauma: a new technique for arthroscopic repair, Jun. 1997, Arthroscopy vol. 13 No. 3 p. 370-4.
Hecker et al , Pull-out strength of suture anchors for rotator cuff and Bankart lesion repairs, Nov.-Dec. 1993 , The American Journal of Sports Medicine, vol. 21 No. 6 p. 874-9.
Hernigou et al , Proximal Tibial Osteotomy for Osteoarthritis with Varus Deformity a Ten to Thirteen-Year Follow-Up Study, J Bone Joint Surg, vol. 69-A, No. 3. Mar. 1987, p. 332-354.
Ibarra et al, Glenoid Replacement in Total Shoulder Arthroplasty, The Orthopedic Clinics of Northamerica: Total Shoulder Arthroplasty, vol. 29 No. 3, Jul. 1998 p. 403-413.
Mosca et al, Calcaneal Lengthening for Valgus Deformity of the Hindfoot: Results in Children Who Had Severe, Symptomatic fLATFOOT and Skewfoot, J Bone Joint Surg,, 1195—p. 499-512.
Murphycet al , Radial Opening Wedge Osteotomy in Madelung's Deformity, J. Hand Surg, vol. 21 A No. 6 Nov. 1996, p. 1035-44.
Biomet, Stanmore Modular Hip, J. Bone Joint Surg., vol. 76-B : No. Two, Mar. 1994.
Intl Prelim Rep on Patentability and Written Opinion for PCT/US10/25263 dated Aug. 30, 2011.
IPR—International Publication WO/2008/116203, published Sep. 22, 2009 for PCT/US08/57948.
ISR—International Search Report WO/2008/116203, published Dec. 24, 2008 for PCT/US08/57948.
IPER—Internation Preliminary Report on Patentability, WO/2008/116203, published Sep. 22, 2009 for PCT/US08/57948.
Written Opinion WO/2008/116203 dated Oct. 23, 2008 for PCT/US08/57948.
IPR—International Publication WO2009/029908, published May 3, 2009 for PCT/US08/74941.
ISR—International Search Report, WO2009/029908, published May 3, 2009 for PCT/US08/74941.
IPER—Internation Preliminary Report on Patentability, WO2009/029908, published Mar. 2, 2010 for PCT/US08/74941.
Written Opinion WO2009/029908 dated Feb. 28, 2010 for PCT/US08/74941.
International Search Report PCT/US2010/025263 completed Apr. 13, 2010.
Written Opinion for PCT/US2010/025263 completed Apr. 13, 2010.
The Search for the Holy Grail: A Centrury of Anterior Cruciate Ligament Reconstruction, R. John Naranja, American Journal of Orthopedics, Nov. 1997.

(56) References Cited

OTHER PUBLICATIONS

Femoral Bone Plug Recession in Endoscope Anterior Cruciate Ligament Reconstruction, David E. Taylor, Arthroscopy: The Journal of Arthroscopic and Related Surgery, Aug. 1996.
Meniscus Replacement with Bone Anchors: A Surgical Technique, Arthroscopy: The Journal of Arthroscopic and Related Surgery, 1994.
Problem Solving Report Question No. 1014984.066, Ultrasonic Welding, (c) 1999.
Guide to Ultrasound Plastic Assembly, Ultrasonic Division Publication, (c) 1995.
Branson, Polymers: Characteristics and Compatibility for Ultrasonic Assembly, Applied Technologies Group, Publication unknown.
Enabling Local Drug Delivery-Implant Device Combination Therapies, Surmodics, Inc., (c) 2003.
Stent Based Delivery of Sirolimus Reduces Neointimal Formation in a Porcine Coronary Model, Takeshi Suzuki, American Heart Association, Inc. (c) 2001.
Why Tie a Knot When You Can Use Y-Knot?, Innovasive Devices Inc., (c) 1998.
Ask Oxford, compact Oxford English dictionary: projection, Mar. 30, 2009.
Ask Oxford, compact Oxford English dictionary: slit, Mar. 30, 2009.
Textured Surface Technology, Branson Technolog, Branson Ultrasonics Copr., (c) 1992.
IPR—International Publication WO/2007/092869, publishedAug. 16, 2007 for PCT/US2007/061730.
ISR—International Search Report WO/2007/092869, published Dec. 13, 2007 for PCT/US2007/061730.
Intl Prelim Report on Patentability, WO/2007/092869, published Aug. 12, 2008 for PCT/US2007/061730.
Written Opinion WO/2007/092869 dated Aug. 7, 2008 for PCT/US2007/061730.
Petition for Inter Partes Review of U.S. Pat. No. 5,980,559, IPR 2013-00603, Filing Date Sep. 24, 2013.
Declaration of David Kaplan, Ph.D. Regarding U.S. Pat. No. 5,980,559, IPR 2013-00603, Sep. 24, 2013.
Petition for Inter Partes Review of U.S. Pat. No. 7,087,073, IPR 2013-00604, Filing Date Sep. 24, 2013
Declaration of Wayne J. Sebastianelli, MD Regarding U.S. Pat. No. 7,087,073, Sep. 24, 2013, IPR 2013-00604.
Petition for Inter Partes Review of U.S. Pat. No. 6,500,195, IPR 2013-00624, Filing Date Oct. 2, 2013.
Declaration of Dr. Philip Hardy in Support of Petition for Inter Partes Review of U.S. Pat. No. 6,500,195, IPR 2013-00624, Sep. 25, 2013.
Petition for Inter Partes Review of U.S. Pat. No. 5,527,343, IPR 2013-00628, Filing Date Sep. 26, 2013, Sep. 25, 2013.
Declaration of Dr. Philip Hardy in Support of Petition for Inter Partes Review of U.S. Pat. No. 5,527,343, IPR 2013-00628, Sep. 25, 2013.
Corrected Petition for Inter Partes Review of U.S. Pat. No. 5,921,986, IPR 2013-00631, Filing Date Sep. 27, 2013.
Expert Declaration of Steve E. Jordan, MD, for Inter Partes Review of U.S. Pat. No. 5,921,986, IPR 2013-00631, Sep. 24, 2013.
Corrected Petition for Inter Partes Review of U.S. Pat. No. 8,147,514, IPR 2013-00632, Filing Date Sep. 27, 2013.
Declaration of Steve Jordan for U.S. Pat. No. 8,147,514, from IPR 2013-00632, dated Sep. 23, 2013 (exhibit 1009).
Corrected Petition for Inter Partes Review of U.S. Pat. No. 8,147,514, IPR 2013-00633, Filing Date Sep. 27, 2013.
Declaration of Steve Jordan for U.S. Pat. No. 8,147,514, from IPR 2013-00633, dated Sep. 23, 2013 (exhibit 1006).
Flory, Principles of Polymer Chemistry, 1953, selected pages (cited in IPR 2013-00603, exhibit 1012).
Grizzi, Hydrolytic degradation of devices based on poly(DL-lactic acid) size-dependence, Biomaterials, 1995, vol. 16, No. 4, p. 305-11 (cited in IPR 2013-00603, exhibit 1006).
Gopferich, Mechanisms of polymer degradation and erosion, Biomaterials, 1996, vol. 17, No. 2, p. 103-114 (cited in IPR 2013-00603, exhibit 1013).
Gao et el, Swelling of Hydroxypropyl Methylcellulose Matrix Tablets . . . , J. of Pharmaceutical Sciences, vol. 85, No. 7, Jul. 1996, p. 732-740 (cited in IPR 2013-00603, exhibit 1014).
Linvatec, Impact Suture Anchor brochure, 2004 (cited in IPR 2013-00628, exhibit 1010).
Seitz et al, Repair of the Tibiofibular Syndesmosis with a Flexible Implant, J. of Orthopaedic Trauma, vol. 5, No. 1, p. 78-82, 1991 (cited in IPR 2013-00631, exhibit 1007) (cited in 2013-00632).
Translation of FR2696338 with translators certificate dated Sep. 17, 2013 (cited in IPR 2013-00631, 2013-00632).
Translation of DE9002844.9 with translator's certificate dated Sep. 26, 2013 (cited in IPR 2013-00631, 2013-00632).
Declaration of Steve Jordan for U.S. Pat. No. 5,921,986, from IPR 2013-00632, dated Sep. 24, 2013 (exhibit 1010).
Declaration of Steve Jordan for U.S. Pat. No. 5,921,986, from IPR 2013-00633, dated Sep. 24, 2013 (exhibit 1007).
Declaration of Dr. Steve E. Jordan for U.S. Pat. No. 8,147,514, from IPR 2013-00631, dated Sep. 23, 2013.

\* cited by examiner

FIXATION SYSTEMS AND METHODS

CROSS REFERENCE TO RELATED APPLICATIONS

This non-provisional application is based on and claims priority to U.S. Provisional Application No. 61/749,261 filed Jan. 5, 2013, titled "FIXATION DEVICES AND METHODS", the entire contents of which are hereby expressly incorporated by reference into this disclosure as if set forth fully herein.

FIELD

The present disclosure relates to devices and methods for the fixation of tissues and/or implants in a body of a patient. Embodiments may include devices and methods for securing, approximating, and repairing any soft and/or hard body tissue of humans or other animals.

BACKGROUND

Traditional devices and methods may be configured to achieve fixation along a straight line, for example utilizing straight screws, pins, plates, and rods. In many procedures, these devices primarily purchase harder cortical bone and sometimes cancellous bone. Fractures, especially at or near a joint, may include fragments, for example smaller bone fragments and/or soft tissues attached to the bone fragments. The soft tissues connected to the bone fragments may be necessary for blood flow to these bone fragments but are traditionally not addressed. Detaching the soft tissues from the bone fragments may, for example, weaken the muscular attachments and/or devascularize the bone fragments. Traditional techniques lead to further deterioration of tissues surrounding the fracture.

Also, traditional devices may include implants that are designed to stabilize a larger portion of a fracture but may have difficulty securing soft tissue fragments (i.e. connective tissues) and/or hard tissue fragments (i.e. bone) associated with an injury. These tissues may traditionally be left to heal without support, wrapped with a cable, or drilled through then supported with a wire or pin. Traditional methods may result in periosteal stripping and neurovascular injury resulting from placement of the wire. Also, traditional wires and pins are typically smooth and straight thereby providing limited compression across and access to the fracture. Traditional techniques may be unable to capture soft and hard tissue fragments.

In addition, traditional devices and methods do not secure articular surface fragments. The articular surface must move relative to the adjacent tissues, so a traditional fixation device grabbing an articular surface fragment risks damage to the articular cartilage and the bone on the opposing side of the joint. For example, if the humeral articular surface is damaged, traditional methods do not provide a consistent way to repair the humeral articular cartilage back to its normal size and position. More rigid fixation may damage the glenoid of the articular surface on the opposing side of the joint as the shoulder moves through its range of motion. Traditional techniques are unsuitable for articular surfaces.

There exists a need for a system to repair and secure soft tissue fragments (i.e. muscle, tendon, ligament, and/or articular cartilage) along with hard tissue fragments (i.e. bone). Furthermore, there is a need for a system to repair traditionally unsecured soft tissue fragments thereby stabilizing soft and hard tissue fragments together as a unit. The fixation systems disclosed herein, for example deformable, suture material, and/or mesh fasteners, may secure hard and soft tissue fragments to another device (i.e. plate, screw, and rod), for example, to increase stability. The systems herein may allow capture of a hard tissue fragment (i.e. bone) of a fracture and closure the fracture with a desired compression. This may promote improved tissue healing and/or alleviate issues associated with traditional fixation systems. The systems disclosed herein may be a unitary or standalone solution or be coupled with plates, rods, screws, cables, pins, wires, and/or any traditional system.

SUMMARY

As is described in further detail below, embodiments may include a system for securing first and second body tissue portions of a fracture. Fixation devices may include a base component, an insert component, and a flexible member. The base and/or insert components may include a passage. The insert component may be positionable within at least a portion of the passage of the base component. The elongate member may be configured to be positioned through the first and second body tissue portions. The elongate member may be tensioned and pinched between the base component and insert component or within the passage of the insert component, for example, to secure the first and second body tissue portions.

Further embodiments may include a fixation device, an elongate member, and a bone clamp. The elongate member may be configured to be positioned through first and second body tissue portions. The bone clamp may be configured to urge the first and second body tissue portions together. The elongate member may be tensioned and secured with the fixation device to secure the first and second body tissue portions.

In another embodiment, a system may include a base component, insert component, fastener, and elongate member. The base component may include a passage. The insert component may be positionable within at least a portion of the passage of the base component. The fastener may be configured to be positioned through the first and second body tissue portions and on a distal tissue surface. The elongate member may be configured to connect the fastener on the distal body tissue surface and positioned between the base component and insert component on a proximal tissue surface. The elongate member may be tensioned and pinched between the base component and insert component to secure fixation device relative to the elongate member thereby securing the first and second tissue portions.

Embodiments may also include methods of positioning first and second body tissue portions. Methods may include passing a fastener connected to an elongate member through first and second body tissue portions, securing the fastener relative to a distal body tissue surface, positioning a base component of a fixation device along the elongate member, tensioning the elongate member, and/or positioning an insert component of a fixation device into a portion of the base component and against the elongate member. The elongate member may be pinched between the base component and insert component thereby securing the first and second body tissue portions relative to each other.

As an additional embodiment, methods may include positioning a fixation system for securing a fracture of a joint of a body. The method may comprise passing a fastener connected to an elongate member through proximal and distal fragments of the fracture, positioning the fastener against the distal fragment, securing a plate with respect to the proximal fragment, tensioning the elongate member to urge the first and second fragments together, and/or locking a fixation device against the elongate member and the plate.

Further embodiments may include a method of using a fixation system to repair a defect in a passage. The method may comprise positioning an implant disposed over an introducer adjacent the defect in the passage, expanding the introducer radially to urge the implant against the passage, contracting the introducer radially while the implant remains expanded against the passage; and retracting the introducer axially while the implant remains in the passage.

Additional embodiments of the present disclosure are provided throughout this disclosure including the accompanying drawings.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein:

FIG. 120 illustrates an embodiment of FIGS. 60-62, for example, including an implant such as a nail or rod;

FIG. 121 illustrates an embodiment of FIG. 119-120, for example, including a fastener connected to a head of a screw; and FIG. 122 illustrates an embodiment of the present disclosure, for example, including an implant such as a scaffold.

DETAILED DESCRIPTION

Figure 1:
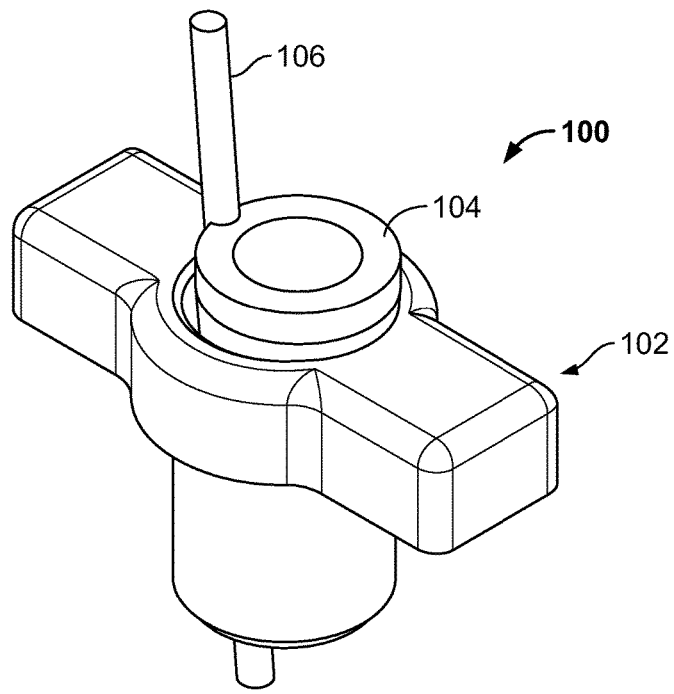
FIG. 1 illustrates an isometric view of an embodiment of the present disclosure, for example, including a base component, an insert component, and an elongate member of a fixation device.

The present disclosure relates to devices and methods for fixation of tissues in a body of a human or other animal. Embodiments may include a fixation device comprised of a single or one or more components. The fixation device may be attached relative to an elongate member, for example, to secure soft and/or hard body tissues. The fixation device may be used alone, with one or more other fixation devices, or may be used with fasteners, screws, plates, rods, cables, pins, and/or wires. One or more fixation device may be utilized to secure a single or one or more elongate members.

Embodiments may relate to the repair, reconstruction, augmentation, and stabilization of tissue and/or implants. Embodiments may be utilized during a medical procedure and/or "on the way out" after the procedure has been performed. Hard and/or soft tissue at and around the procedure site and the tissue between the procedure site and the skin incision may be compressed and/or repaired. This may entirely or partially restore tissue function and/or stabilize the treatment area for enhanced healing. The embodiments herein may be used with any medical or surgical procedure, for example a ligament repair, tendon repair, muscle repair, bone repair, cartilage repair, and repair of any other tissue type. Ligaments may be fastened to ligaments, ligaments to bones, bones to bones, ligaments to muscles, muscles to muscles, tissue grafts to bone, tissue grafts to ligaments, grafts to grafts, and any other combination of tissues and/or implants. The embodiments herein may be utilized with minimally invasive techniques.

Embodiments herein may be configured to repair soft tissue (i.e. muscle, tendon, ligament, and/or articular cartilage) fragments along with hard tissue (i.e. bone) fragments together as a unit. Traditional screws and pins may be insufficient to stabilize the fragments. However, fixation devices, for example including deforming, all suture material, and/or mesh fasteners, may grab and stabilize bone along with muscles, tendons, ligaments, and/or articular cartilage. Also, fixation devices may reattach these tissues to larger structures (i.e. plates, screws, rods, and/or other implants) to create a more stable construct.

Further embodiments may be configured for soft tissue fragments, for example, to restore an articular surface. For example, a deformable fastener connected to an elongate member may be positioned through an articular cartilage fragment to pull the articular cartilage fragment to the articular surface. This may facilitate range of motion of the joint while minimizing damage to the bone on the opposite side of the joint, for example a glenoid or any other joint surface.

The technologies disclosed herein also allow for fixation of bone-to-bone, tissue-to-bone, and/or tissue-to-tissue. Bone fractures may damage the soft tissues (i.e. tendons and/or ligaments) near the fracture. The embodiments herein may allow for a composite system that may provide stability while repairing the tissue around the fracture. For example, embodiments may be used to repair an anterior cruciate ligament (ACL) or stabilize an ACL graft, allograft and/or autograft. Embodiments may also be used for rotator cuff tendon repair in which the tendon could be repaired around the tendon or around the bone. Also, bone-to-bone fixation may be achieved by grasping the tendon bone construct.

Embodiments may provide broader capabilities in fixing different types of fracture fragments. In situations with osteoporotic bone or other deteriorated tissues, the tendon-bone interface or ligament-bone interface may be stronger than an osteoporotic or deteriorated cortical portion. Fixation may be achieved by securing to the tendon or ligament portion, which may be more stable than grabbing the osteoporotic bone fragment alone. As another example, embodiments may be used in pediatric fractures where there may be a growth plate-epiphysis. An elongate member may be positioned through the epiphysis without the unnecessary bone growth restriction that may be a consequence of rigid fixation such as a screw, plate, or rod. The embodiments herein may be configured for soft tissue fixation by providing an angle, bend, or curve to avoid or access through a passage through the epiphysis. These techniques may facilitate treatment while preserving tissue and/or reducing growth abnormalities.

In an embodiment, devices and methods for stabilizing and/or repairing a body joint may be provided. A fixation device (i.e. a fastener) may be positioned in contact with a first body tissue, for example, on one side of the joint (i.e. at a distal area). Another fixation device may be positioned in contact with second body tissue, for example, on the other side of the joint (i.e. at a proximal area). An elongate member may be positioned and/or connected between the fixation devices and/or tensioned. The tensioned elongate member may be secured to the fixation devices, for example, to restrict or restore normal movement of the joint. The fixation devices may be positioned in contact with any outer or inner surface of the body.

The elongate member may be positioned adjacent to and/or through the tissue, for example, of the joint. The elongate member may include a suture, wire, cable, or any combination thereof. Elongate members may be flexible or bendable. The elongate member may include one or more flexible filaments. All or any portion of elongate member may be degradable, biodegradable, bioabsorbable, or non-biodegradable. The elongate member may be configured to change shape or dimensions with energy, for example thermal or vibratory energy (i.e. ultrasonic energy). Elongate member may tighten, loosen, and/or contract with heat. Heat may include body heat a portion of the body or applied thermal or vibratory energy. The elongate member may include polyethylene, polyester, cat gut, silk, nylon, polypropylene, linen, cotton, PLA, PGA, caprolactam, and copolymers of glycolic and lactic acid. The elongate member may be threadlike, monofilament, multifilament, braided, woven, or inter-laced. The elongate member may include a coating of therapeutic substances or drugs. The elongate members may include anti-biotics, hydroxyapatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immunosuppressants, fibrin, osteoinductive materials, apatite compositions, fetal cells, stem cells, enzymes, proteins, hormones, and germicides.

Body tissue may include any soft tissue, hard tissue, or any combination thereof. Body tissues may include bones, muscles, ligaments, tendons, nerves, fascia, skin, fibrous tissues, fat, synovial membranes, organs, collagen, cartilage, fascia, blood vessels, and tissue grafts. These may be tissues of any portion of the body, for example a knee, ankle, elbow, wrist, feet, hand, hip, shoulder, jaw, and spine. Bones of the knee may include the femur, tibia, and patella. Ligaments of the knee may include the medial collateral ligament, lateral collateral ligament, posterior oblique ligament, arcuate ligament, oblique popliteal ligament, anterior cruciate ligament, and posterior cruciate ligament. Bones of the spine may include transverse process, pedicle, facet, spinous process, posterior arch, odontoid process, posterior tubercle, lateral articular process, uncinate process, anterior tubercle, carotid tubercle, lamina, and vertebral body. Ligaments of the spine may include the anterior longitudinal ligament, posterior longitudinal ligament, interspinous ligaments, supraspinous ligament, ligamentum flavum, intertransverse ligament, facet capsulary ligament, ligamentum nuchae, and ligaments of the sacrum and coccyx spine. Tissue grafts may include a xenograft, allograft, autograft, and/or synthetic graft material. Embodiments may also be made from a porous matrix or mesh of biocompatible and bioresorbable fibers acting as a scaffold to regenerate tissue. Embodiments may be configured to repair or stabilize articular surfaces, metaphyseal areas, periarticular fractures, implants (i.e. cochlear implants), oral or facial injuries (i.e. oral maxillary facial injuries), and arthroplasty components of any joint including the spine.

Further embodiments may be degradable, biodegradable, bioerodible, bioabsorbable, mechanically expandable, hydrophilic, bendable, deformable, malleable, riveting, threaded, toggling, barbed, bubbled, laminated, coated, blocking, pneumatic, one-piece, Morse taper, single piece, multi-component, solid, hollow, polygon-shaped, pointed, locking and unlocking, self-introducing, knotless, and combinations thereof. Also, embodiments may include a metallic material, polymeric material, ceramic material, composite material, body tissue, synthetic tissue, hydrophilic material, expandable material, compressible material, heat bondable material, biocompatible adhesive, porous material, matrix or mesh material, and combinations thereof. All or any portion of the embodiments herein may include an expandable material and/or an expandable coating. The embodiments may be configured to be compressed then expanded. Alternatively, embodiments may be hydrophilic, expandable with liquid, PEEK, PTFE, desiccated body tissue, and/or any other material disclosed herein. Embodiments may include any combination of materials disclosed herein. For example, embodiments may include combinations of hydrophilic material, synthetic body tissue, collagen, synthetic collagen, heat bonded material, biocompatible adhesive, and cells (i.e. stem cells). Embodiments may include or be used in conjunction with any devices and methods disclosed in U.S. Pat. No. 5,718,717, titled "Suture Anchor", which is hereby incorporated by reference in its entirety.

Embodiments may be any of biocompatible, degradable, biodegradable, bioerodible, bioabsorbable, mechanically expandable, hydrophilic, bendable, deformable, malleable, riveting, threaded, toggling, barbed, bubbled, laminated, coated, blocking, pneumatic, one-piece, multi-component, solid, hollow, polygon-shaped, pointed, self-introducing, mesh, segmented, tubular, braided, suture material, elastic (i.e. rubber, silicone, or any other elastic material), and combinations thereof. Furthermore, embodiments may include any of a metallic material, polymeric material, ceramic material, composite material, body tissue, synthetic tissue, hydrophilic material, expandable material, compressible material, bondable material, and combinations thereof. Embodiments may also include polymethyl methacrylate (PMMA or "bone cement"), glue, adhesive, grouting agents, acrylic materials, and combinations thereof.

Additional embodiments herein may include any biocompatible materials or any other materials suitable for medical use. All or any portion of the embodiments herein may be any metallic, non-metallic, composite, ceramic, polymeric, copolymeric, biologic, or synthetic material or any combination thereof. Embodiments may include portions and/or combinations of metals and polymers. Embodiments may include shape memory alloys (SMA) and/or shape memory polymers (SMP). Examples of amorphous polymers are polycarbonate (LEXAN), polystyrene, polysulfone (ULDALL), and acrylics polycarbonate (ABS and styrenes). Examples of semi-crystalline polymers include acetyl (DELRIN), nylon, polyester, polyethylene, polyether ether ketone, polypropylene, polyvinylchloride (PVC), and Caprolactam. Biodegradable semi-crystalline polymers may include polylactic acid and polyglycolic acid. Copolymers of PGA and PLA may also be used. Poly-1-lactide (PLLA)

or other forms of PLA may also be used. Other polymers which may be used with the present invention, either as a thermoplastic or non-thermoplastic, are polyethylene glycol (PEG)-copolymers and D,L-lactide-co-glycolide polyesters. Some semi-crystalline materials are particularly suitable for surgical bonding and/or staking, especially vibratory bonding and staking Examples of such materials include PAEK (polyaryletherketone), PEEK (polyetheretherketone) and PEKK (polyetherketoneketone). Metals include stainless steel, shape metal alloys, tantalum, porous tantalum, titanium, and cobalt-chrome alloys. Shape memory alloys may include nitinol (nikel-titanium). Shape memory polymers may include PEEK, PMMA, and thermoset polymers. Thermoset polymers may include polyurethanes, polyethylene terephthalate (PET), polyethyleneoxide (PEO), block copolymers containing polystyrene and poly(1,4-butadiene), and ABA triblock copolymers, for example including poly(2-methyl-2-oxazoline) and polytetrahydrofuran. Ceramic materials (i.e. implants) may include silicon nitride, alumina (aluminum oxide), and zircon (zirconium dioxide). Embodiments may include materials configured to resist growth of bacteria and/or biofilm, for example silicon nitride.

Embodiments may be configured to access any treatment site, for example any portion of the body. Embodiments may be configured to transfer objects and/or materials into and/or from the treatment site. Embodiments may utilize a natural body passage or create a passage. The passage may be created through soft or hard tissue. Embodiments may be partially or entirely flexible, curved, non-linear, bendable, and/or may have shape memory properties or materials, which may allow all or any portion of the system to change in shape. A change in shape may include a change in angle, which may range between about 0-180 degrees. Use of a shape memory material may allow the angle to vary within a range of about 0-180 degrees with a change in temperature and/or by the application of heat. Embodiments may be shaped and/or positioned to access a curved or natural anatomic path through the body. Embodiments may be used in conjunction with any devices or methods disclosed in U.S. Pat. No. 6,814,715, titled "Expandable Cannula", U.S. Patent Application Publication Nos. 2011/0202123, titled "Anatomic Needle System" and 2011/0224539, titled "Methods for Positioning an Ultrasonic Catheter", and U.S. patent application Ser. No. 13/683,847, titled "Expandable Access Systems and Methods", all of which are hereby incorporated by reference in their entirety.

The methods and devices disclosed herein may be used in conjunction with any medical procedure. Embodiments may be used before, during, or after a procedure. Treatment areas may include any cavity, vessel, duct, passage, joint, bone, muscle, ligament, tendon, cartilage, capsule, organ, skin, nerve, or other body parts. Embodiments may be used for applications related to biliary ducts, bronchi (i.e. cystic fibrosis), kidney stones, bile ducts, sinus ducts, bone cavities, the vasculature, and any other site in the body. As further examples, embodiments herein may be used in or in conjunction with other medical instruments during sinuplasty, lithotripsy, intervertebral disc surgery, kyphoplasty, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, shoulder surgery, hernia repair surgery, and surgery of an intrasubstance ligament tear, annulus fibrosis, fascia lata, or flexor tendons. Treatment areas include the ear, prostate, biliary ducts, bronchi (i.e. cystic fibrosis), kidney stones, bile ducts, sinuses (i.e. sinusitis), small or large intestines (i.e. diverticulitis), bone cavities, and/or vasculature. Embodiment may be used in any medical application or body portion disclosed herein, disclosed in the incorporated references, or known in the art.

Embodiments may be configured to be used in conjunction with other medical instruments or implants. Embodiments may be configured to position and/or prepare the treatment site for another medical instrument or implant. Instruments may include any dilator, trocar, introducer, imaging device, or any other device or material disclosed herein. Implants may include a coronary artery stent, vascular stent, peripheral vascular stent, urinary tract stent, or urethral stent. Implants may include a partial or total knee replacement, hip replacement, shoulder replacement, bone fastener, etc. Objects may include an organ, partial organ grafts, tissue graft material (i.e. autogenic, allogenic, xenogenic, or synthetic), collagen, a malleable implant like a sponge, mesh, bag/sac/pouch, collagen, or gelatin, or a rigid implant made of metal (i.e. porous or nonporous), polymer, composite, or ceramic. Other implants include breast implants, biodegradable plates, porcine or bovine patches, metallic fasteners, compliant bearing for medial compartment of the knee, nucleus pulposus prosthetics, stents, fasteners, sutures, suture anchors, tissue grafts, or tissue scaffolds.

Tissue scaffolds may include any biologic, synthetic, biodegradable, collagen, polymeric and/or biocompatible scaffold. The scaffold may include a collagen matrix configured to receive viable cells of any type. The matrix may be utilized as a support structure for cells. Different types of cells may be placed at various locations in the matrix. The matrix may be positioned relative to any portion of a patient's body, for example all or any portion of a heart, blood vessel, brain, intestine, stomach, adrenal gland, liver, pancreas, bone, skeleton, spinal cord, or any other organ or any soft or hard tissue. The cell types may include progenitor cells which differentiate and proliferate to form cells having desired characteristics, stromal cells which relate to foundation supporting tissue, and mesenchymal cells which relate to connective tissues, blood and blood vessels, and other systems. Fibroblasts may be used in the production of connective tissues. Osteoblasts may be used in the production of hard tissue (i.e. bone). Myoblasts may be used in the production of muscle. Specific cells may be used to provide for growth of tissue having a function associated with the cell, which may include reticular cells, smooth muscle cells, chondrocytes, retinal cells, endothelial cells, fetal cells, stem cells, embryonic cells, adult cells, enzymes, proteins, and/or other cells disclosed herein or known in the art. Once the viable cells have been positioned on the matrix, the result is a replacement tissue (i.e. an organ). Embodiments of the present disclosure may include the additional devices and methods disclosed in U.S. Pat. No. 7,299,805, titled "Scaffold and Method for Implanting Cells", which is hereby incorporated by reference in its entirety. Embodiments may also include biofilm that is sterilized to allow sterile biofilm to be used as an adhesive for scaffolds or used as a drug release agent.

Referring to the FIGS. 1-38, embodiments may include fixation device 100. Fixation device 100 may include any or all of base component 102, insert component 104, and/or elongate member 106. Fixation device 100 may be positionable with respect to any body tissue or portion of the body. Fixation device 100 may be positionable at a distal tissue area or a proximal tissue area. Fixation device 100 may include fastener 116.

Figure 2:
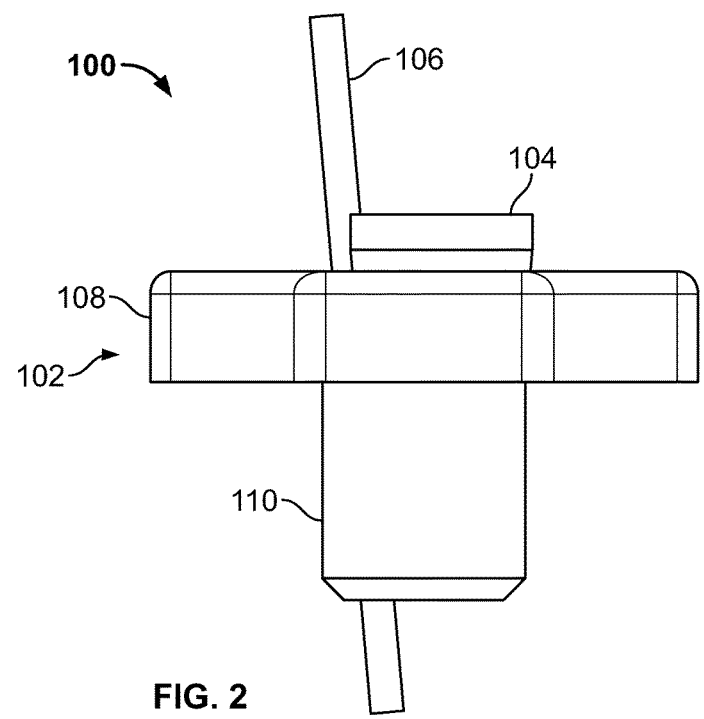
FIG. 2 illustrates a front view of an embodiment of FIG. 1.
Figure 3:
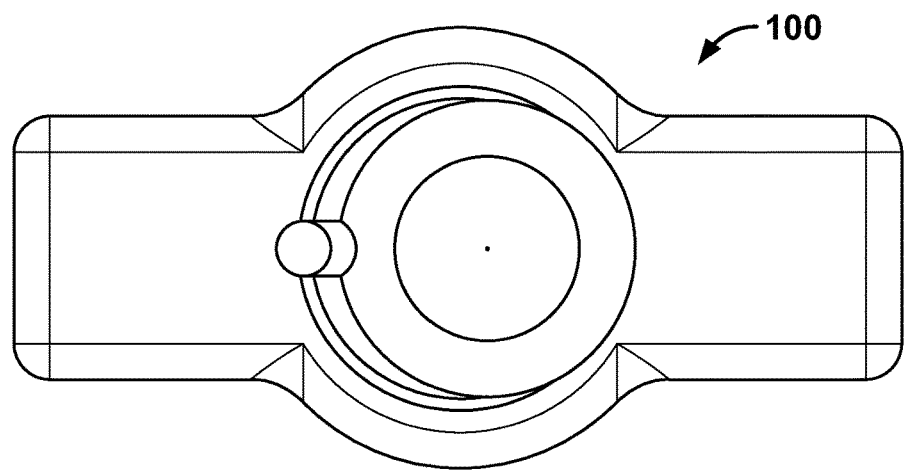
FIG. 3 illustrates a top view of an embodiment of FIG. 1.
Figure 4:
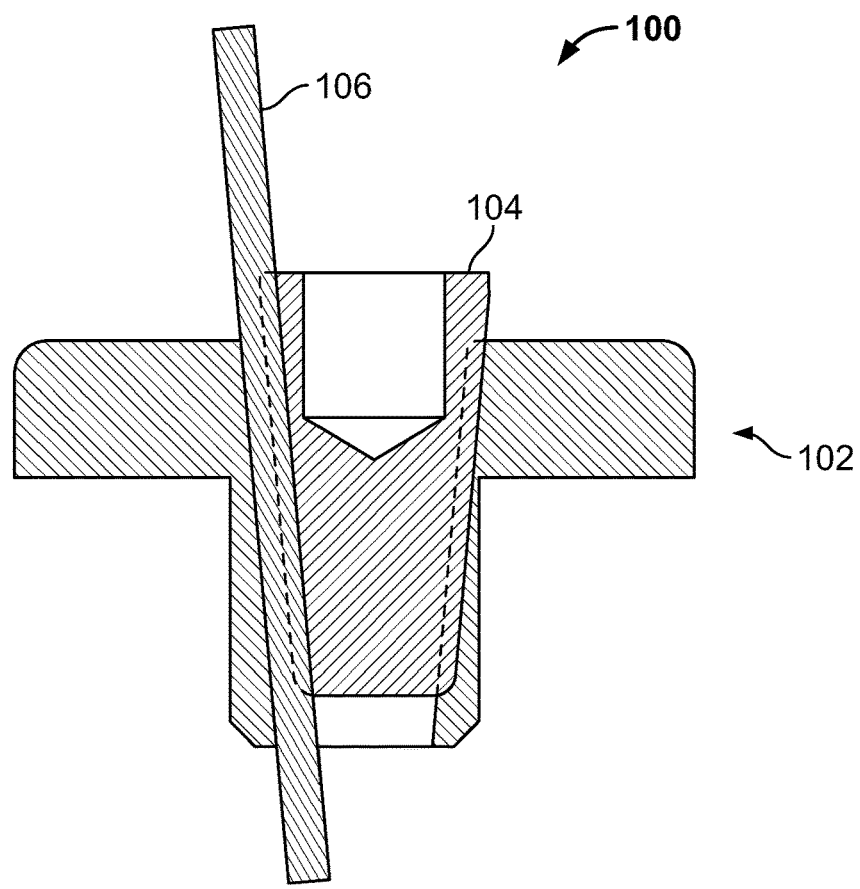
FIG. 4 illustrates a front section view of an embodiment of FIG. 1.

Base component 102 may include elongate and/or cylindrical body 110 and head portion 108, which may include one, two, or more tabs that may be configured to be positioned on a surface of a body tissue. (FIG. 2). Base component 102 may include a passage through all or any portion of its length. (FIG. 3-4). Base component 102 may be configured to directly contact and/or fit into the body tissue. Base component 102 may be positionable in a body tissue hole that is natural, drilled, punched, cut, or formed. Leading portion 110 of base component 102 may be positionable into the body tissue. Head portion 108 may be configured to retain insert component 104. Head portion 108 may assist in the positioning of base component 102 and/or resist recession of base component 102 into the body tissue hole. Base component 102 may be positioned with elongate member 106 passing through all or any portion of the length of base component 102. (FIG. 4).

Insert component 104 may be positionable in all or any portion of the passage of base component 102 or into any other embodiment herein. (FIG. 4). Insert component 104 may be positioned before, during, or after base component 102 is positioned in the body of the patient. Insert component 104 may be secured in the passage of base component 102 to secure elongate member 106 with respect to body tissue and/or additional fixation devices. Elongate member 106 may be secured with mechanical features, press fitting, screwing, crimping, squeezing, melting, thermal or ultrasonic joining, gluing, or any other method disclosed herein.

Fixation device 100 may include one or more tapers. (FIG. 4). Base component 102 and/or insert component 104 may include a taper on any surface, for example any interior and/or exterior surface. The taper may be configured to progressively increase and/or decrease along its length or circumference, for example, to provide varying fixation relative to elongate member 106. An interior surface taper of base component 102 may be configured to approximate an exterior surface taper of insert component 104. The taper may provide additional locking as elongate member 106 is tensioned through a tissue passage and/or insert component 104 is urged into base component 102. Insert component 104 (i.e. outer surface) and base component 102 (i.e. inner surface of the passage) may include tapered surfaces along all or a portion of their length, for example, to accentuate locking and/or securing of elongate member 106. Elongate member 106 may be secured by trapping elongate member 106 between base component 102 and insert component 104, for example, when insert component 104 is pressed into the passage of base component 102.

Elongate member 106 may be secured at any point along its length. Elongate member 106 may include a suture, wire, cable, pin, screw, elongate device, fastener, any combination thereof, or any other device disclosed herein. All or any portion of base component 102, insert component 104, and/or elongate member 106 may deform relative to each other, for example, to secure elongate member 106. (FIG. 4). All or any portion of base component 102, insert component 104, and/or elongate member 106 may be bonded, deformed, and/or secured relative elongate member 106.

Figure 5:
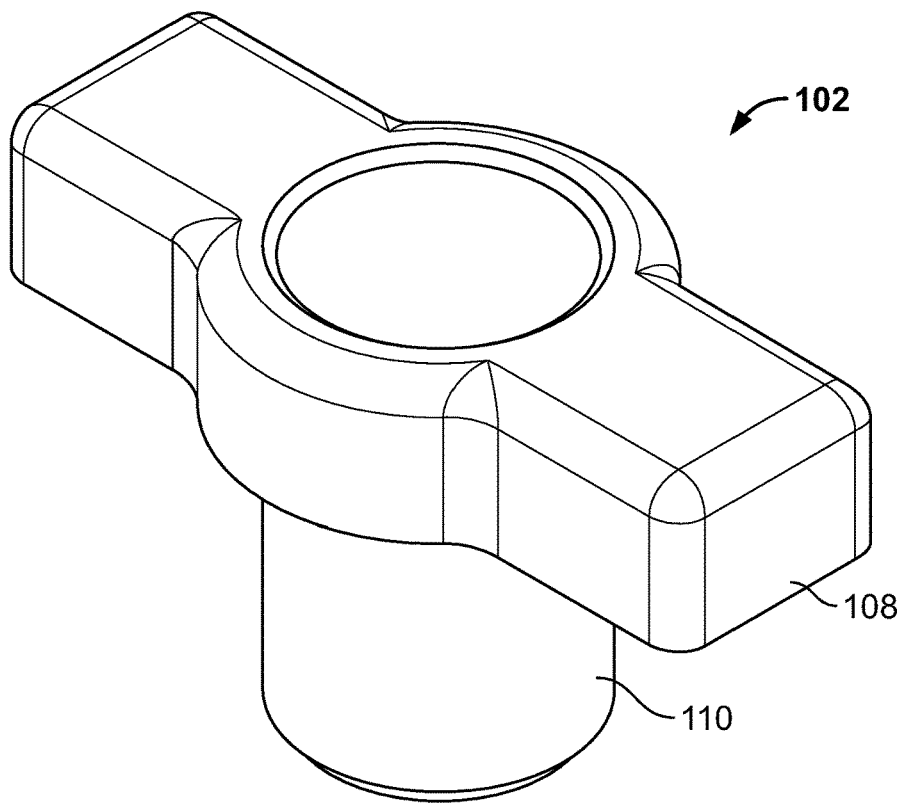
FIG. 5 illustrates an isometric view of a base component.
Figure 6:
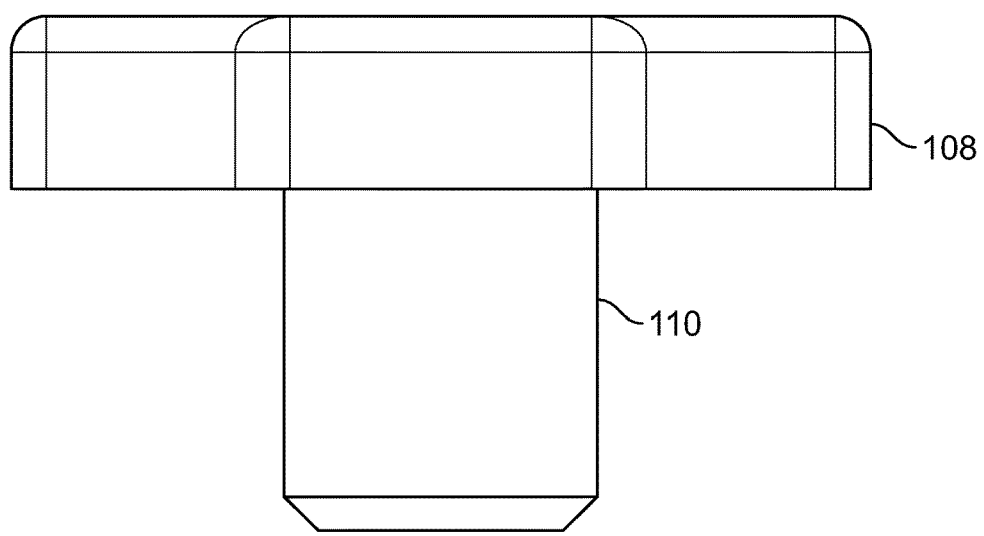
FIG. 6 illustrates a front view of an embodiment of FIG. 5.
Figure 7:
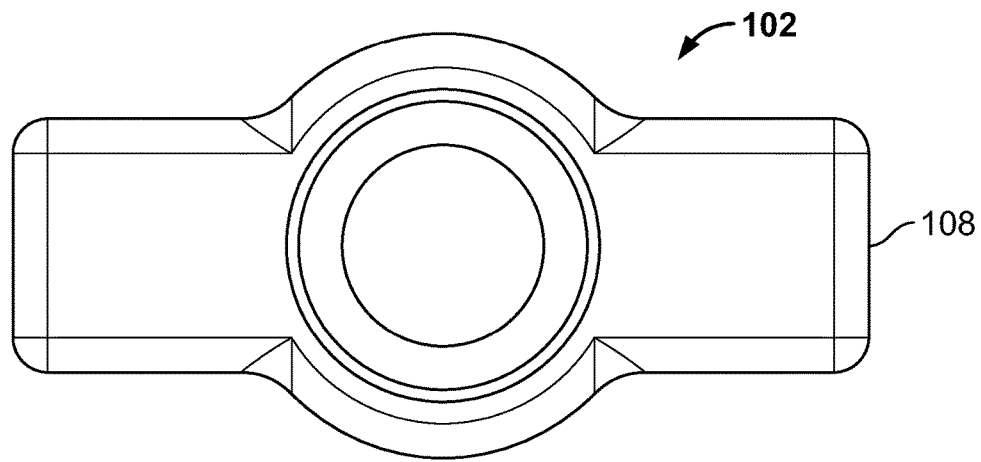
FIG. 7 illustrates a top view of an embodiment of FIG. 5.

Body portion 110 may be configured to fit inside a passage in body tissue and/or include a cylindrical shape or any other shape disclosed herein. (FIG. 5). Head portion 108 may consist of one, two, or more tabs which may resist base component 102 from being pulled into and/or through the body tissue. Base component 102 may be configured to a length that will allow sufficient locking relative to elongate member 106. Head portion 108 of base component 102 may be configured to a thickness to resist recession into body tissue. The width and/or length of the tabs may also be configured to resist pulling of base component 102 into and/or through tissue. Any embodiment herein, for example the edges of head portion 108 of base component 102, may be radiused, chamfered, broken, smoothed, ground, or otherwise processed to remove sharpness and/or provide a lead-in.

Body portion 110 of base component 102 may be centrally located or offset to an end (not shown). (FIGS. 5-8). The passage may be centered or offset (not shown) with respect to body portion 110. All or any portion of the cross-sectional shape of body portion 110 may be circular (as shown), triangular, square, rectangular, pentagonal, hexagonal, or any other round or polygonal shape. Embodiments, for example one or more ends, may be radiused, chamfered, broken, smoothed, ground, blunted, or otherwise processed to remove sharpness and/or provide a lead-in.

Figure 8:
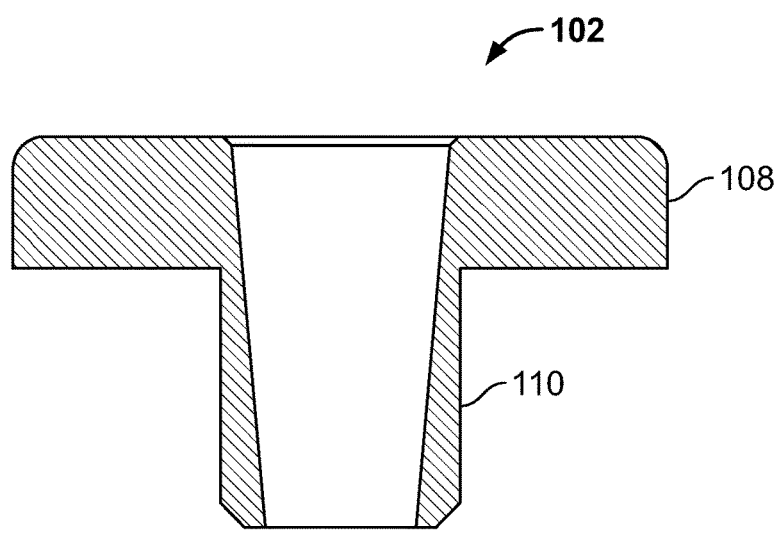
FIG. 8 illustrates a front section view of an embodiment of FIG. 5, for example, including a tapered inner surface.

All or any portion of base component 102 may include a passage. (FIG. 8). The passage may be centrally located and/or may include a taper from an upper end of head portion 108 to a lower end of body portion 110. The cross-sectional shape of the passage may be circular (as shown), triangular, square, rectangular, pentagonal, hexagonal, or any other round or polygon. The passage of any embodiment, for example the upper or lower ends, may be radiused, chamfered, broken, smoothed, ground, or otherwise processed to remove their sharpness and/or provide a lead-in. The surface of the passage of any embodiment may be smooth (shown), textured, notched, ringed, stepped, and/or roughened.

Figure 9:
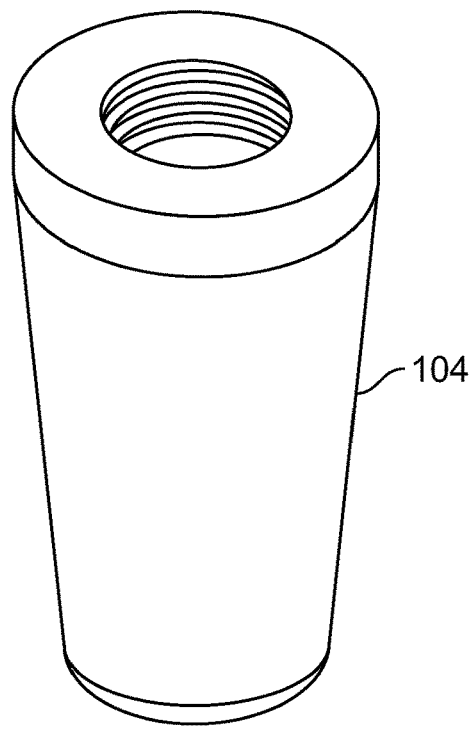
FIG. 9 illustrates an isometric view of an insert component of a fixation device, for example, including an external tapered surface and/or an internal attachment feature.
Figure 10:
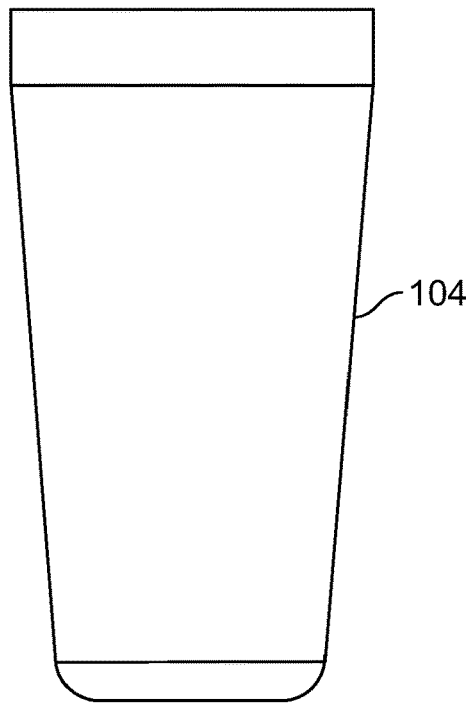
FIG. 10 illustrates a front view of an embodiment of FIG. 9.

Insert component 104 may include a taper and/or a cross-sectional shape that is circular, triangular, square, rectangular, pentagonal, hexagonal, or any other round or polygon. (FIGS. 9-12). The taper may run from an upper end to a lower end of insert component 104. The taper angle of insert component 104 and base component 102 may be substantially equal or matched. Alternatively, the taper angles of the two components may be different, offset, or opposite. All or any portion of insert component 104 may have no taper (i.e. upper portion of insert component 104), a linear taper (i.e. middle portion of insert component 104), and/or a varying or non-linear taper (i.e. lower portion of insert component 104). (FIG. 10). Any surface or edge of any embodiment herein, for example insert component 104, may be radiused (shown), chamfered, broken, smoothed, ground, or otherwise processed to remove sharpness and/or provide a lead-in.

Figure 11:
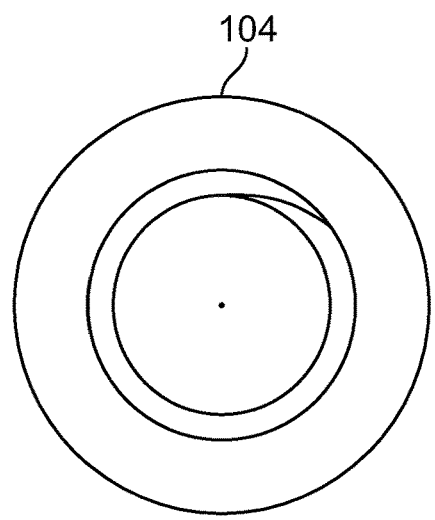
FIG. 11 illustrates a top view of an embodiment of FIG. 9, for example, including a passage.
Figure 12:
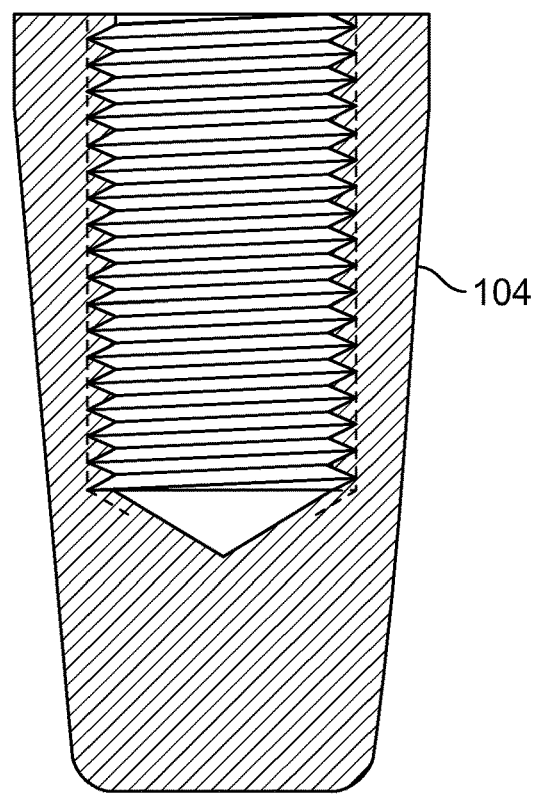
FIG. 12 illustrates a section view of an embodiment of FIG. 9, for example, including an internal attachment feature.
Figure 13:
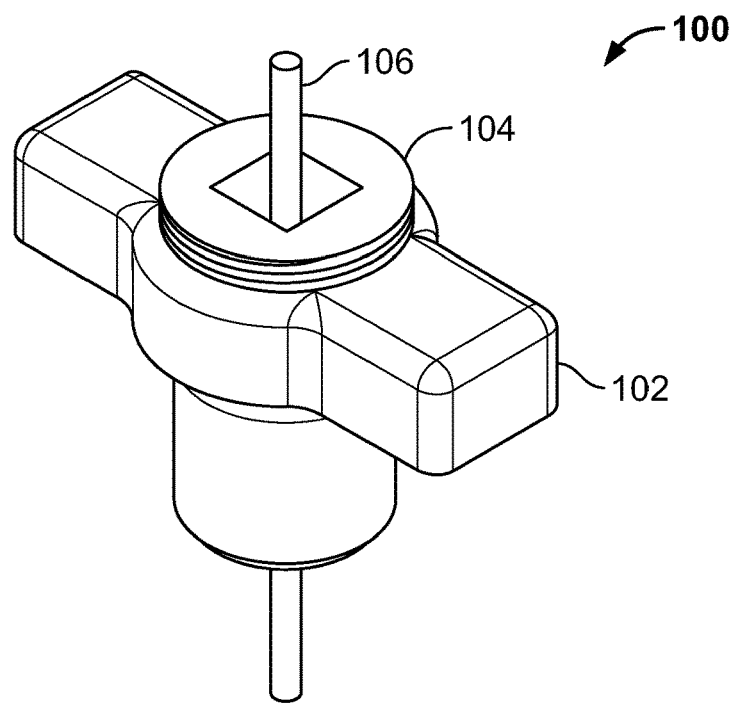
FIG. 13 illustrates an isometric view of an alternative embodiment, for example, including a base component, an insert component, and an elongate member of a fixation device.
Figure 14:
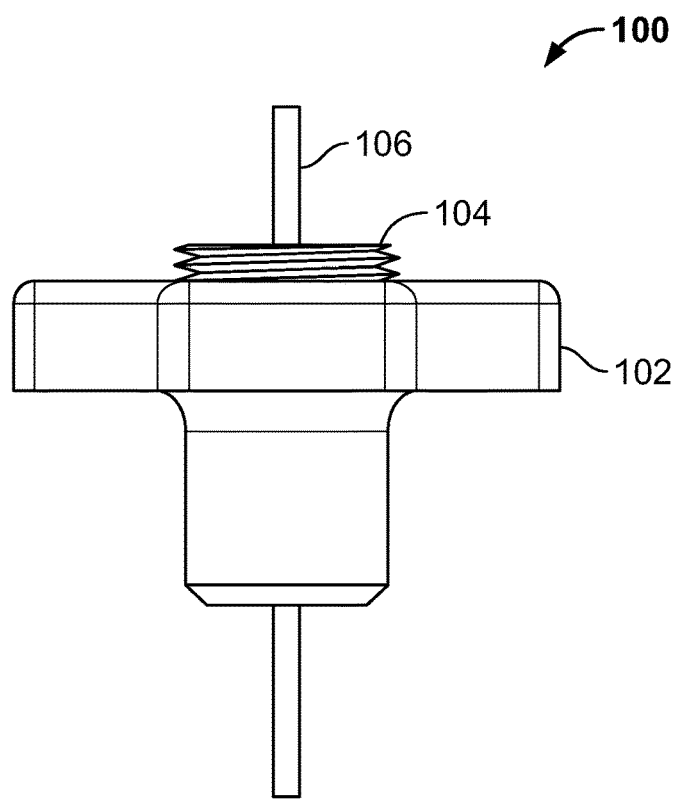
FIG. 14 illustrates a front view of an embodiment of FIG. 13.
Figure 15:
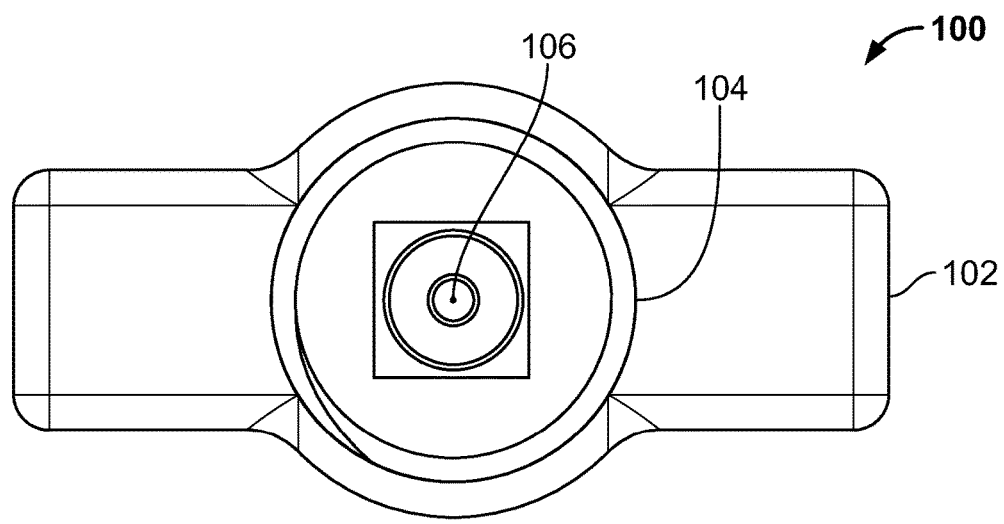
FIG. 15 illustrates a top view of an embodiment of FIG. 13.
Figure 16:
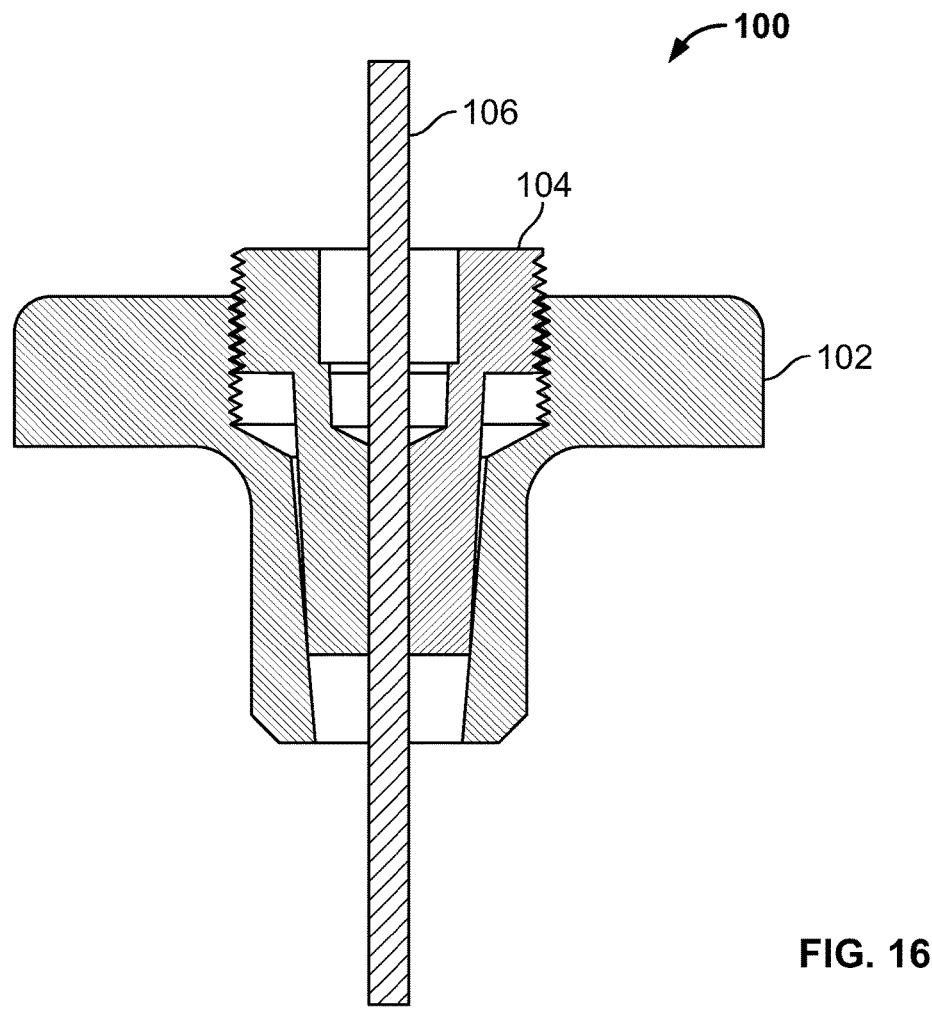
FIG. 16 illustrates a front section view of an embodiment of FIG. 13, for example, including internal and external attachment features.
Figure 17:
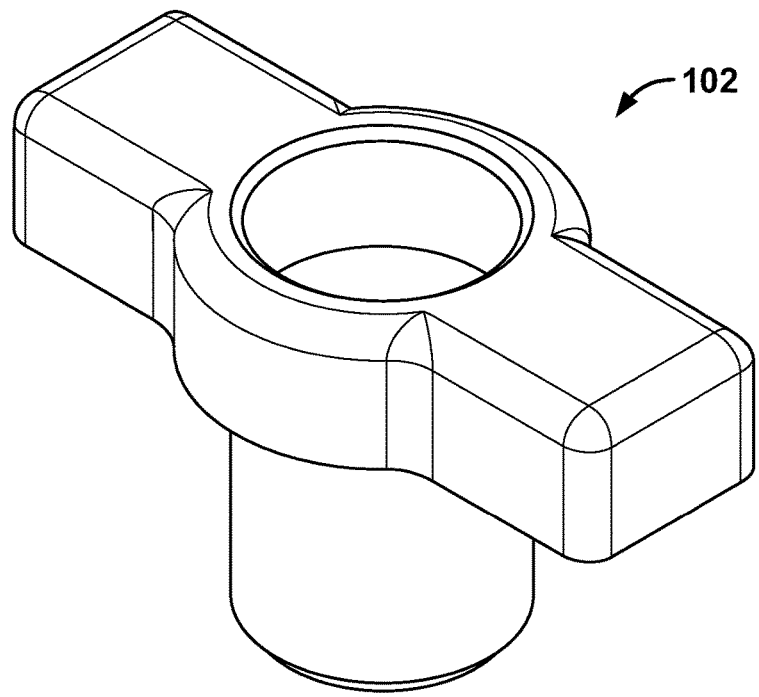
FIG. 17 illustrates an isometric view of an alternative embodiment, for example, including an alternative base component.
Figure 18:
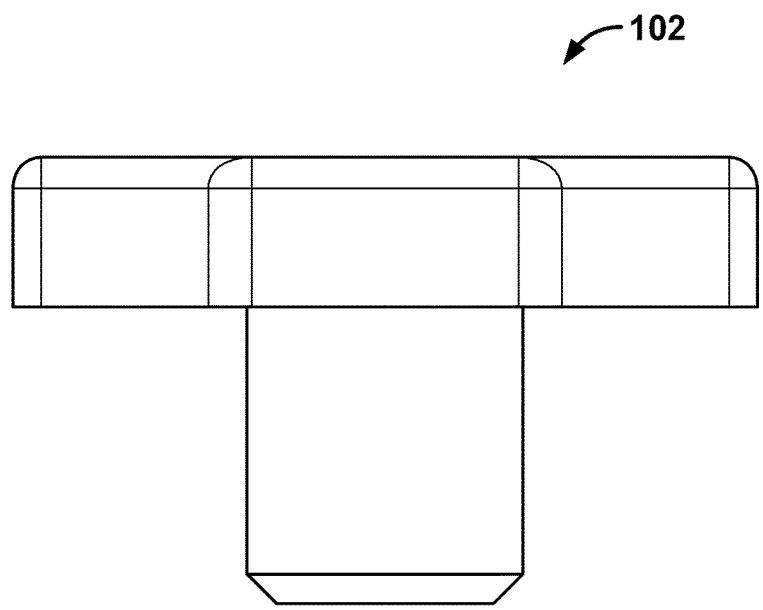
FIG. 18 illustrates a front view of an embodiment of FIG. 17.
Figure 19:
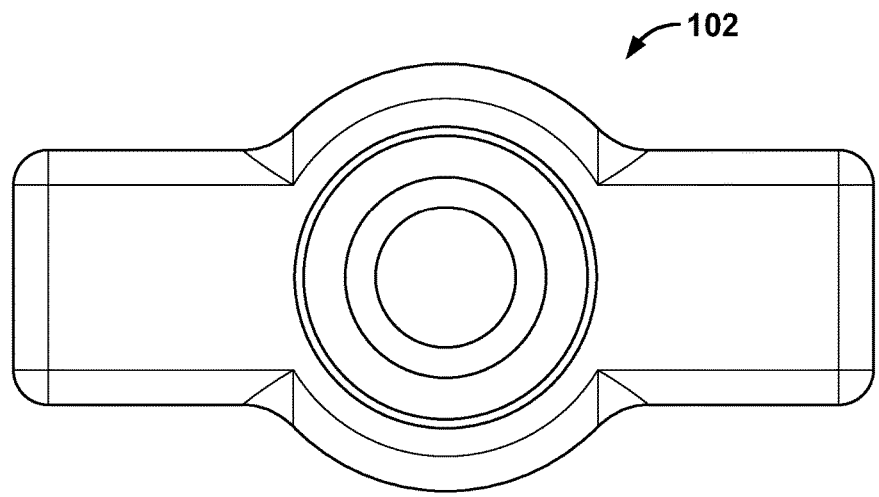
FIG. 19 illustrates a top view of an embodiment of FIG. 17.
Figure 20:
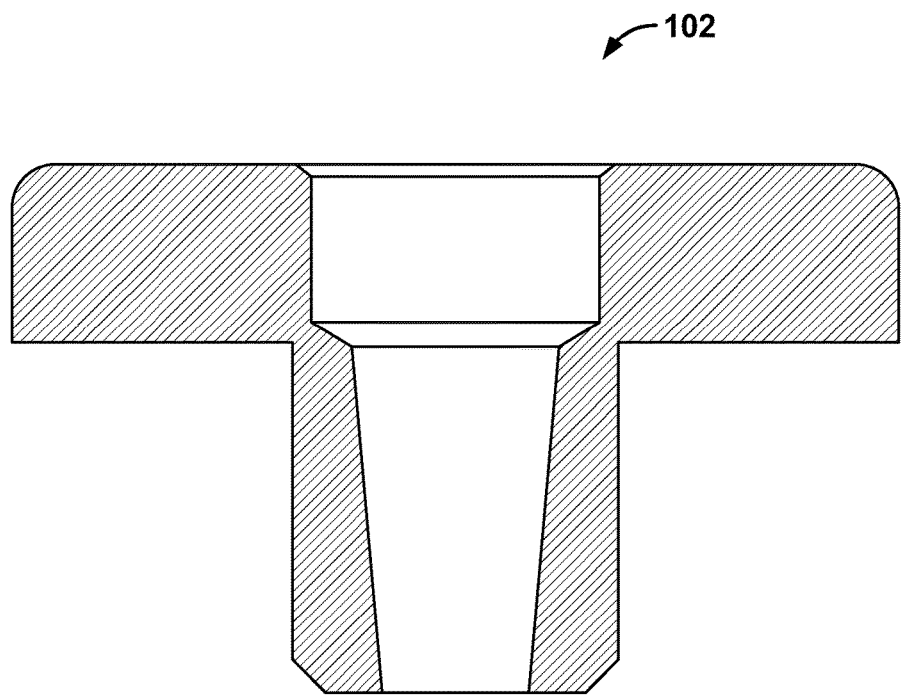
FIG. 20 illustrates a front section view of an embodiment of FIG. 17, for example, including a passage with two or more tapers and/or diameters.
Figure 21:
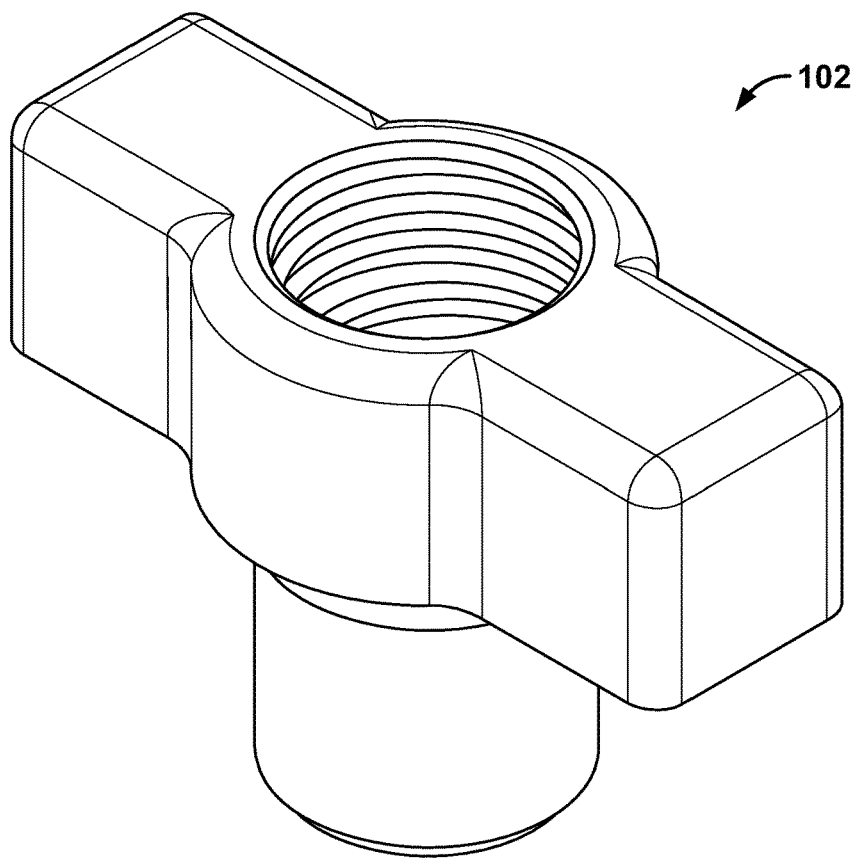
FIG. 21 illustrates an isometric view of an alternative embodiment, for example, including an alternative base component.
Figure 22:
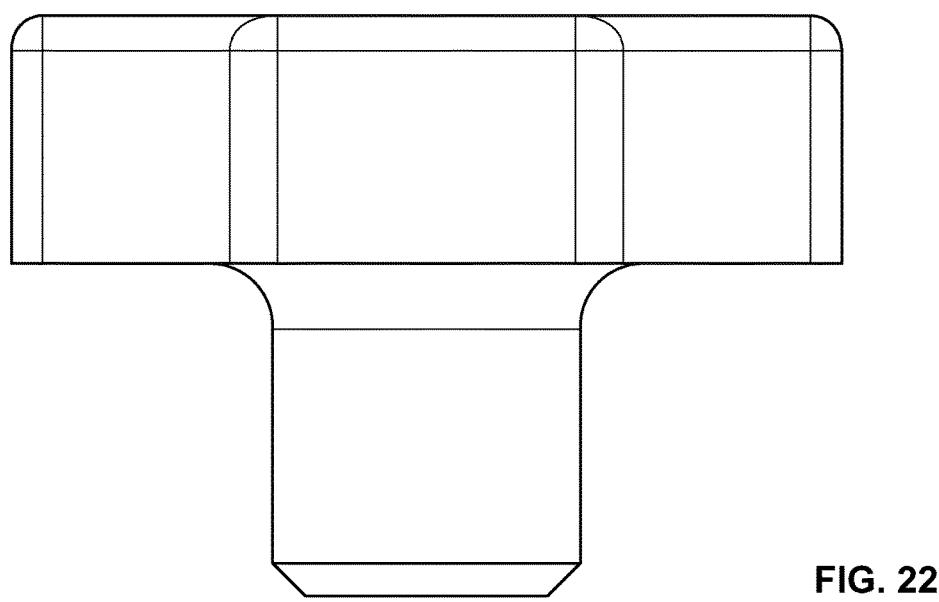
FIG. 22 illustrates a front view of an embodiment of FIG. 21.
Figure 23:
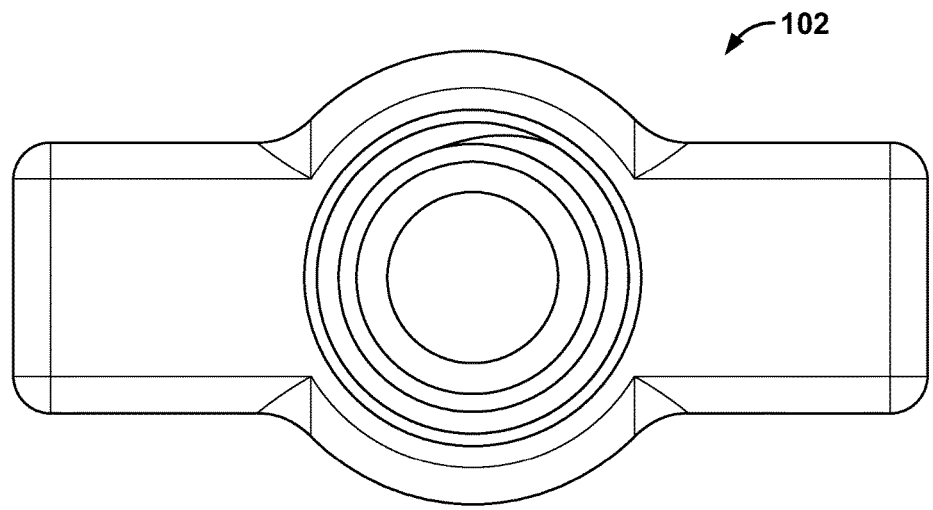
FIG. 23 illustrates a top view of an embodiment of FIG. 21.
Figure 24:
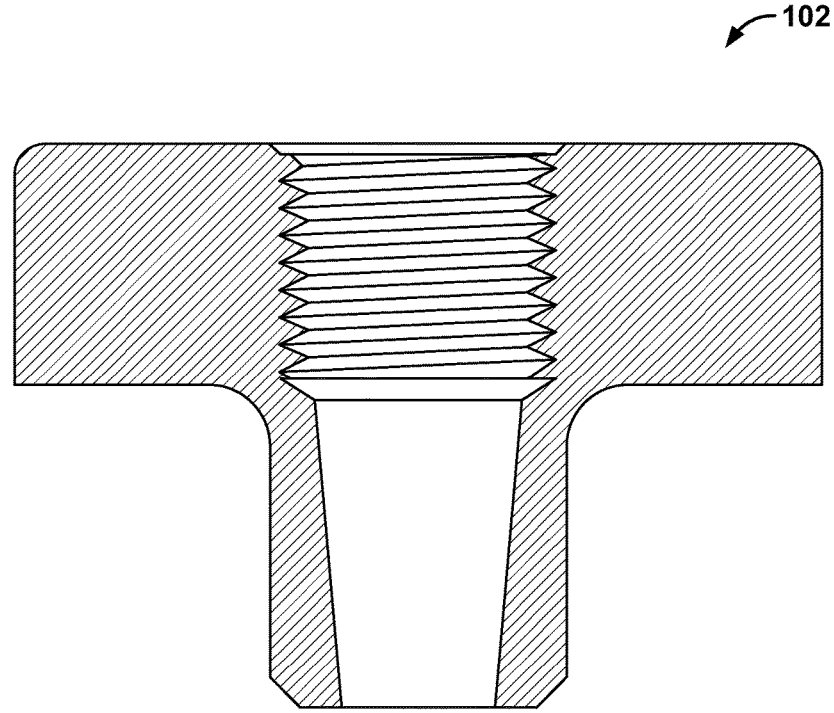
FIG. 24 illustrates a front section view of the embodiment of FIG. 21, for example, including an internal attachment feature.

Insert component 104 may be a solid structure or include a passage through all or any portion of its length. The passage may be centrally located or offset (not shown). (FIGS. 9-12). The passage of insert component 104 may extend through all or a portion (shown) of insert component 104. (FIG. 12). The passage of insert component 104 may be angled with respect to a longitudinal axis of insert component 104. The passage may be smooth, threaded (shown), ringed, undercut, notched, stepped, textured, or drilled. (FIGS. 9, 11, and 12). A lower portion of the passage may be flat or pointed, for example, from a tip of a drill (FIG. 12). The passage of insert component 104 may be configured for insertion and/or removal of insert component 104 relative to body tissue. The passage of insert component 104 may be used as an attachment feature for insertion and/or removal instrumentation. For example, a screw tipped instrument may be driven into the passage of insert component 104 until the instrument contacts the lower portion of the passage of insert component 104, then further rotation of the instrument may rotate insert component 104 thereby allowing it to loosen with respect to elongate member 106 and be removed from the body tissue.

In another embodiment, elongate member 106 may run through the passage in base component 102 and/or insert component 104. (FIGS. 13-16). In use, base component 102 may be urged along elongate member 106 to achieve the desired tension and/or location with respect to the body tissue. Then, insert component 104 may then be positioned over the trailing end of elongate member 106 and urged into base component 102.

A leading end of insert component 104 may be configured to fit into the tapered passage of base component 102. (FIG. 16) Base component 102 and/or insert component 104 may be configured for a press-fit. Alternatively, an externally threaded insert component 104 may screw into an internally threaded base component 102. In use, insert component 104 may be advanced into base component 102 while the leading end of insert component 104 may be forced by the tapered passage of base component 102, thereby pinching elongate member 106 to secure elongate member 106 relative to the body tissue.

All or any portion of the passage of base component 102 may be stepped. (FIGS. 17-24). The lower portion of the passage of base component 102 may include a tapered angle while the upper portion of the passage of base component 102 may include a substantially constant or fixed diameter. The upper portion of the passage of base component 102 (FIGS. 21-24) may be internally threaded to match the external thread on insert component 104 (FIGS. 25-28). Alternatively, the upper portion of the passage of base component 102 and/or the upper portion of insert component 104 may be unthreaded. Base component 102 may include a head portion 108 of increased thickness and/or a radius interposing body portion 110 and head portion 108. (FIGS. 21-24). Head portion 108 of base component 102 may be of increased thickness, for example, to allow more threads and/or greater contact area.

Figure 25:
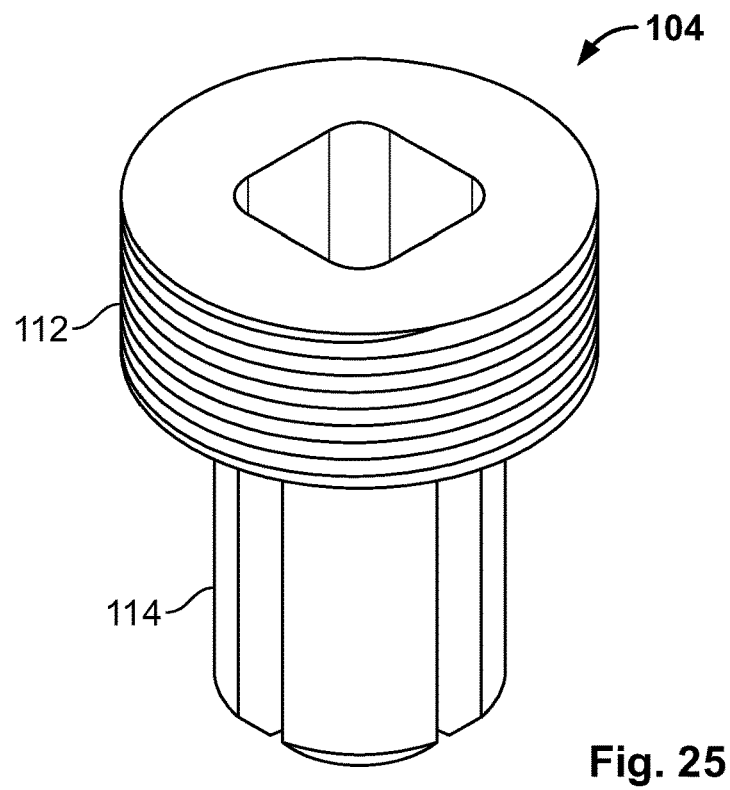
FIG. 25 illustrates an isometric view of an alternative embodiment, for example, including an alternative insert component having a head portion and a body portion.
Figure 26:
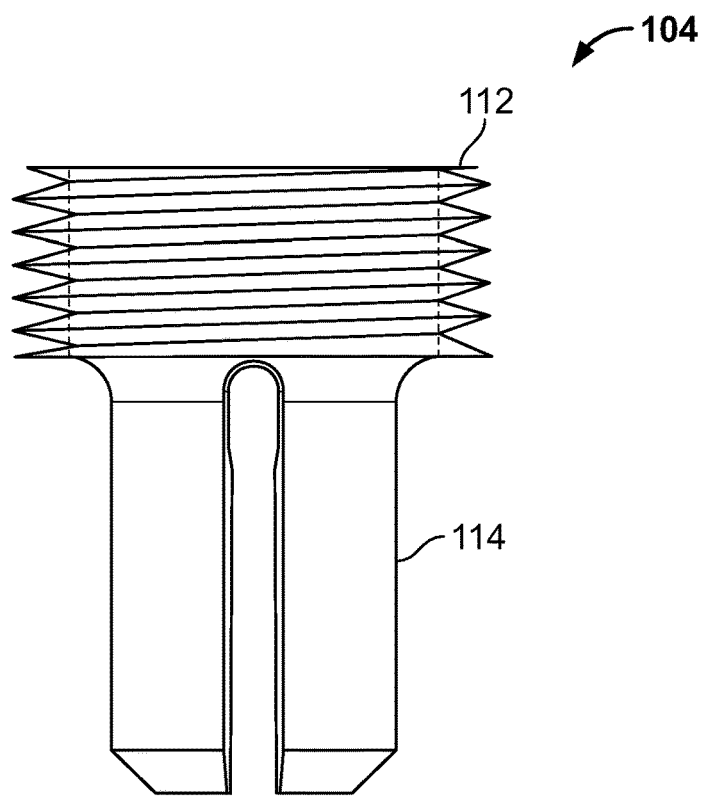
FIG. 26 illustrates a front view of the embodiment of FIG. 25.
Figure 27:
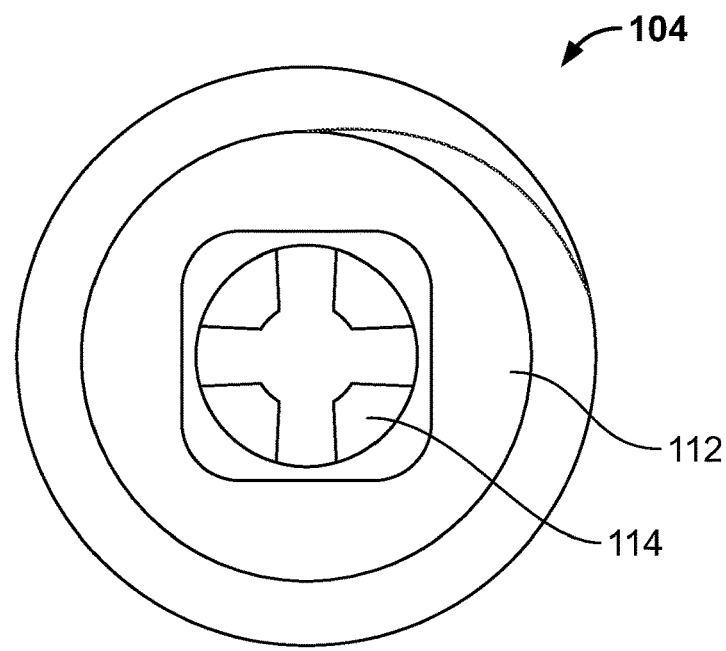
FIG. 27 illustrates a top view of an embodiment of FIG. 25.
Figure 28:
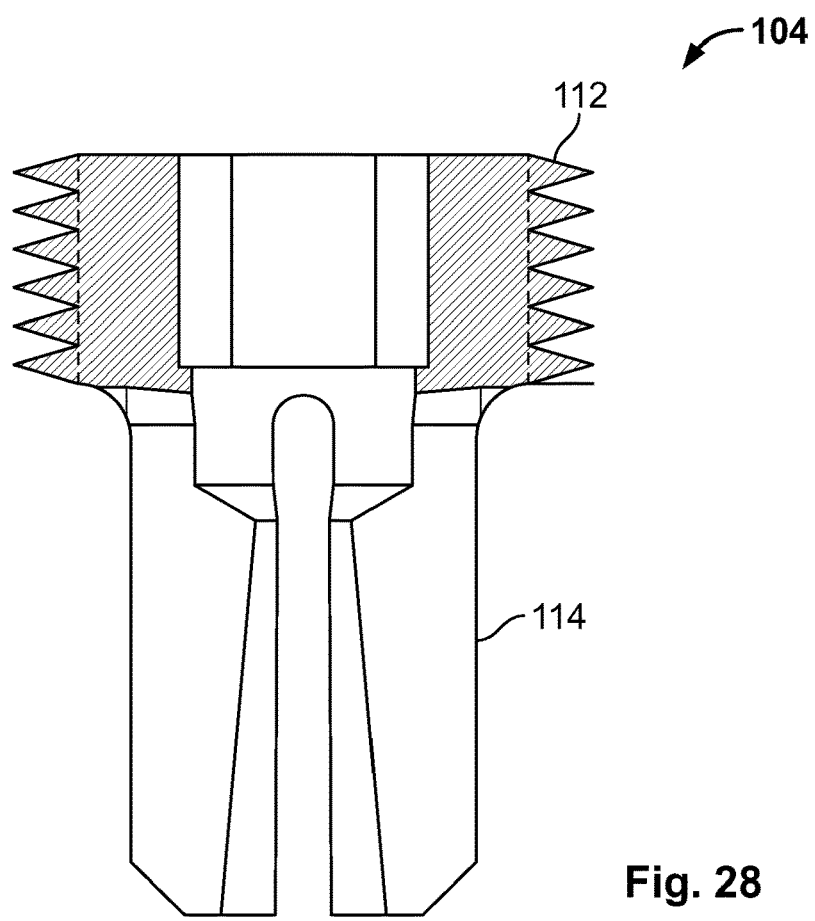
FIG. 28 illustrates a front section view of an embodiment of FIG. 25.
Figure 29:
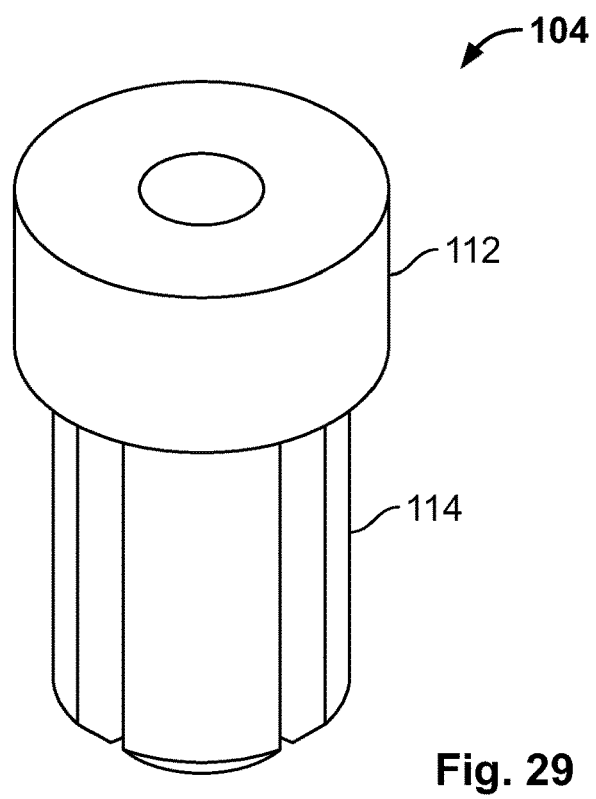
FIG. 29 illustrates an isometric view of an alternative embodiment, for example, including an alternative insert component.
Figure 30:
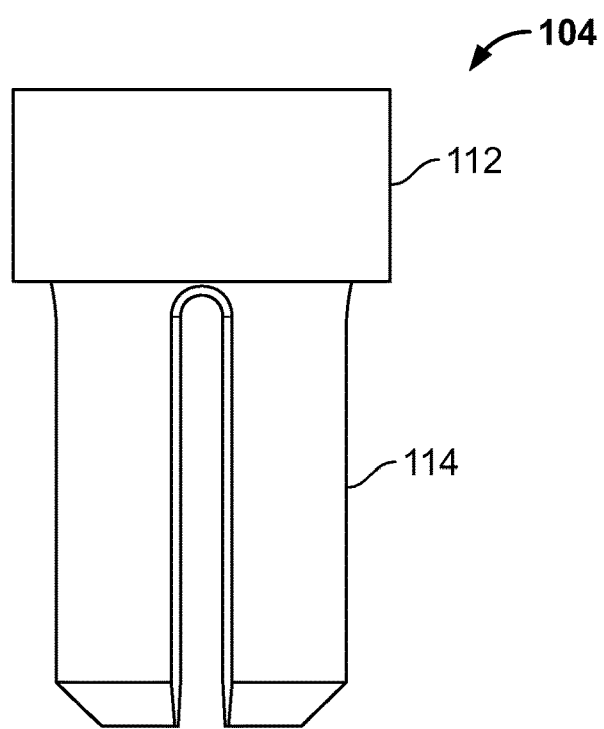
FIG. 30 illustrates a front view of an embodiment of FIG. 29.
Figure 31:
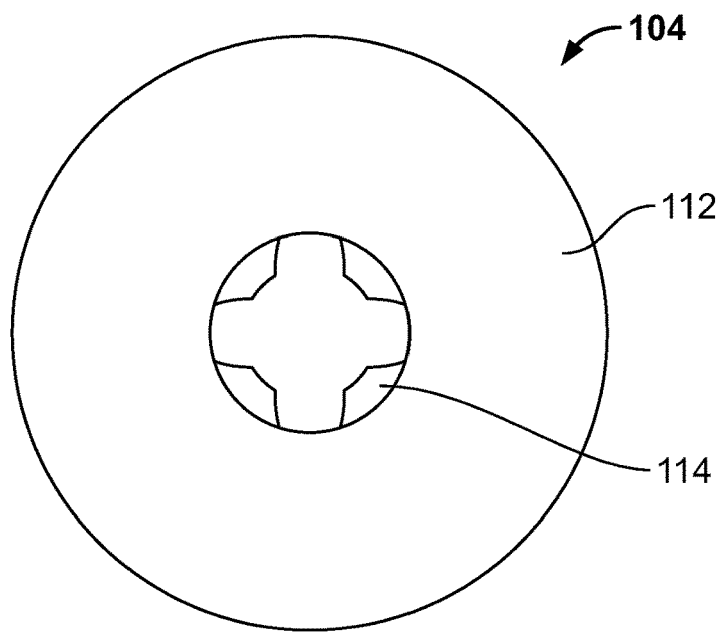
FIG. 31 illustrates a top view of an embodiment of FIG. 29.

Insert component 104 may include head portion 112 and body portion 114. (FIGS. 25-28). Head portion 112 and/or body portion 114 may be cylindrical (shown) or any other shape disclosed herein. Head portion 108 may include an external thread. The thread may be configured to mate with the internal thread of base component 102. Head portion 108 may also include a recess, for example, configured to receive a drive instrument to screw insert component 104 into base component 102. (FIGS. 25 and 27). The cross-sectional shape of the recess of insert component 104 may be square (shown), triangular, rectangular, pentagonal, hexagonal, or any other curved or polygonal shape to allow insert component 104 to be driven with an instrument. Insert component 104 may include a passage through all or any portion of the length of insert component 104 for the passage of elongate member 106. The passage may be centered or offset (not shown) with respect to a longitudinal axis of insert component 104. (FIG. 28).

Body portion 114 of insert component 104 may be divided into projections that may be interposed by slits. (FIG. 25-36). Body portion 114 may be configured to flex or bend with respect to head portion 112 of the insert. In use, as insert component 104 is urged into base component 102, the tapered passage in base component 102 may drive these projections radially inward to apply a force against the elongate member 106 that is positioned through insert component 104 or between insert component 104 and base component 102. Body portion 114 of insert component 104 may be divided into two, three, four (shown), five, six or more projections. The projections may be of equal or varying spacing, length, and/or width.

Figure 32:
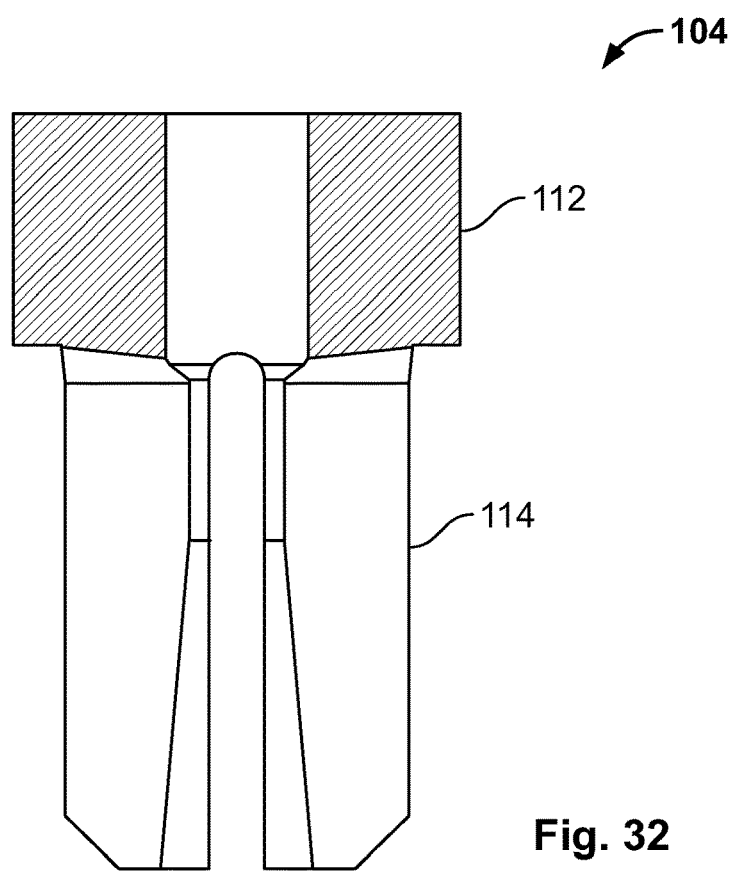
FIG. 32 illustrates a front section view of an embodiment of FIG. 29.

The passage of insert component 104 may include a tapered, chamfered, or radiused surface between head portion 112 and body portion 114. (FIG. 32). The taper angle of insert component 104 may substantially match the taper angle of base component 102. The taper angle of insert component 104 with the taper angle of base component 102 may be configured to increase the contact length between insert component 104 and elongate member 106, for example, to improve the locking strength of fixation device 100. In use, the passage of head portion 112 and body portion 114 of insert component 104 may allow the projections of insert component 104 to flex radially inward and collapse, thereby securing elongate member 106 relative to base component 102.

Another embodiment of insert component 104 may be pressed into base component 102 with or without a passage in head portion 112. (FIGS. 29-32). Insert component 104 may or may not have external threads, for example, on head portion 112. The tapered passage between the projections of body portion 114 may extend all or a portion of the distance from base portion 114 of insert component 104. The cross-sectional shape of base portion 114 of insert component 104 may be circular (shown), triangular, square, rectangular, pentagonal, hexagonal, or any other curved or polygonal shape.

Figure 33:
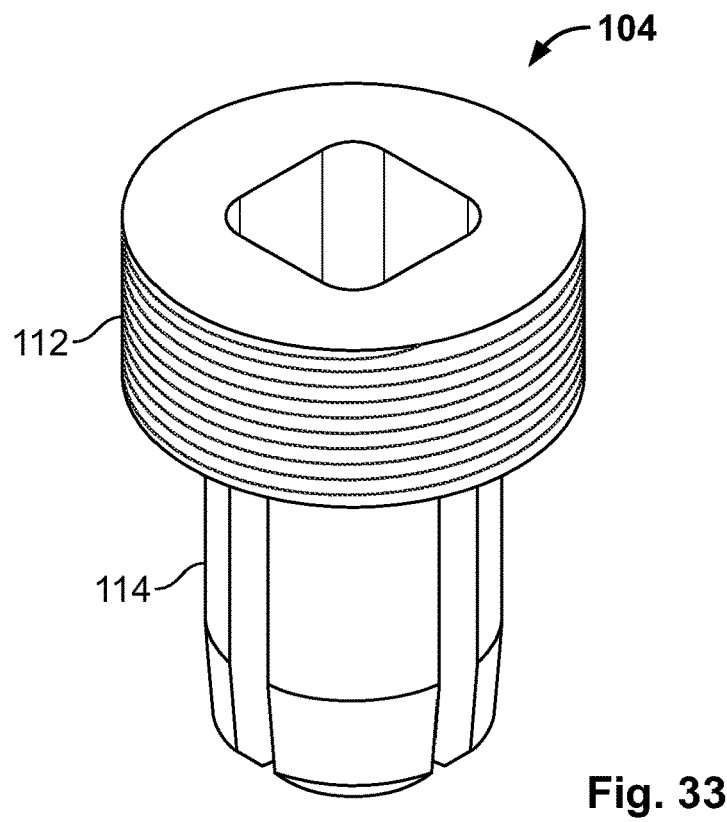
FIG. 33 illustrates an isometric view of an alternative embodiment, for example, including, an alternative insert component of the fixation device.
Figure 34:
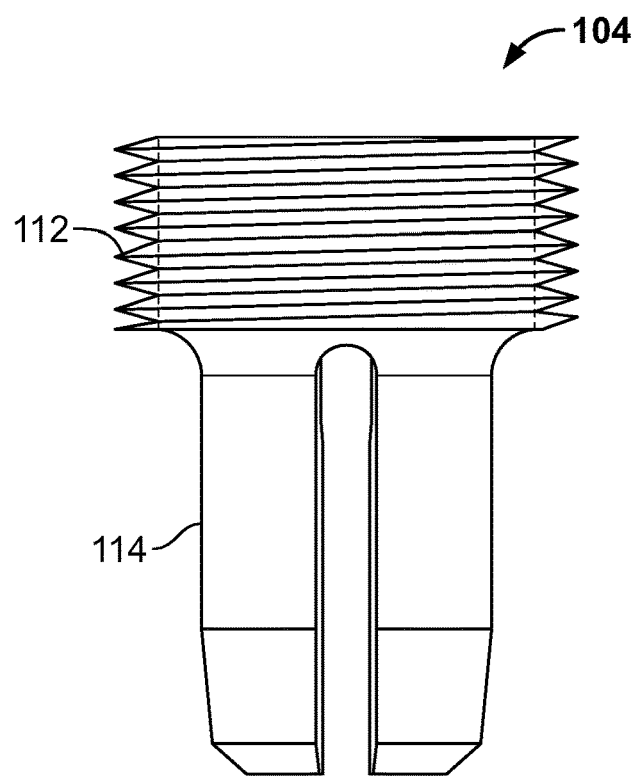
FIG. 34 illustrates a front view of an embodiment of FIG. 33.
Figure 35:
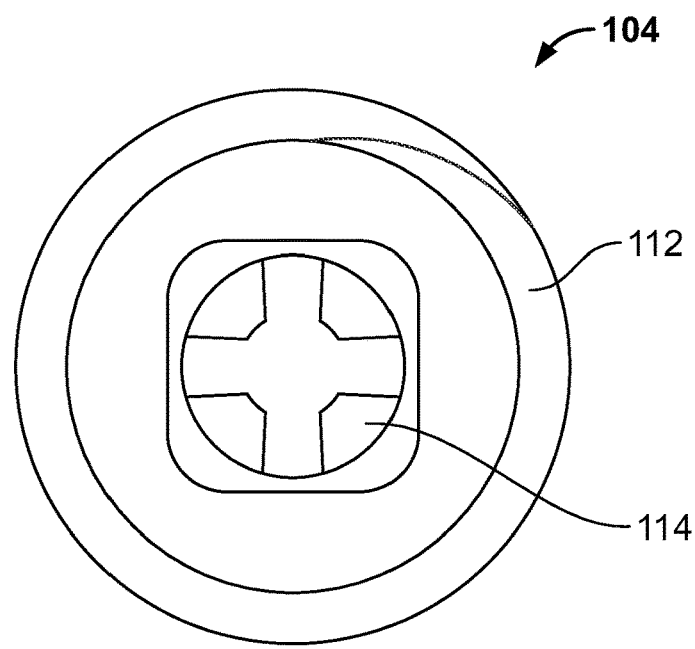
FIG. 35 illustrates a top view of an embodiment of FIG. 33.
Figure 36:
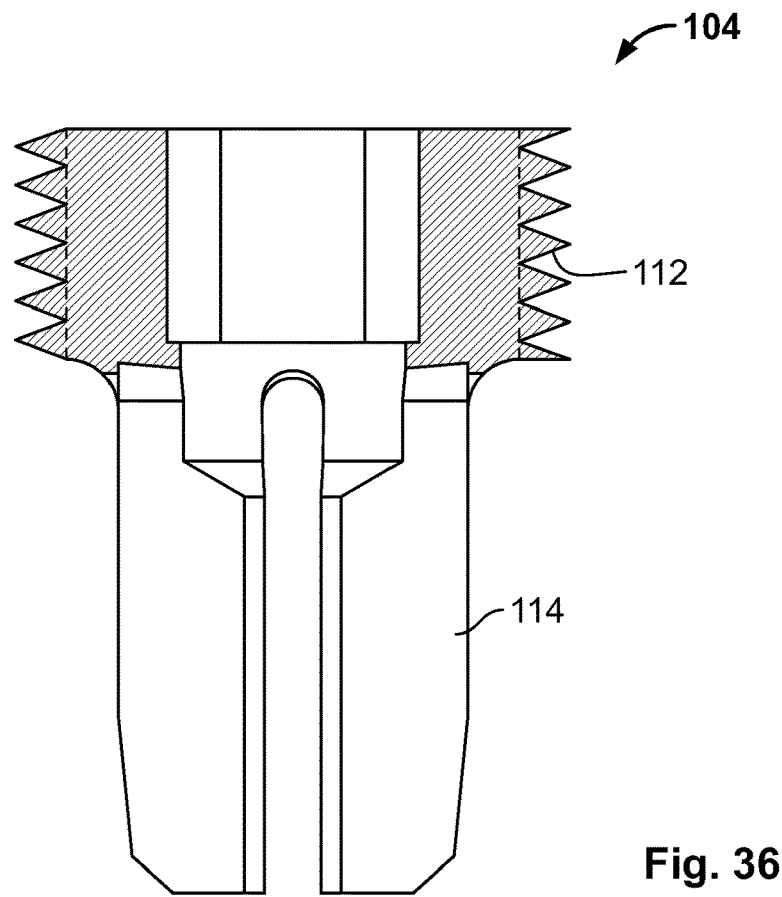
FIG. 36 illustrates a front section view of an embodiment of FIG. 33, for example, including an external attachment feature.

Additional embodiments of insert component 104 may have various taper angles and threaded areas. (FIGS. 33-36). The outer surfaces and/or inner surfaces of the projections of body portion 114 may have two or more taper angles, for example, to facilitate insertion into base component 102 and/or improve locking relative to elongate member 106. (FIG. 33). Insert component 104 may have an externally or internally threaded head portion 112. The passage through the projections of body portion 110 may or may not be tapered. The taper may be configured to increase a contact area with elongated member 106, for example, when the projections may be forced radially inward when being driven into a tapered passage in the base component 102.

Figure 37:
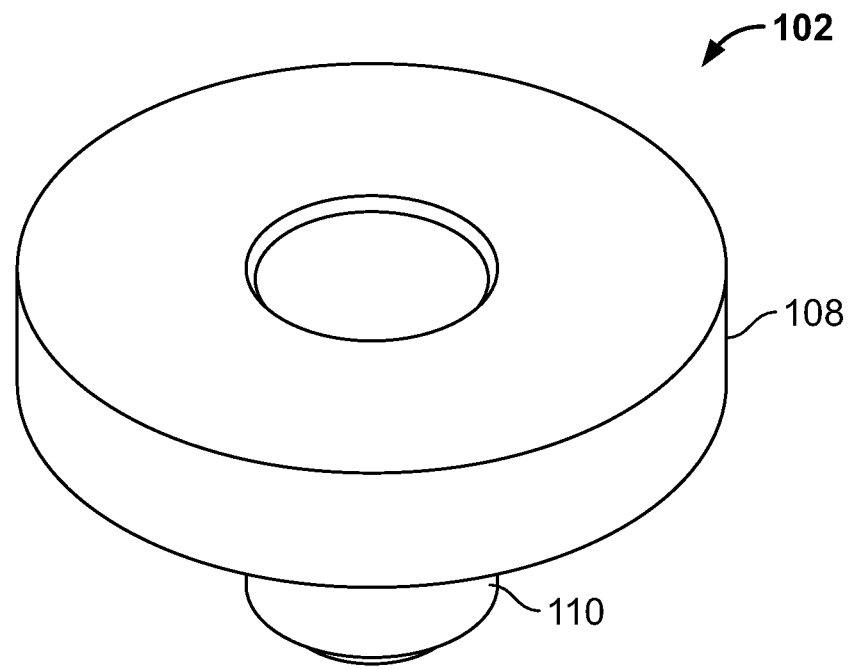
FIG. 37 illustrates an isometric view of an alternative embodiment, for example, including an alternative base component.
Figure 38:
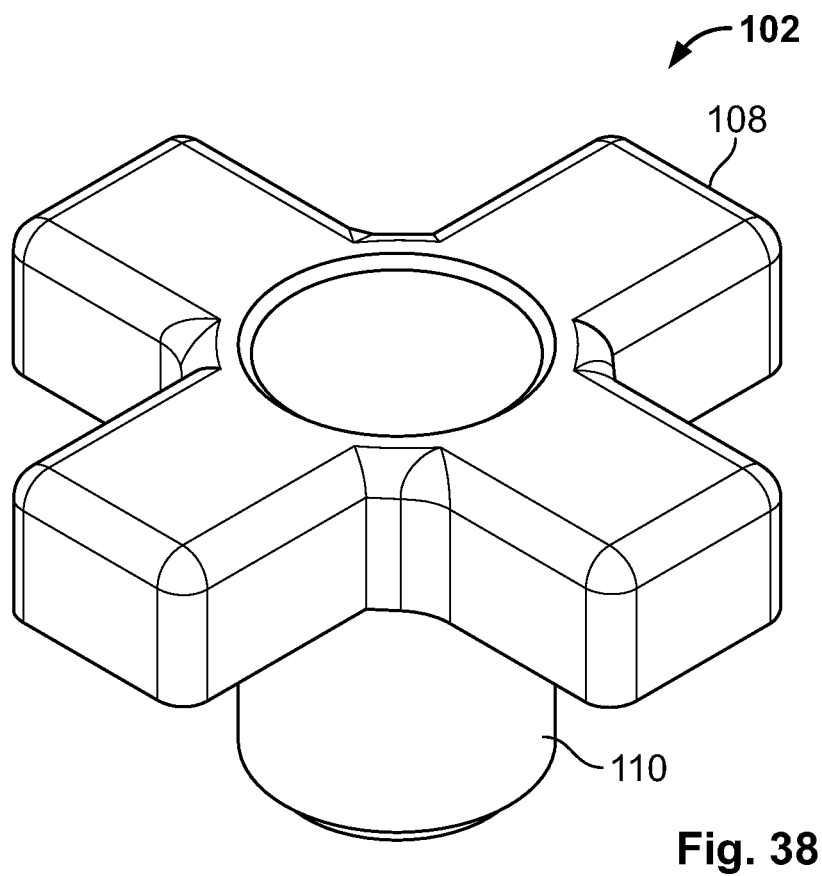
FIG. 38 illustrates an isometric view of an alternative embodiment, for example, including another alternative base component.
Figure 39:
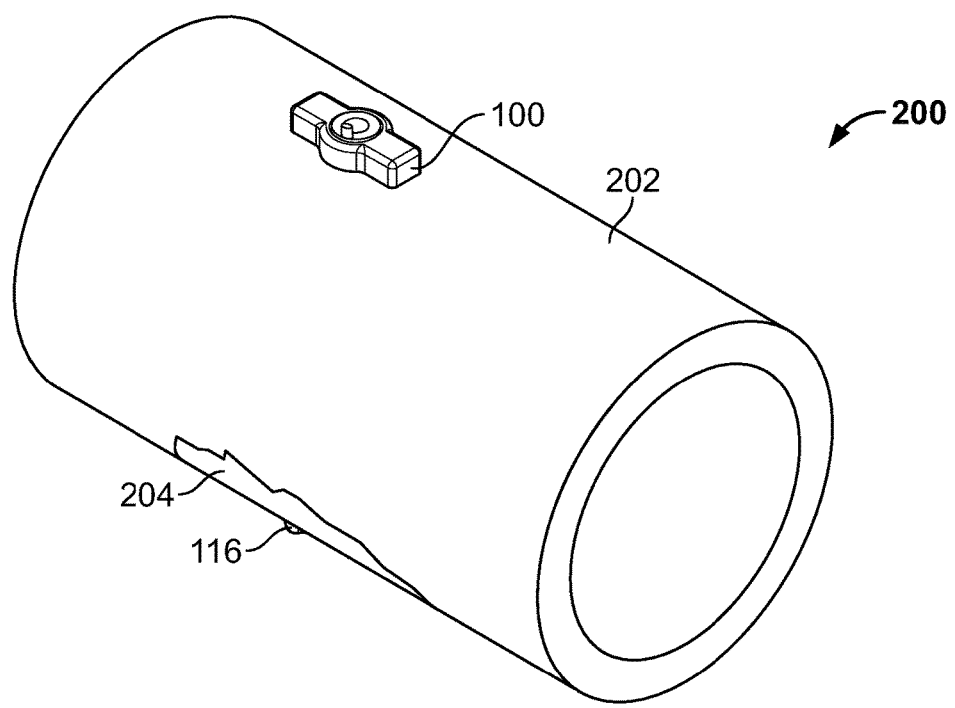
FIG. 39 illustrates an isometric schematic of an embodiment, for example positioned with respect to a tissue fracture.
Figure 40:
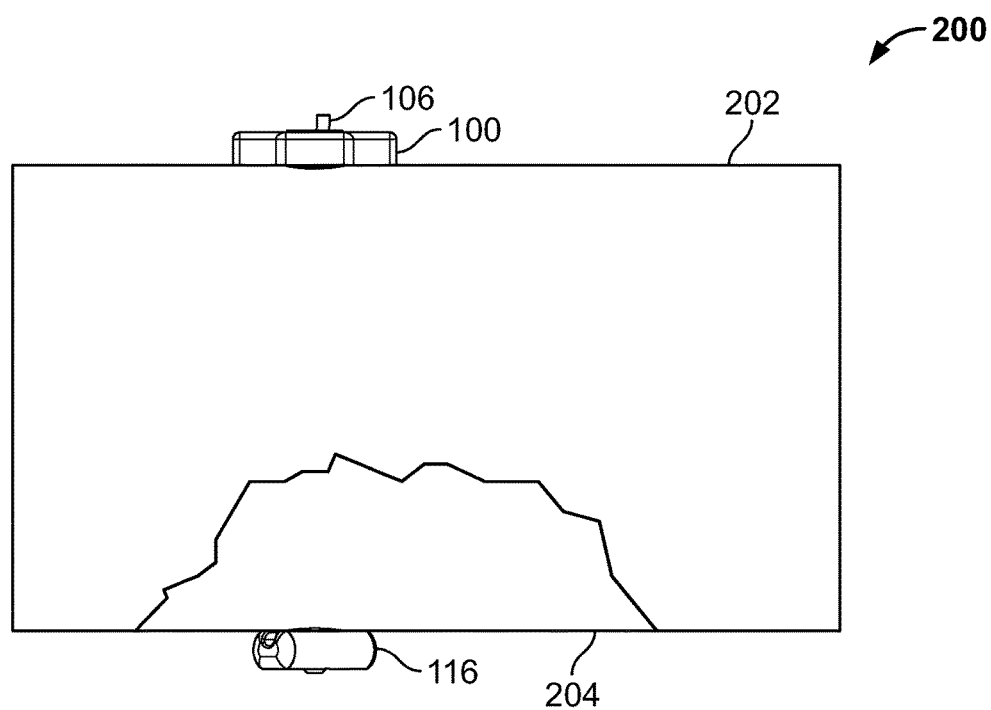
FIG. 40 illustrates a side view of an embodiment of FIG. 39.
Figure 41:
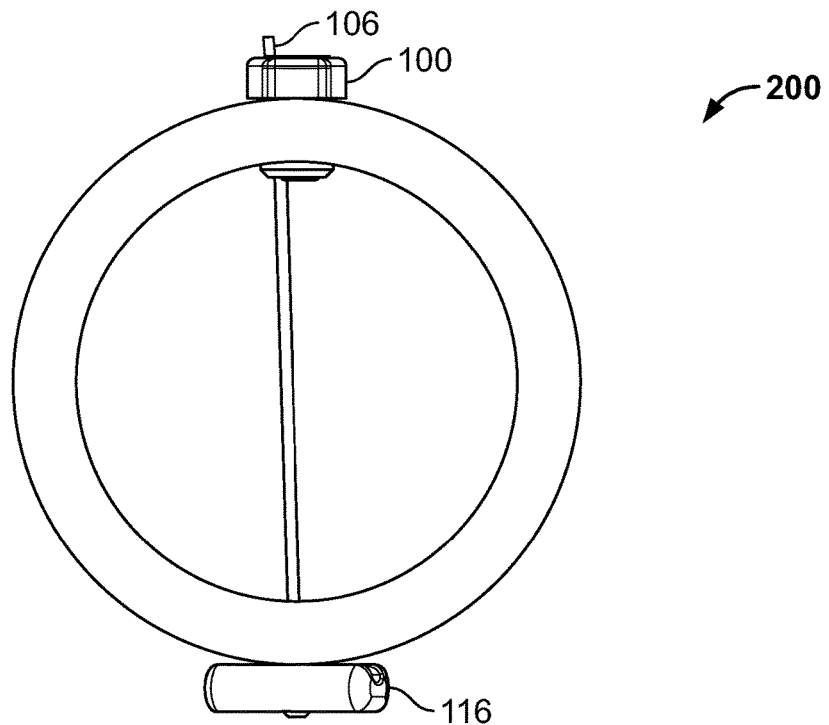
FIG. 41 illustrates another side view of an embodiment of FIG. 39.
Figure 42:
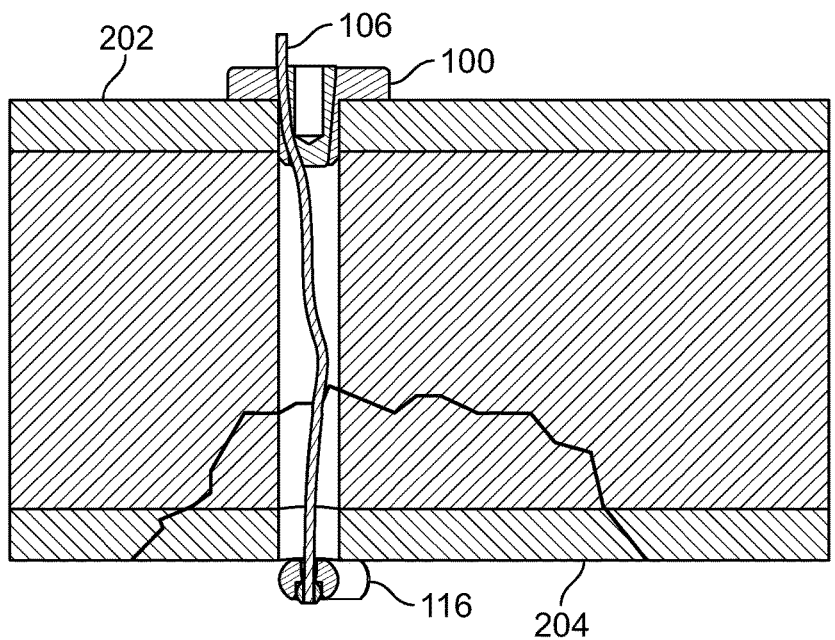
FIG. 42 illustrates a side section view of an embodiment of FIG. 39.

Base component 102 may have any shape. Base component 102 may have a substantially symmetric or solid head portion 108, for example circular (shown) or any other shape disclosed herein. (FIG. 37). Alternatively, base component 102 may include any number of tabs, for example one, two, three, four (shown), or more. The tabs may have any dimensions or spacing, for example equal (shown), different, or varying. (FIG. 38).

Referring to FIGS. 39-42, one or more fixation devices 100 may be used. Fixation device 100 may include fastener 116. In use, fixation device 100 may be used to secure elongate member 106 to repair a fracture of hard and/or soft tissue 200. Tissue 200 may include tissue 202 and tissue 204, for example including at least two bone fragments. Tissues 202 and 204 may be urged toward each other with a stabilizing instrument, for example a clamp.

To secure tissue 202 and tissue 204 relative to each other, a cutting instrument, for example a cannulated drill device including an inner drill or K-wire disposed in an exterior cutting sleeve, may be urged into and/or through tissues 202 and 204 from a proximal area to a distal area thereby creating a passage. The inner drill or K-wire and exterior cutting sleeve may be interlocked to simultaneously cut through tissues 202 and 204. Alternatively, the inner drill or K-wire may cut through the fragments before or after the outer sleeve cuts through the fragments.

Next, fastener 116 and elongate member 106 may be deployed. The inner k-wire or drill may be removed while the sleeve is positioned through all or any portion of tissues 202 and 204. Fastener 116, for example an anchor, button, deformable fastener, or any other fixation device, may be connected to elongate member 106 then passed through the sleeve to the distal area. Fastener 116 may include a solid, porous, hard, soft, or deformable material or any other material disclosed herein. Fastener 116 may include a metal, plastic, ceramic, woven, biologic, and/or suture material (i.e. polyethylene). Fastener 116 may be of the same material or different than elongate member 106. Fastener 116 may be rigid, flexible, and/or deformable. Fastener 116 may be comprised of a single or one or more components. Fastener 116 may be positioned through the sleeve by pushing fastener 116 with a pushrod or directly urged with a rigid elongate member 106. Fastener 116 may be positioned through all or any portion of the sleeve, tissue 202, tissue 204, and/or soft tissue adjacent tissue 202 and/or 204. Upon positioning of fastener 116, elongate member 106 may be tensioned thereby pulling fastener 116 against the distal area to reduce the fracture. If the fracture is an avulsion fracture with soft tissue attached to a bone fragment, fastener 116 may be positioned through tissues 202, tissue 204, and the soft tissue attached to the tissues 202 and 204. Tensioning elongate member 106 relative to fastener anchor 116 secures tissues 202 and 204 and the attached soft tissue.

Then, proximal portion of elongate member 106 may be secured, for example, with fixation device 100 or with a knot. The sleeve may be removed from the tissues 202 and 204. Base component 102 may be placed over elongate member 106 near the proximal area and urged toward tissue 202. Body portion 110 of base component 102 may be placed into the tissue passage while head portion 108 of base component 102 remains on the surface of tissue 202. Elongate member 106 may be tensioned by the user manually or with a tensioning instrument to keep tissues 202 and 204 compressed. Insert component 104 may be urged into base component 102 while elongate member 106 remains tensioned. After insert component 104 of fixation device 100 is sufficiently secured to base component 102, elongate member 106 may be secured thereby reducing separation of tissues 202 and 204. Any excess length of elongate member material may be cut and/or removed.

Figure 44:
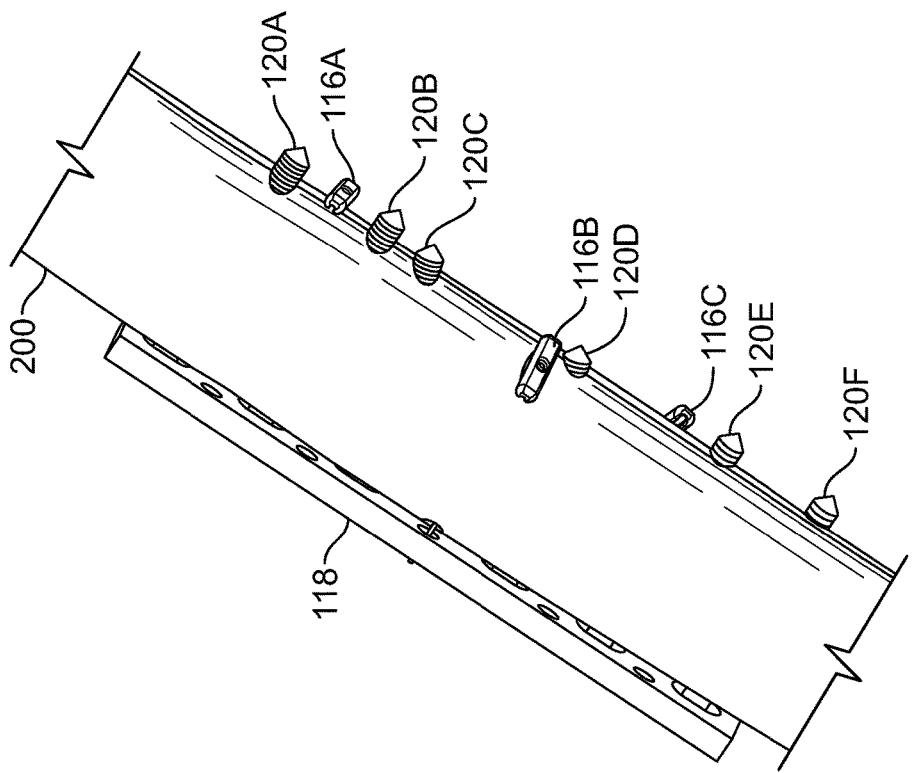
FIG. 44 illustrates a back isometric view of an embodiment of FIG. 43.
Figure 43:
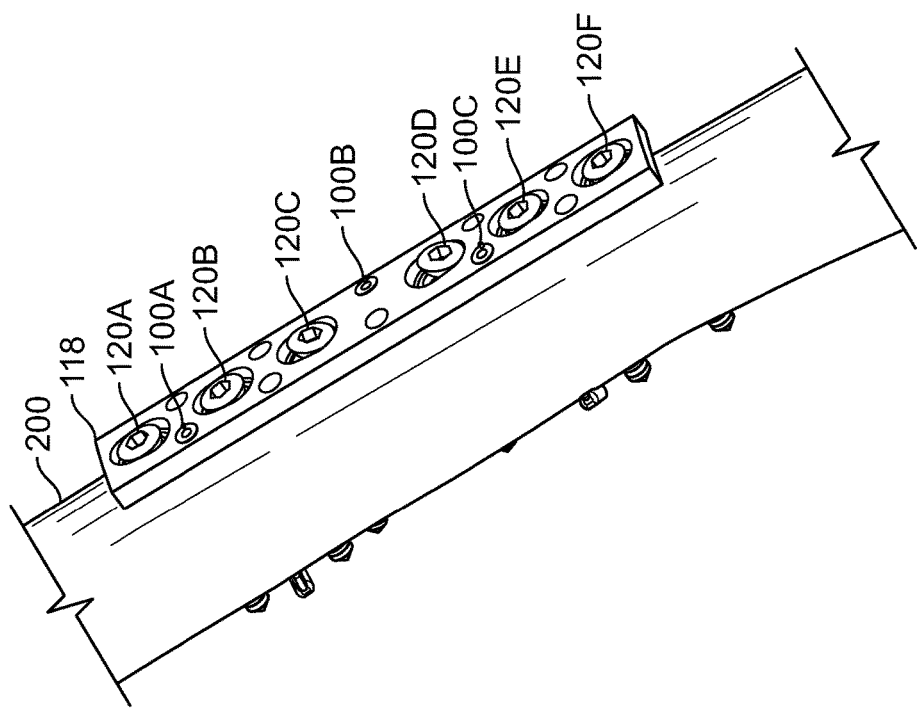
FIG. 43 illustrates a front isometric view of an embodiment of the present disclosure, for example, including a plate and screws positioned with respect to a tissue fracture.
Figure 45:
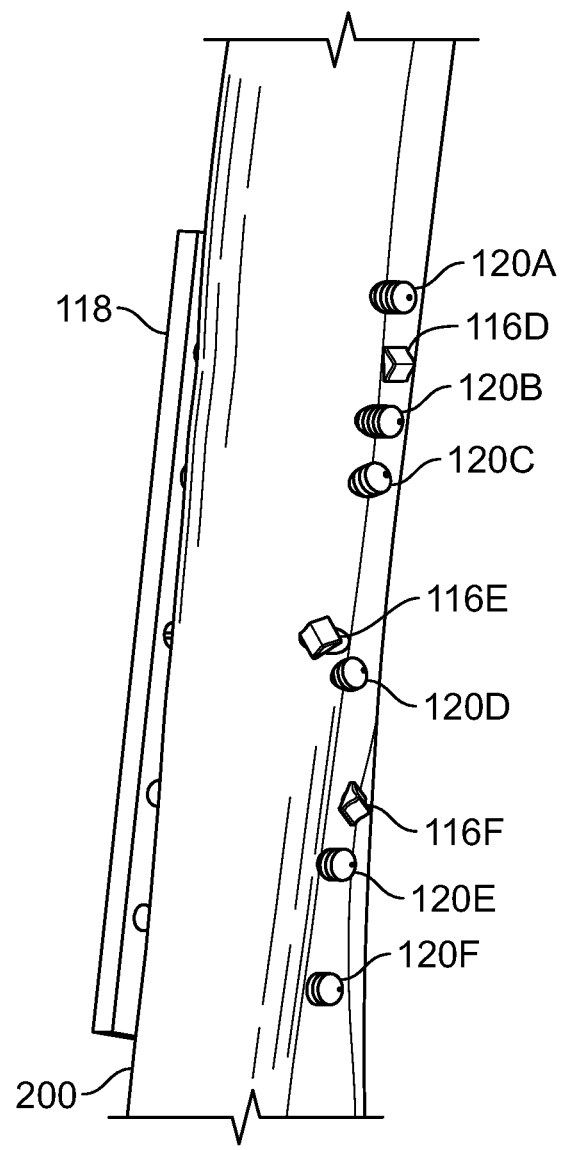
FIG. 45 illustrates a back isometric view of an alternative embodiment of FIG. 43.

With reference to FIGS. 43-45, fixation device 100 may be used in conjunction with other implants, for example one or more plates 118 and/or screws 120. Plates 118 and screws 120 may be used to secure a bone fracture. For example, larger fragments (i.e. hard tissue such as bone) of the fracture may be secured with plate 118 and screws 120 while elongate member 106 and fixation device 100 may be used to reduce separation of and secure smaller fragments (i.e. soft tissue and smaller fragments of hard tissue such as bone). Plate 118 may include one or more holes. One or more fasteners 116 connected to elongate member 106 may be passed through a hole in plate 118. Base component 102 of fixation device 100 may then be positioned on or in plate 118, mechanically interlocked into plate 118, or not used if insert component 104 is configured to mechanically interlock with an attachment feature (i.e a hole or keyed surface) in plate 118. Plate 118 may have additional holes in the top or sides, for example, to position the cannulated drill device. Upon passing fastener 116 through the holes of plate 118, elongate member 106 may be tensioned and secured with insert component 104. Insert component 104 may mechanically interlock with base component 102 or directly into plate 118 without base component 102. One or more fastener 116 may include a solid button configured to toggle (FIG. 44) and/or a soft, flexible, or deformable material (FIG. 45).

Figure 47:
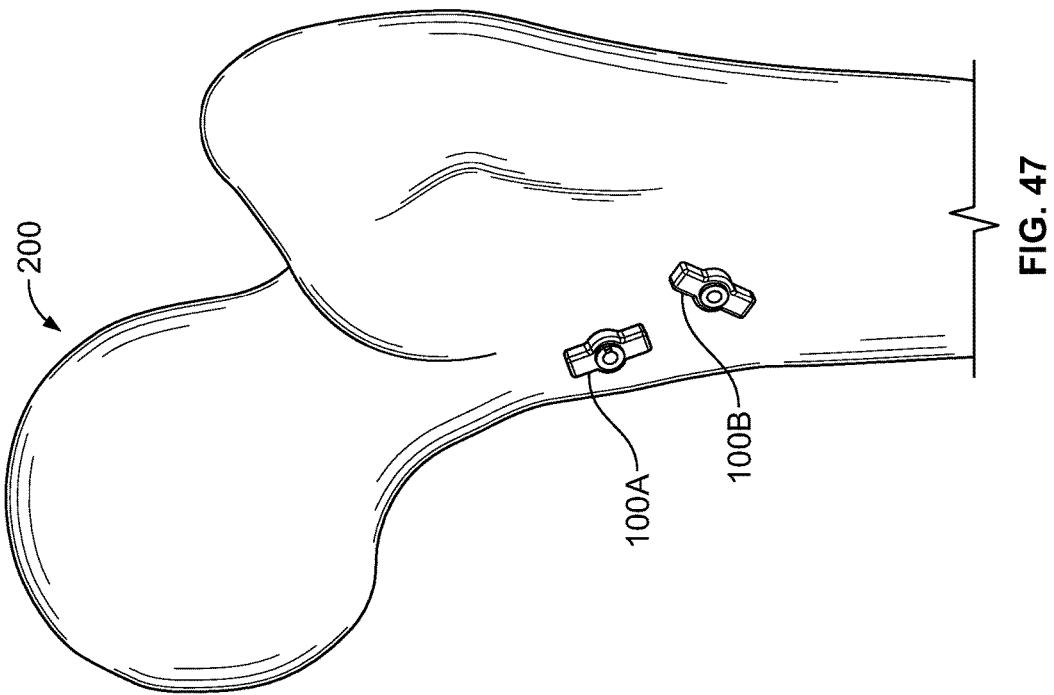
FIG. 47 illustrates an alternative view of an embodiment of FIG. 46, for example, including one or more fixation devices.
Figure 46:
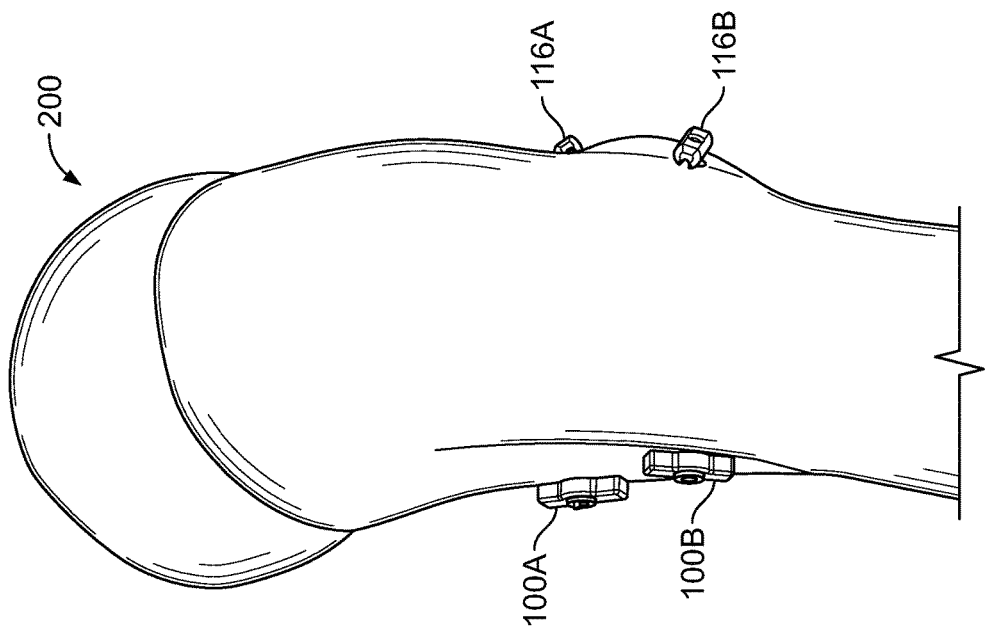
FIG. 46 illustrates an isometric view of an embodiment, for example, including repair of a tissue fracture of the lesser trochanter of a femur.
Figure 49:
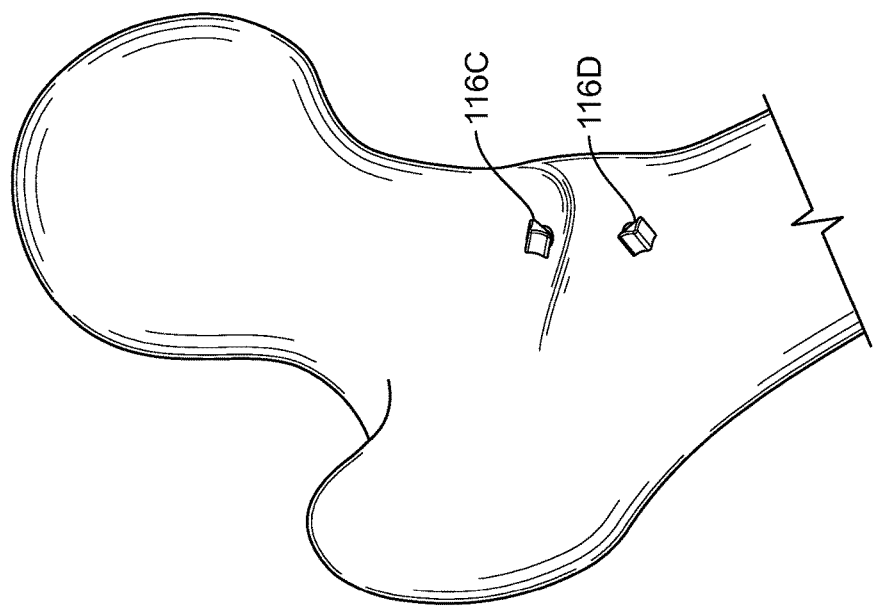
FIG. 49 illustrates an alternative embodiment of FIG. 48, for example, including one or more alternative fasteners.
Figure 48:
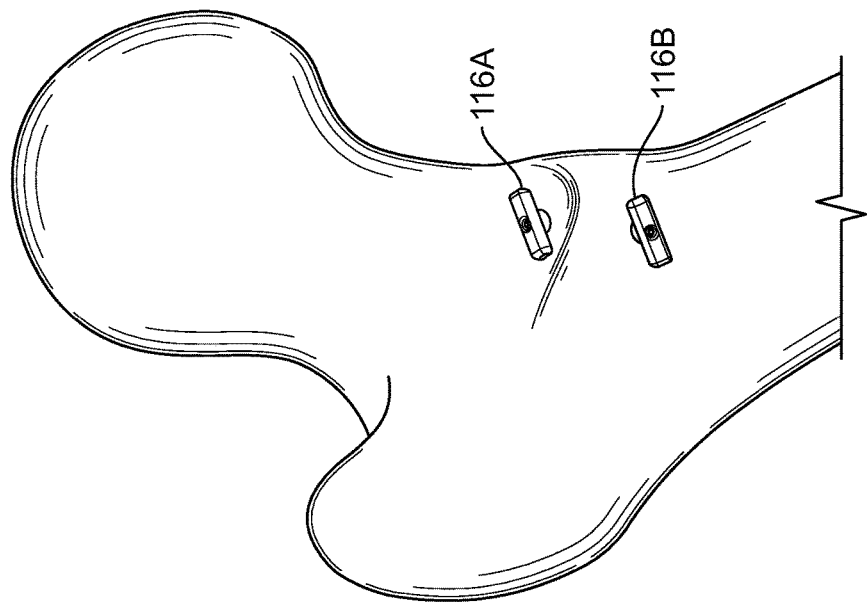
FIG. 48 illustrates an alternative view of an embodiment of FIG. 46, for example including one or more fasteners.

Fixation device 100 may be used for any medical application. In an embodiment, one or more fixation device 100 may be used to repair tissue 200 of a femur, for example a lesser trochanter fracture. (FIGS. 46-49). This type of fracture may be referred to as an avulsion fracture with soft tissue attached to the lesser trochanter. For example, one or more holes may be drilled from an anterior area to a posterior area of the femur through a lesser trochanter area where fasteners 116 may be positioned. (FIG. 46). Elongate member 106 may be tensioned and/or fixation devices 100 may be secured at a proximal portion of elongate member 106. (FIG. 47). One or more fasteners 116 may include a solid button configured to toggle (FIG. 48), soft, flexible, or deformable fasteners (FIG. 49), or any combination thereof.

Figure 51:
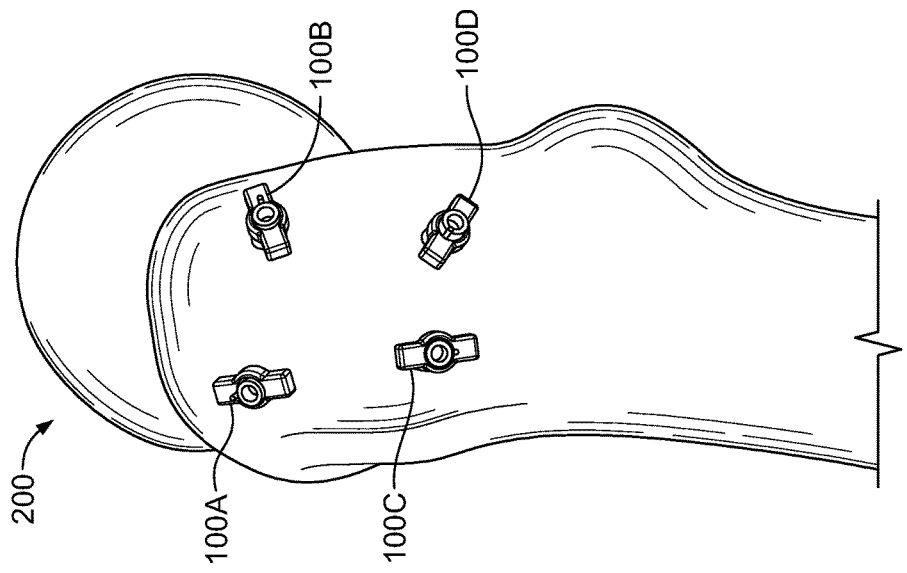
FIG. 51 illustrates an alternative view of an embodiment of FIG. 50, for example, including one or more fixation devices.
Figure 50:
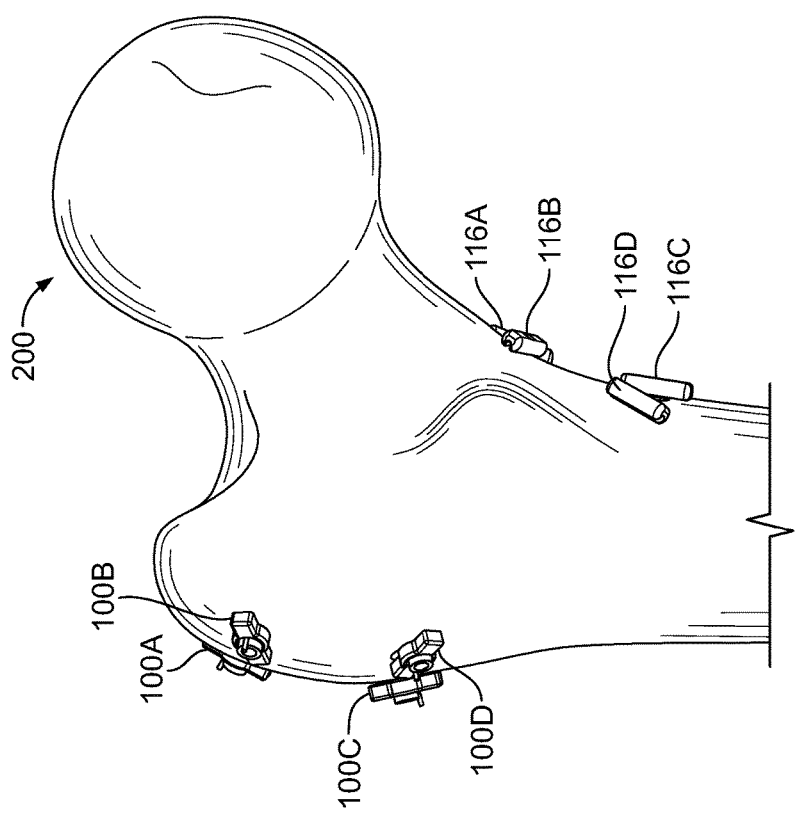
FIG. 50 illustrates an isometric view of an embodiment, for example, including repair of a tissue fracture of the greater trochanter of the femur.
Figure 53:
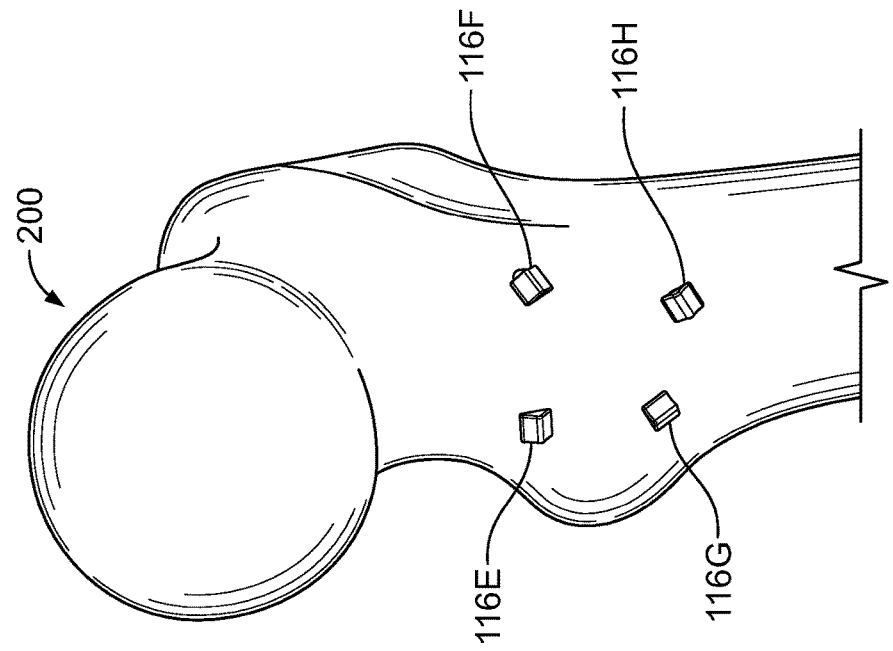
FIG. 53 illustrates an alternative embodiment of FIG. 50, for example, including one or more alternative fasteners.
Figure 52:
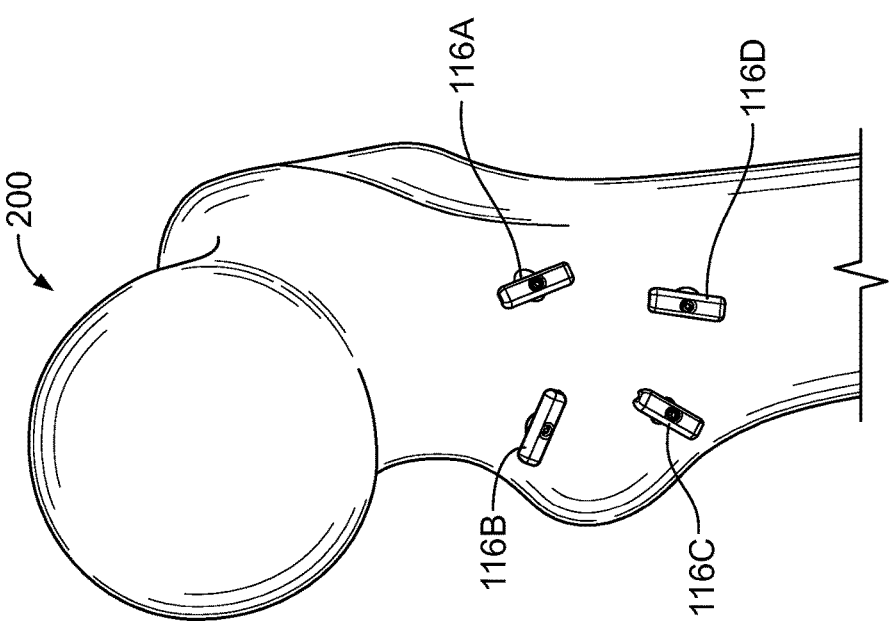
FIG. 52 illustrates an alternative view of an embodiment of FIG. 50, for example, including one or more fasteners.

As another embodiment, one or more fixation device 100 may be used to repair a fracture of tissue 200, for example a greater trochanter fracture of the femur. (FIGS. 50-54). This type of fracture may also be referred to as an avulsion fracture with tissue attached to the greater trochanter. Holes may be drilled into and/or through the greater trochanter to the lesser trochanter for placement of one or more fastener 116. (FIGS. 50-51). Elongate member 106 may be tensioned and/or fixation devices 100 may be placed over the greater trochanter to secure the proximal portion of elongate members 106. (FIG. 51) Fasteners 116 may include solid buttons (FIG. 52), soft, flexible, or deformable fasteners (FIG. 53), or any combination thereof.

Figure 54:
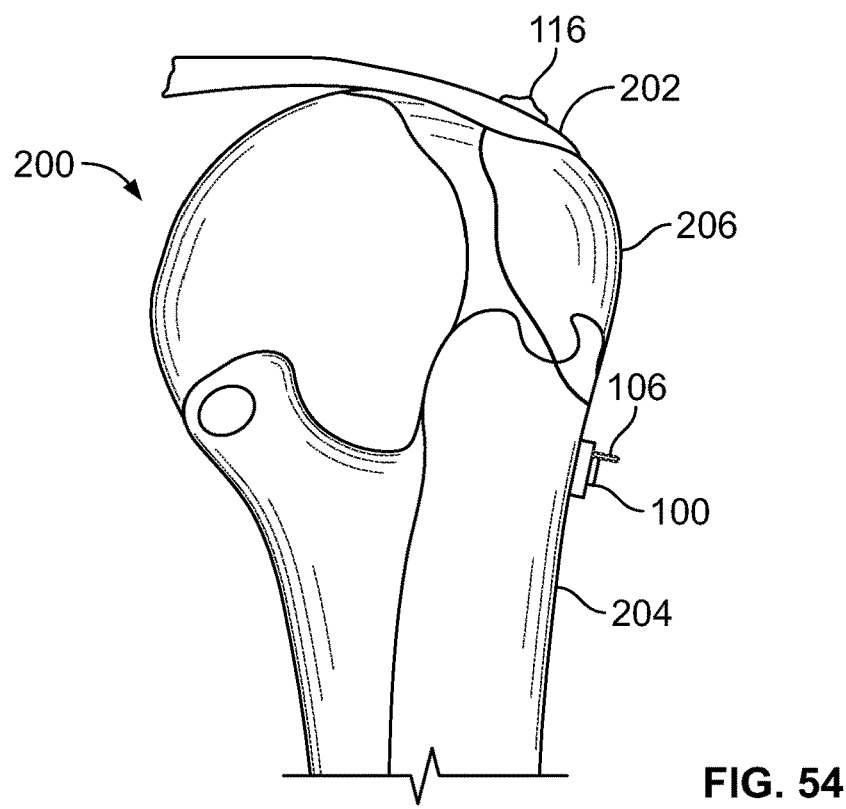
FIG. 54 illustrates an embodiment the present disclosure, for example, including repair of a tissue fracture of the greater tuberosity of the humerus.
Figure 55:
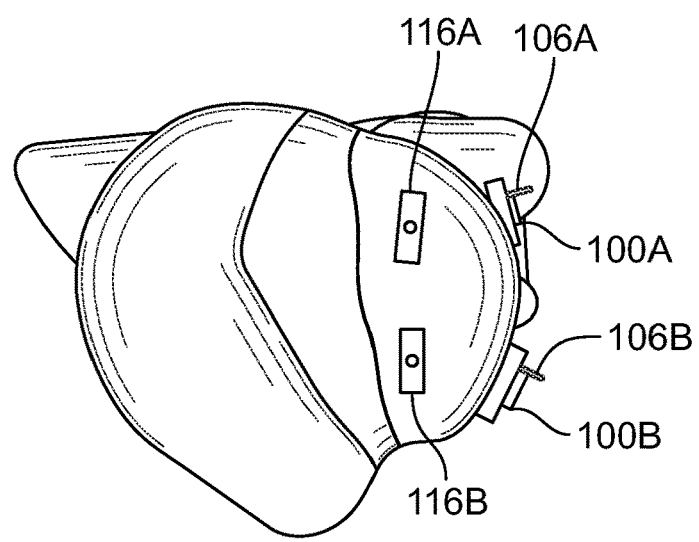
FIG. 55 illustrates a top view of the embodiment of FIG. 54.

In a further embodiment, one or more fixation device 100 may be used to repair an avulsion fracture of tissue 200, for example a greater tuberosity of the humerus. (FIGS. 54-57). Fastener 116 may include a soft, flexible, deformable fastener (FIG. 54), solid button (FIG. 55), or a combination thereof. Tissue 202 may include any hard or soft tissue, for example a rotator cuff. Fastener 116 may be connected to elongate member 106 and/or positionable on tissue 202 (i.e. an upper area of the rotator cuff) and/or tissue 206 (i.e. a greater tuberosity fragment). (FIG. 54). Elongate member 106 may be positioned through tissue 202, tissue 204, and/or tissue 206, for example including a fracture and/or humeral head. Fixation device 100 may be connected to elongate member 106 and/or positionable on tissue 204, for example below the fracture on the lateral side of the humerus.

Figure 56:
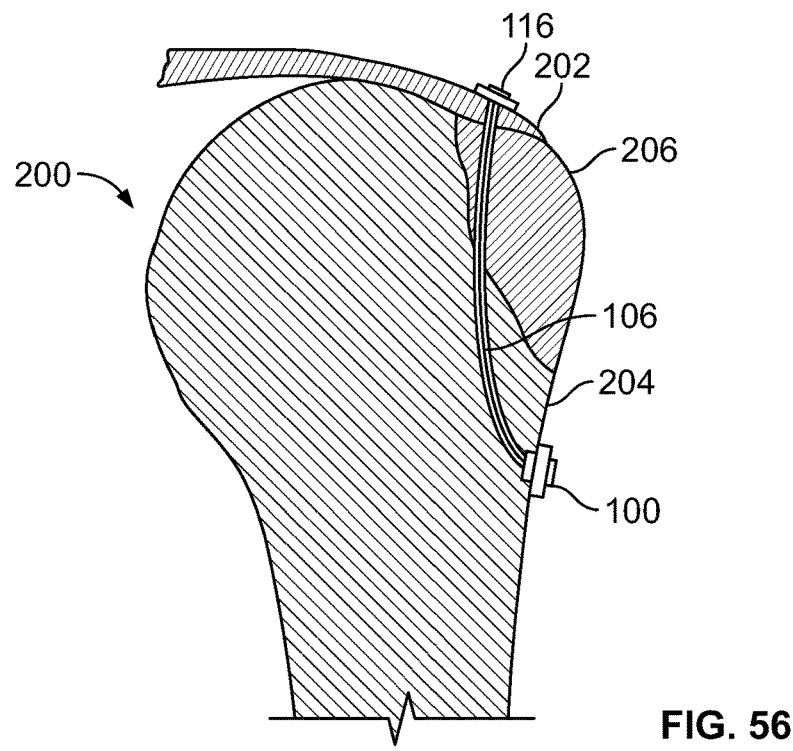
FIG. 56 illustrates a side section view of the embodiment of FIG. 54, for example, including soft and/or hard tissue fixation.
Figure 57:
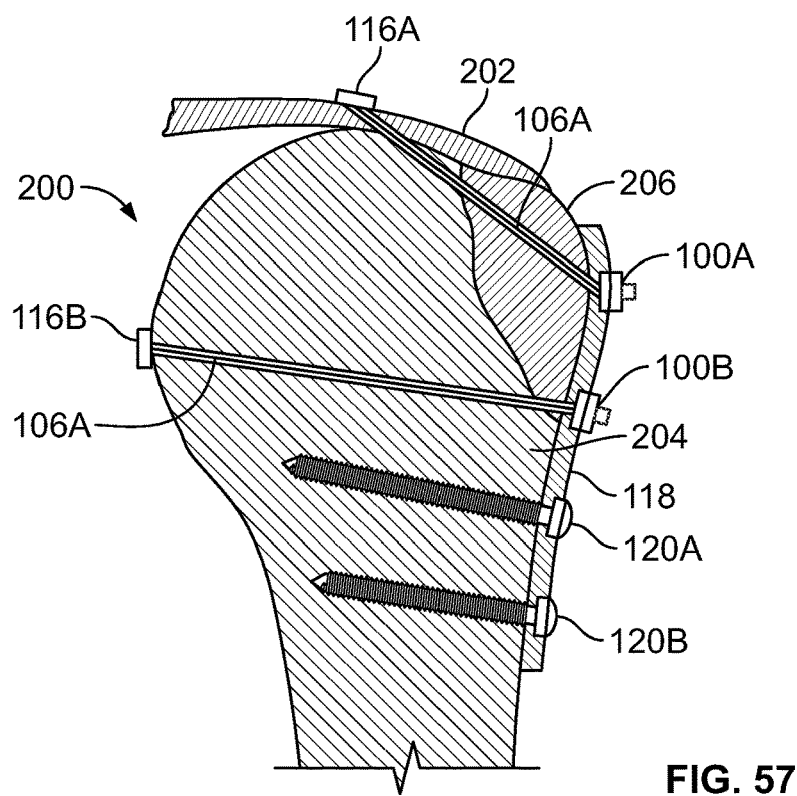
FIG. 57 illustrates an alternative embodiment of FIG. 54, for example, including a plate and screws.

Elongate member 106 may be positioned through a straight or curved passage. Elongate member 106 may be positioned through tissue 202, 204, and/or 206, for example, through the humerus and/or greater tuberosity fracture. (FIG. 56). A curved or bendable awl or drill may be used to create the passage. Fasteners 116, elongate members 106, and/or fixation devices 100 may be integrated into and/or used with plate 118 and screws 120. (FIG. 57). Screws 120A and 120B may secure plate 118 to tissue 204, for example the humerus. Distal anchors 116A and 116B, elongate members 106A and 106B, and fixation devices 116A and 116B may be positionable through tissue 202 (i.e. rotator cuff), tissue 206 (i.e. a greater tuberosity fragment), and/or tissue 204 (i.e. a humeral head), for example, to secure the fragment and avulsed rotator cuff.

Figure 58:
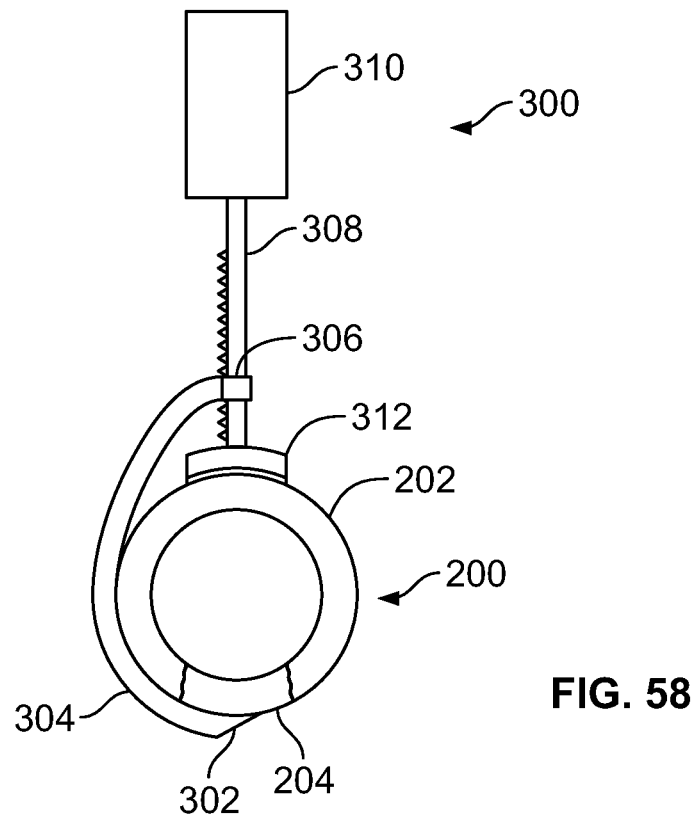
FIG. 58 illustrates an embodiment of the present disclosure, for example, including clamp configured to reduce and/or cut a tissue fracture.
Figure 59:
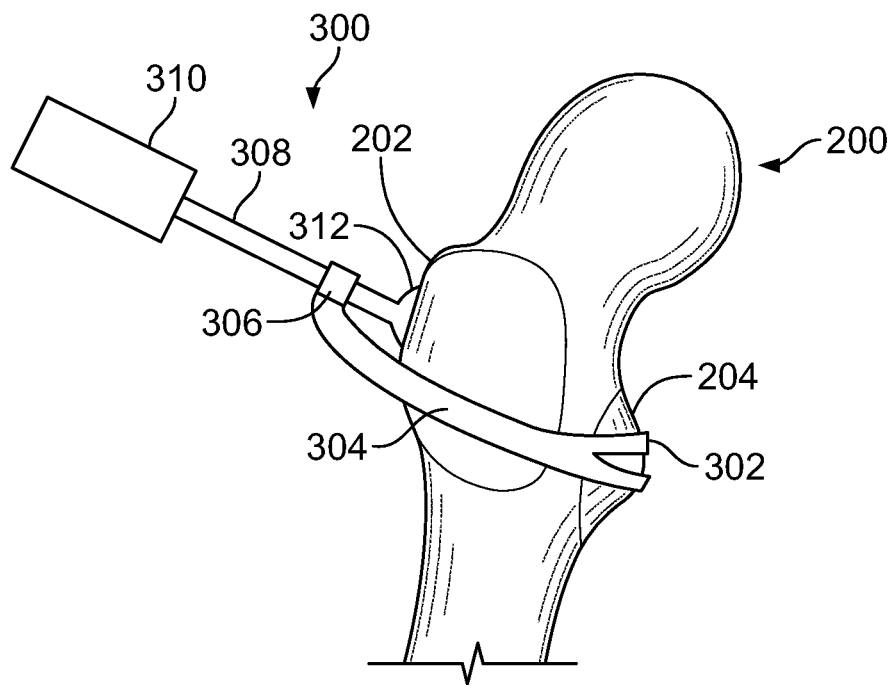
FIG. 59 illustrates an isometric view of an embodiment of FIG. 58, for example, positioned to secure and/or repair a lesser trochanter of a femur.

In another embodiment, clamp 300 may be configured to align and reduce the fracture of tissue 200 to drill through the tissue 202 and 204, for example bone fragments. (FIGS. 58-59). Clamp 300 may include leading portion 302, hook portion 304, connection 306, elongate portion 308, handle 310, and/or seat 312. Leading portion 302 may be configured to pierce and/or form a passage through tissue 200 and/or include surfaces configured to grasp and/or position tissue 204, fastener 116, and/or elongate member 106. Hook portion 304 may be configured to curve around tissue 200 for positioning of clamp 300 from a proximal area of tissue 202 to a distal area of tissue 204. Connector 306 and elongate portion 308 may include any connection suitable for controlled movement, for example a ratchet, worm gear, cable, or pneumatic connection. Connector 306 may advance along elongate portion 308 to urge tissue 202 and 204 together. Seat 312 may be configured to grasp and/or position tissue 202. Clamp 300 may be configured to receive and guide a drill to create the passage through tissue 200. Clamp 300 may be configured to secure any fractures of the body, for example the lesser trochanter for repair. (FIG. 59). Leading portion 302 may include a forked end, for example, to allow the drill device to pass through tissue 200 and between the forks of the clamp 300.

Figure 60:
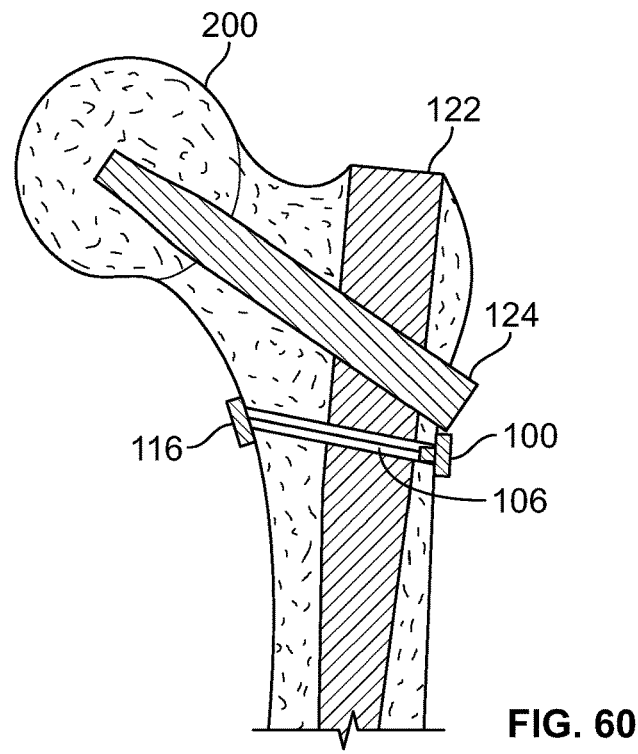
FIG. 60 illustrates a section view of an embodiment, for example, including repair of a tissue fracture of a proximal femur.
Figure 61:
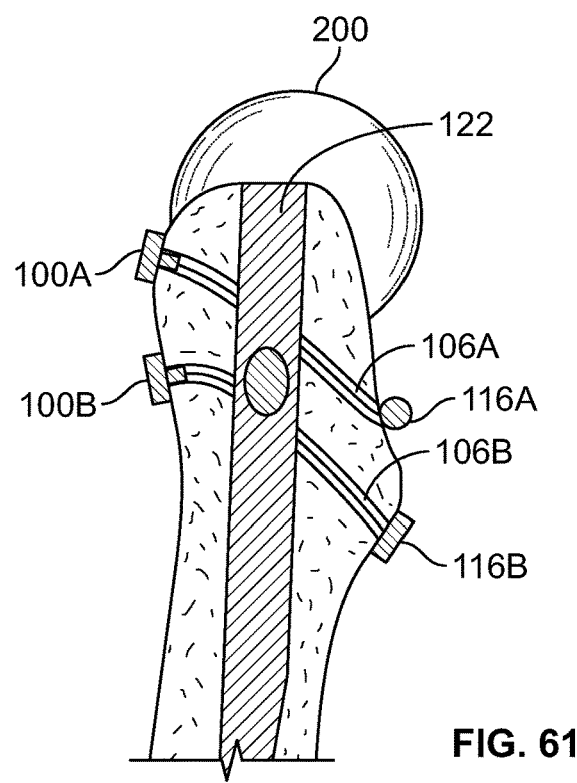
FIG. 61 illustrates an alternative section view of an embodiment of FIG. 60.
Figure 62:
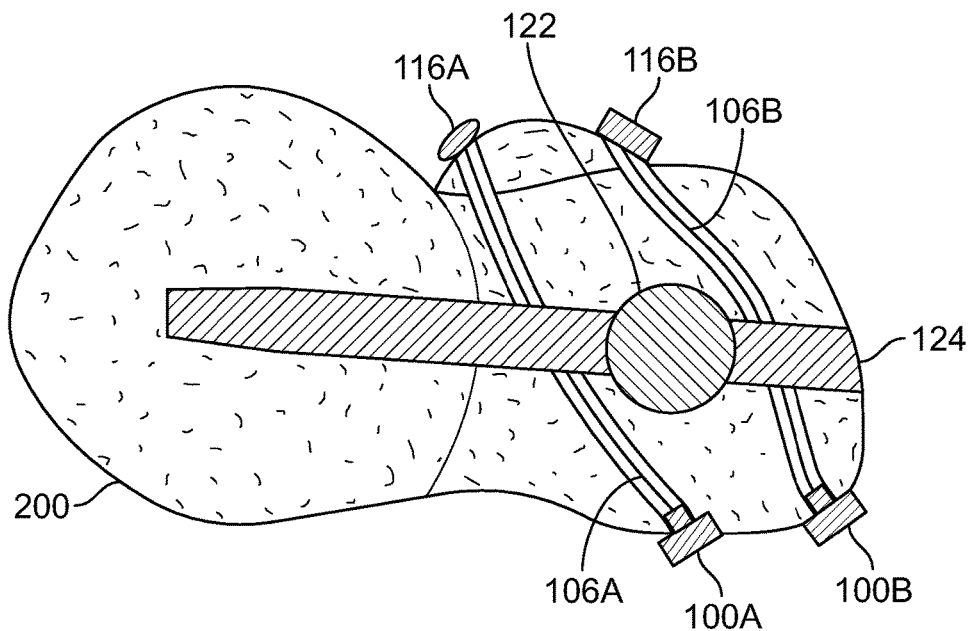
FIG. 62 illustrates an alternative section view of an embodiment of FIG. 60.

Fixation device 100, elongate member 106, and/or fastener 116 may be used in conjunction with other implants, for example implant 122 and/or screw 124. Implant 122 may include an intramedullary rod or nail. Implant 122 may be positioned at any location in the body, for example, to repair a fracture of the proximal femur. (FIGS. 60-62). Implant 122 may be secured with screw 124, for example a lag screw. (FIG. 60). Fastener 166 connected to elongate member 106 may be passed through an attachment feature (i.e. hole) in rod 122 and/or secured with fixation device 100 on the surface of tissue 200. (FIGS. 60-61). Implant 122 may also be secured with fixation device 100 connected to elongate member 106 secured to implant 122 and/or with screw 124 or a nail in the hole through which elongate member 106 is passed.

Embodiments may include two or more sets of fasteners 116, elongate members 106, and/or fixation devices 100 in conjunction with implant 122. (FIG. 61). Fasteners 116 and elongate members 106 may be passed through or around implant 122 (FIG. 62). The passages may be straight or curved, for example using a curved or bendable introducer or drill. (FIG. 61).

Figure 63:
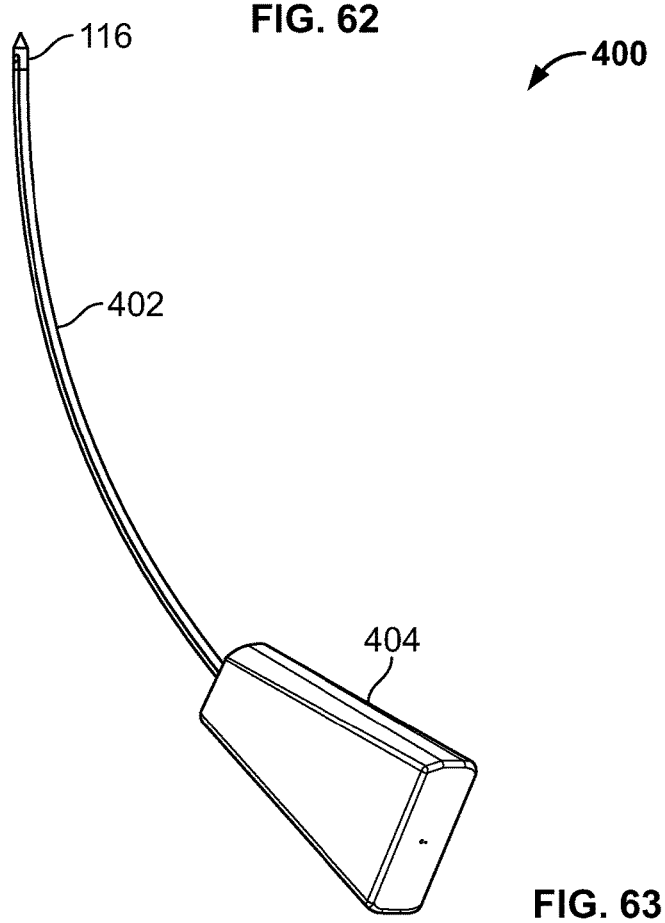
FIG. 63 illustrates an isometric view of an embodiment, for example, including a fastener attached to an introducer such as an awl.
Figure 64:
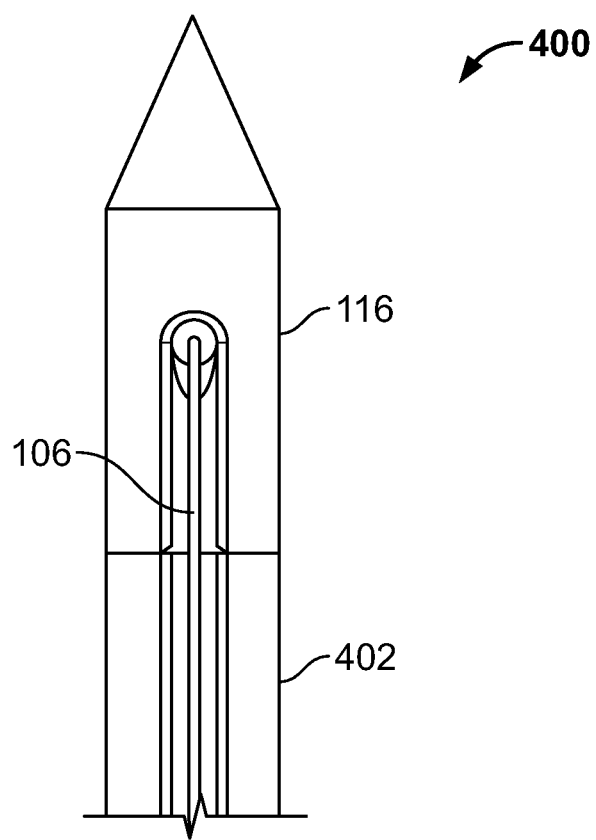
FIG. 64 illustrates a closer view of an embodiment of FIG. 63.
Figure 65:
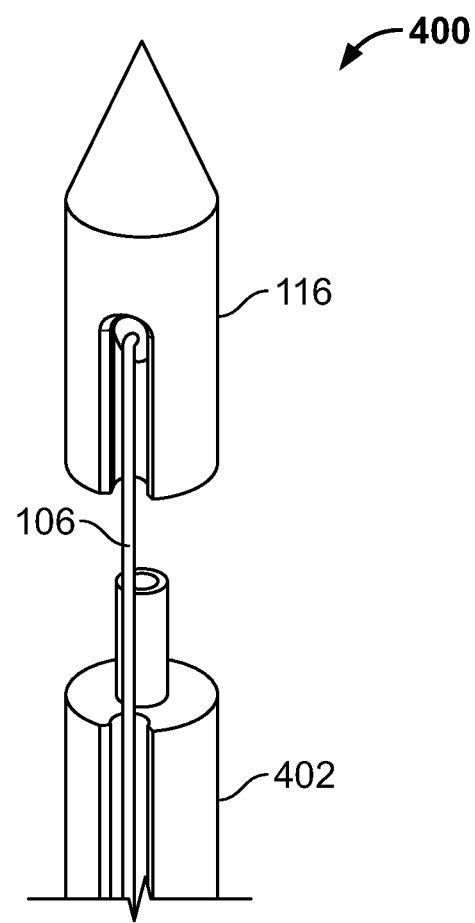
FIG. 65 illustrates an alternative view of an embodiment of FIG. 64, for example a deployed configuration.

Embodiments may include introducer 400, for example an awl. (FIGS. 63-65). Introducer 400 may include fastener 116, elongate portion 402, and/or handle 404. Fastener 116 may be releasably attached to and/or positionable with introducer 400. Introducer 400 may include a sharp or pointed leading end and/or be configured to create a passage in tissue 200. Fastener 116 may provide the sharp or pointed leading end for penetrating tissue, be releasably attached at a distal portion of introducer 400, and/or may be removed after passage is created. (FIG. 63). All or any portion of elongate portion 402 and/or handle 404 may include a passage for elongate member 106 and/or fastener 116. Handle 404 may be used to hold introducer 400 while applying pressure toward tissue 200 and/or urging introducer 400 from side to side to advance the leading end of introducer 400 through tissue. Elongate portion 402 may be curved (shown), bendable, flexible, rigid, straight, and/or have one or more curvatures in one or more planes to approximate a tissue passage or access path. Elongate portion 402 and/or handle 404 may be configured to receive or to be used with an introducer or cutting instrument, for example a drill bit, punch, or reamer. All or any portion of elongate portion 402 and/or fastener 116 may include a channel configured to receive elongate member 106 and/or protect elongate member 106 as introducer 400 is advanced into tissue. (FIG. 64).

Fastener 116 may be releasably attached to introducer 400. (FIG. 65) Introducer 400 may include a shaft with a distal portion including a hollow cylindrical shaped attachment feature. Introducer 400 may be configured to mate with a similar shaped cavity in the proximal end of fastener 116. Attachment feature may include a press-fit or threads. Elongate portion 402 and fastener 116 may include attachment features to maintain engagement during positioning. The attachment feature may include a cross-sectional shape that is circular (shown), triangular, square, rectangular, pentagonal, hexagonal, keyed, or any other shape configured to align and secure elongate portion 402 and fastener 116.

Figure 66:
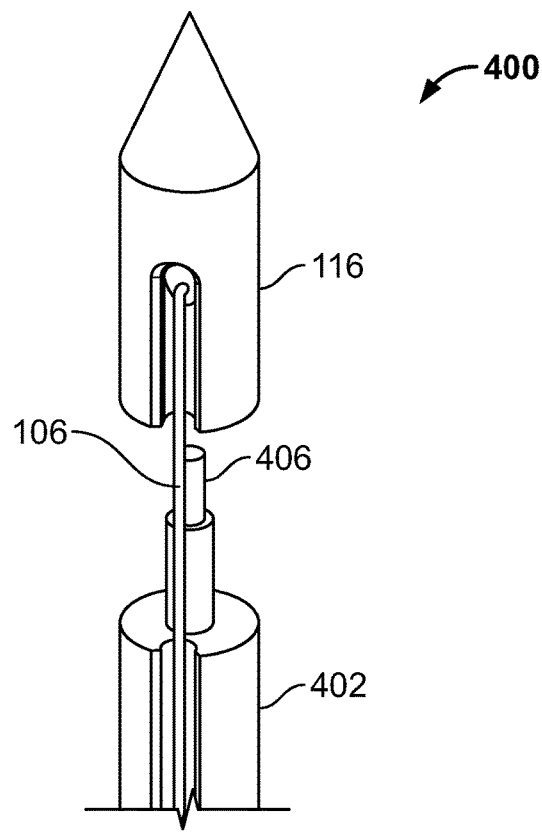
FIG. 66 illustrates an alternative view of an embodiment of FIG. 63, for example, including an attachment feature.
Figure 67:
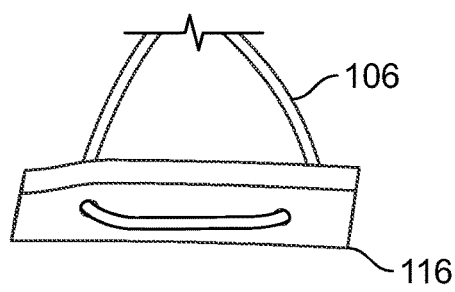
FIG. 67 illustrates an isometric view of an alternative embodiment, for example, including an alternative fastener configured to receive an elongate member in at least two locations.
Figure 68:
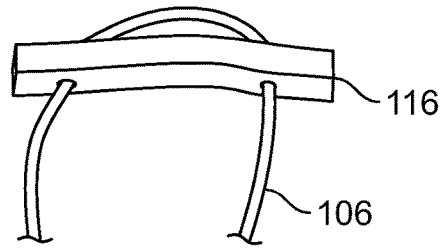
FIG. 68 illustrates an alternative view of an embodiment of FIG. 67.

Introducer 400 may include pushrod 406. (FIG. 66). Pushrod 406 may be configured to disconnect fastener 116 from elongate portion 402. Pushrod 406 may be urged through the passage in introducer 400. After pushrod 406 is positioned through the passage of introducer 400, a leading end of pushrod 406 may urge fastener 116 away from elongate portion 402. Pushrod 406 may also attach to fastener 116 with an attachment feature, for example a press-fit, threads, or another feature disclosed herein to retain fastener 116. The attachment feature of pushrod 406 may be used in conjunction with or in place the attachment feature of elongate portion 402. Pushrod 406 may be curved, bendable, rigid, straight, and/or have one or more curvatures in one or more planes to accommodate a tissue passage or desired access path.

Fastener 116 may include flexible, bendable, and/or deformable configurations for securing elongate member 106. (FIGS. 67-80). Fastener 116 may be substantially flat and/or woven. Elongate member 106 may pass, slide, and/or be tensioned through all or one or more portions of fastener 116. Embodiments may include any combination of nonwoven, polymer, fabric, sheet, composite, flexible, deformable, hydrophilic, and/or expandable materials. Elongate member 106 may be passed through, along, and/or around fastener 116. In use, as tension is applied to elongate member 106, fastener 116 may contract, deform, bunch, and tighten, for example, to resist being pulled through a body tissue or a hole through which fastener 116 was passed. Fastener 116 may include any cross-sectional shape disclosed herein or any other shapes configured to resist movement of elongate member 106 with respect to tissue.

Figure 69:
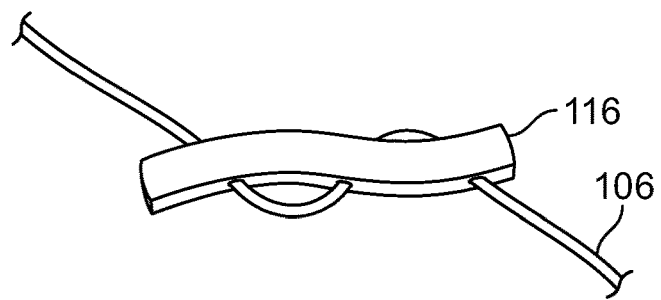
FIG. 69 illustrates an alternative embodiment of FIG. 67, for example, a fastener configured to receive an elongate member in at least three locations.
Figure 70:
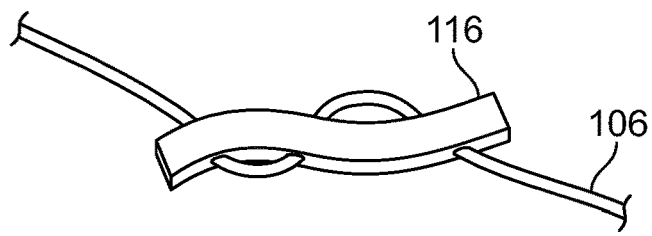
FIG. 70 illustrates an alternative view of an embodiment of FIG. 69.
Figure 71:
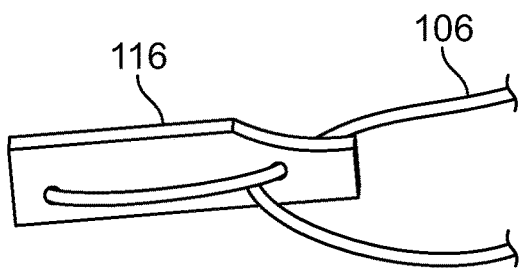
FIG. 71 illustrates an alternative view of an embodiment of FIG. 67.
Figure 72:
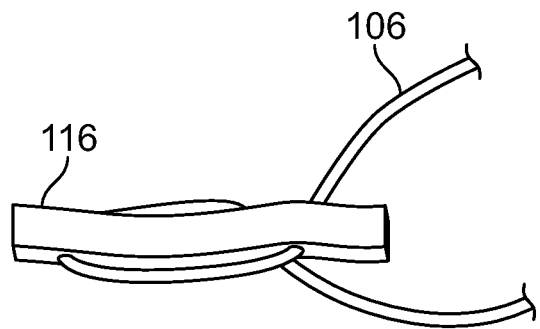
FIG. 72 illustrates an alternative view of the embodiment of FIG. 71.
Figure 73:
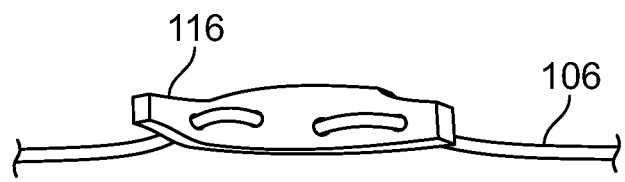
FIG. 73 illustrates an alternative embodiment of FIG. 67, for example, a fastener configured to receive an elongate member in at least four locations.
Figure 74:
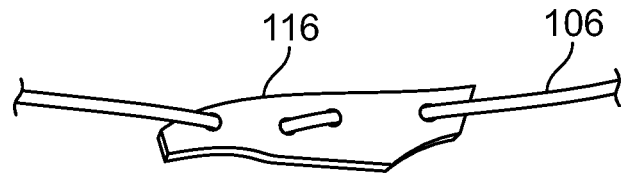
FIG. 74 illustrates an alternative view of an embodiment of FIG. 73.
Figure 75:
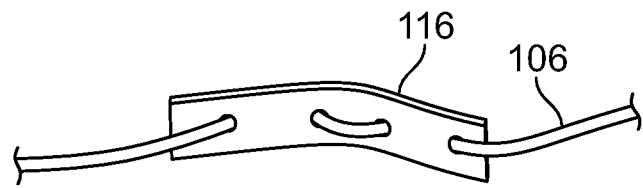
FIG. 75 illustrates an alternative embodiment of FIG. 67.
Figure 76:
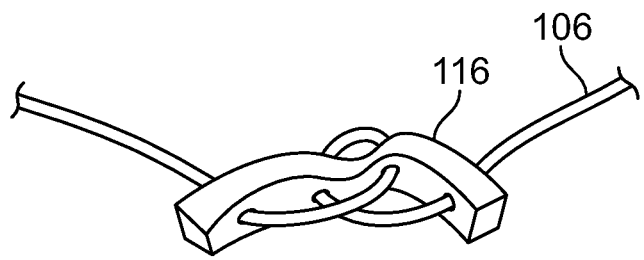
FIG. 76 illustrates an alternative view of an embodiment of FIG. 75.
Figure 77:
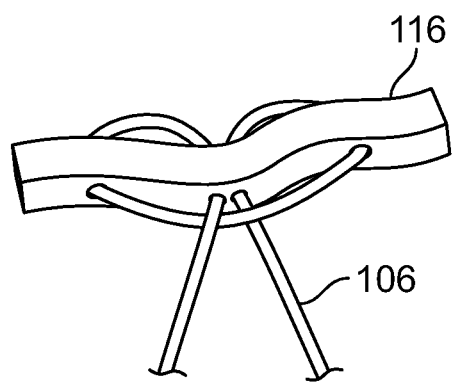
FIG. 77 illustrates an alternative embodiment of FIG. 67.
Figure 78:
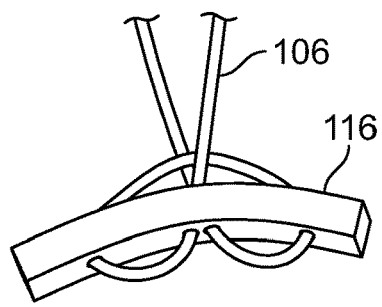
FIG. 78 illustrates an alternative view of an embodiment of FIG. 77.
Figure 79:
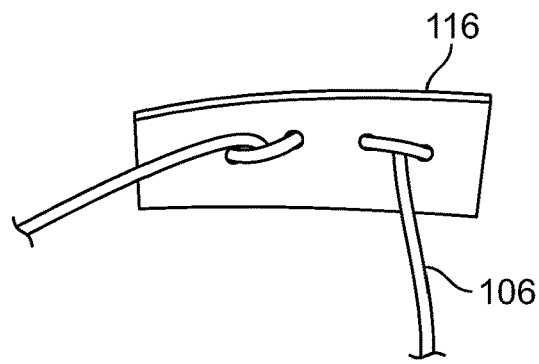
FIG. 79 illustrates an alternative embodiment of FIG. 67, for example, a fastener configured to receive an elongate member in at least six locations.
Figure 80:
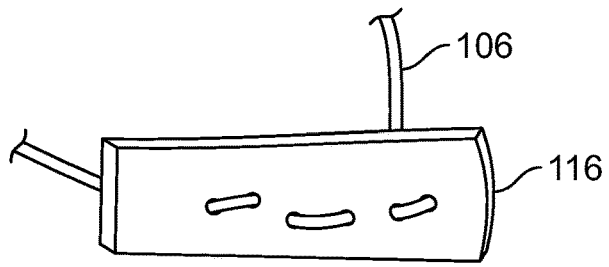
FIG. 80 illustrates an alternative view of an embodiment of FIG. 79.

Elongate member 106 may be positioned through fastener 116 in a limitless number of configurations. Elongate member 106 may pass through fastener 116 with any number of piercing locations, for example one (not shown), two (FIG. 67-68), three (FIGS. 69-72), four (FIGS. 73-78), five (not shown), six (FIGS. 79-80), or any other number of locations. Elongate member 106 may enter and exit from opposite ends and/or faces of fastener 116. (FIGS. 69-70). Elongate member 106 may form a loop through fastener 116 while entering and exiting from the same end and/or opposing faces of fastener 116. (FIGS. 71-72). Elongate member 106 may pass through fastener 116 with four distinct piercing locations and elongate member 106 enters and exits from opposing ends and/or the same face of fastener 116. (FIGS. 73-74). Elongate member 106 may form a loop through fastener 116 while entering and exiting from opposing ends and/or the same face of fastener 116. (FIGS. 75-76). Elongate member 106 may pass through a central portion of fastener 116, form a small loop by passing to one end of fastener 116, form a large loop when passing through the opposing end of fastener 116, form a second small loop, return through the central portion of fastener 116, and/or exit from the same face it entered. (FIGS. 77-78). Elongate member 106 may form five small loops with the two ends exiting on the same face in the central portion of fastener 116. (FIGS. 79-80).

Figure 81:
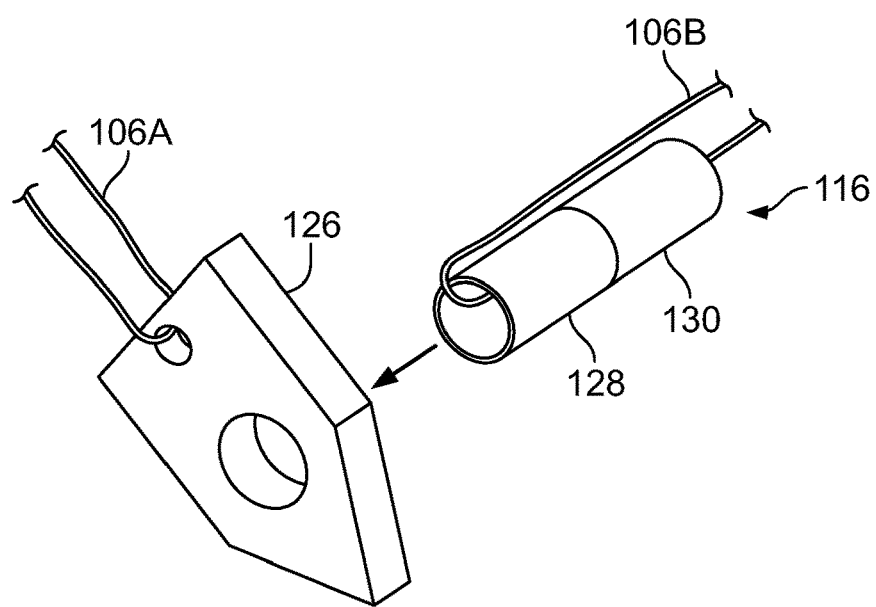
FIG. 81 illustrates an isometric view of an alternative embodiment, for example, including an alternative fastener having two or more components in an initial configuration.
Figure 82:
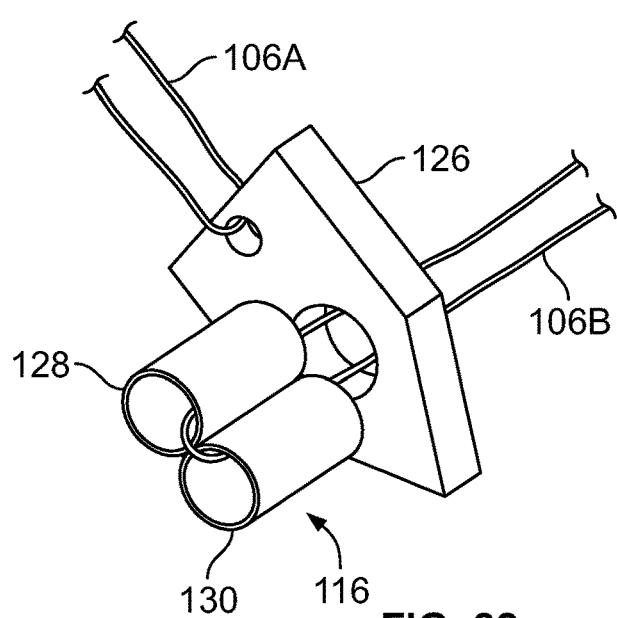
FIG. 82 illustrates an embodiment of FIG. 81, for example, in a second configuration.

Embodiments may include interlocking components 126, 128, and 130. (FIGS. 81-82). Component 126 may be connected to elongate member 106A. Fastener 116 may include components 128 and 130 and/or be connected to elongate member 106B. Components 128 and 130 may be bendably joint, for example with a hinge, or portions of one continuous component. Elongate members 106A and 106B may be distinct elements or portions of the same elongate member. Component 126 may include a first bore configured to receive elongate member 106A and/or a second bore configured to receive components 128 and/or 130 connected to elongate member 106B. Components 128 and 130 may each include a passage configured receive elongate member 106B. In use, components 128 and 130 connected to elongate member 106B are passed through the second bore while in a first configuration (FIG. 81), then elongate member 106B may be tensioned to reorient components 128 and 130 to a second configuration (FIG. 82). The second configuration of components 128 and 130 may obstruct movement of fastener 116 through the second hole thereby securing elongate member 106B relative to elongate member 106A.

Figure 83:
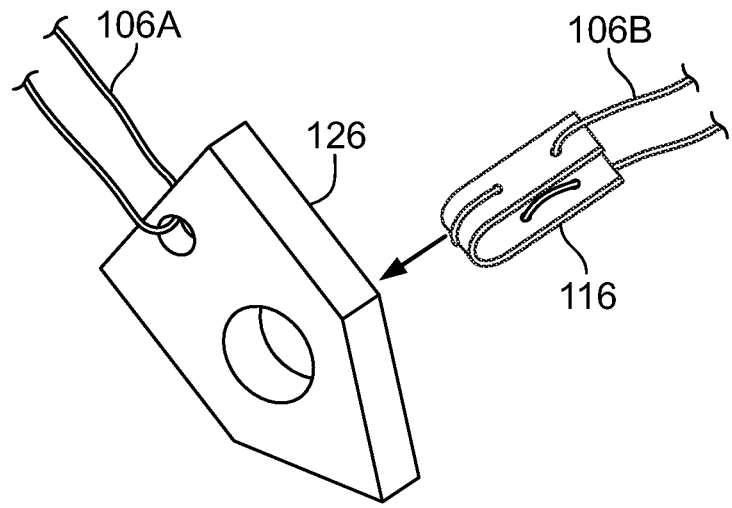
FIG. 83 illustrates an alternative embodiment of FIG. 81, for example, in an initial configuration.
Figure 84:
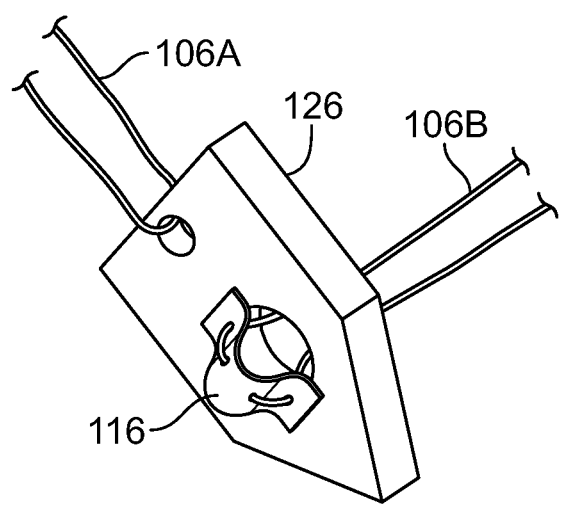
FIG. 84 illustrates an embodiment of FIG. 83, for example, in a second configuration.

Additional interlocking embodiments are contemplated herein. (FIGS. 83-84). Component 126 may be connected to elongate member 106A. Fastener 116 may be connected to elongate member 106B. Component 126 may include a first bore configured to receive elongate member 106A and/or a second bore configured to receive fastener 116 connected to elongate member 106B. Fastener 116 may include a passage configured receive elongate member 106B. Fastener 116 may include a flexible, bendable, deformable, and/or expandable material. In use, fastener 116 is configured to pass through the bore of component 126 while in a first configuration (FIG. 83), then elongate member 106B may be tensioned to deform fastener 116 to a second configuration (FIG. 84). The second configuration of fastener 116 may obstruct movement of fastener 116 through the second hold thereby securing elongate member 106B relative to elongate member 106A.

Figure 85:
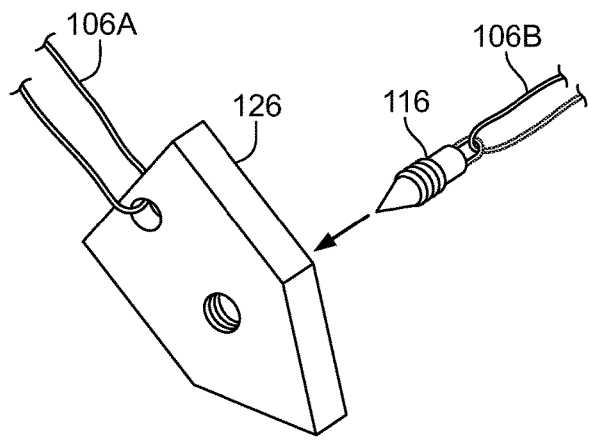
FIG. 85 illustrates an alternative embodiment of FIG. 81, for example, in an initial configuration.
Figure 86:
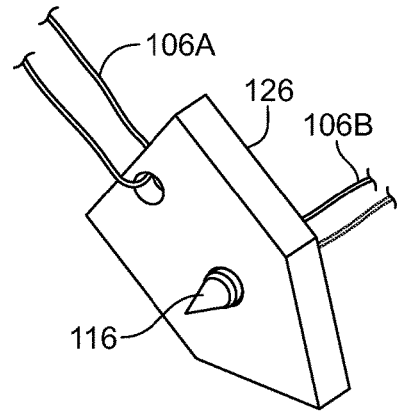
FIG. 86 illustrates an embodiment of FIG. 85, for example, in a second configuration.

Further interlocking embodiments may include smooth surfaces or attachment features to facilitate locking, for example threaded (shown), textured, roughed, and/or ribbed surfaces. (FIGS. 85-86). Fastener 116 may include a pointed leading end configured to penetrate tissue, a loop configured to connect with elongate member 106B, and/or an outer surface with attachment features configured to engage component 126. Component 126 may include a bore with attachment features configured to engage fastener 116. The attachment features of fastener 116 and/or component 126 may be configured to mate or interlock with each other. The outer surface of fastener 116 may create or tap threads into the bore of component 126 or vice versa. In use, fastener 116 may pass into and engage the bore of component 126 thereby locking fastener 116 and component 126 relative to each other.

Figure 87:
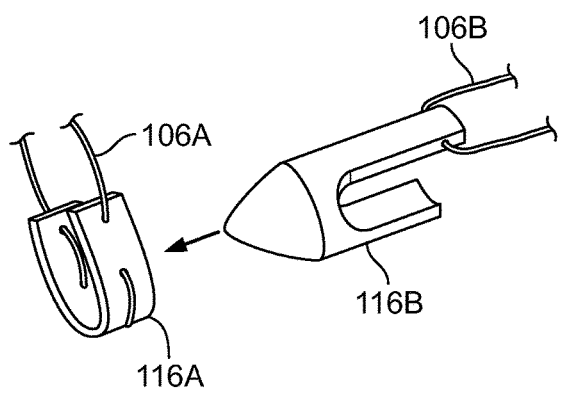
FIG. 87 illustrates an alternative embodiment of FIG. 81, for example, in an initial configuration.
Figure 88:
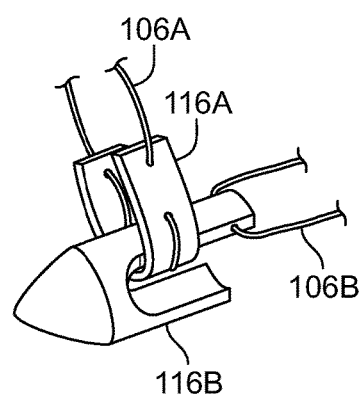
FIG. 88 illustrates an embodiment of FIG. 87, for example, in a second configuration.

Interlocking embodiments may also utilize various shapes or materials and/or combine one or more other embodiments disclosed herein. (FIGS. 87-88). Elongate member 106A may be connected to fastener 116A, for example a looped, deformable, woven, and/or substantially flat fastener 116. Alternatively, fastener 116A may be a rigid and/or solid loop and/or be integrated into elongate member 106A. Fastener 116B may include a hook. Fastener 116B may be configured to initially slide over fastener 116A then hook the loop of fastener 116A interlocks with fastener 116A when retracted or tensioned by elongate member 106B.

Figure 89:
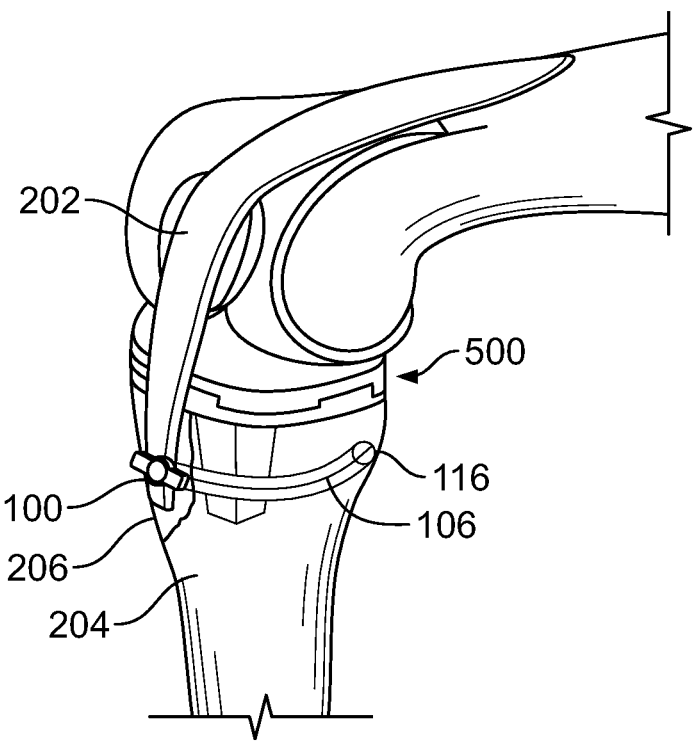
FIG. 89 illustrates an isometric view of an embodiment, for example, including repair of an avulsion fracture with a knee replacement.
Figure 90:
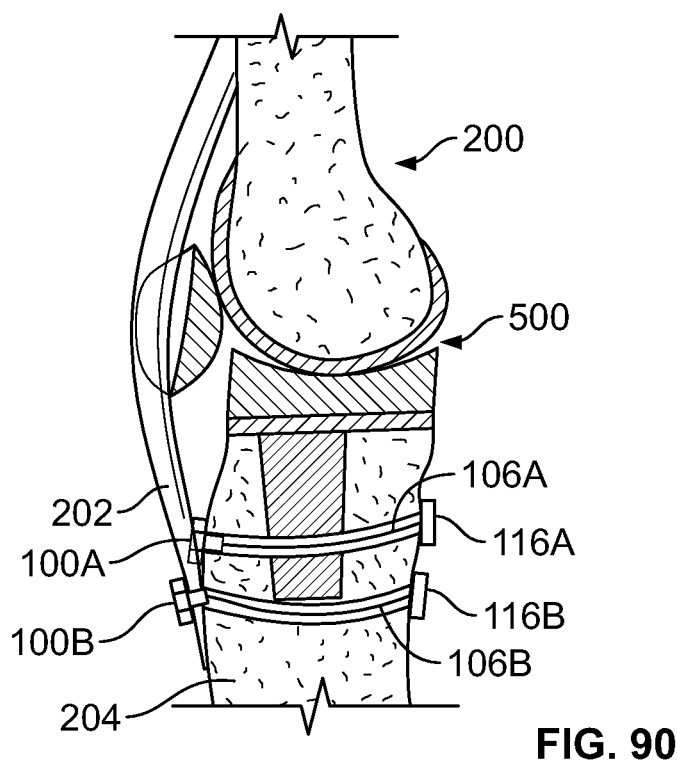
FIG. 90 illustrates a section view of an embodiment of FIG. 89.
Figure 91:
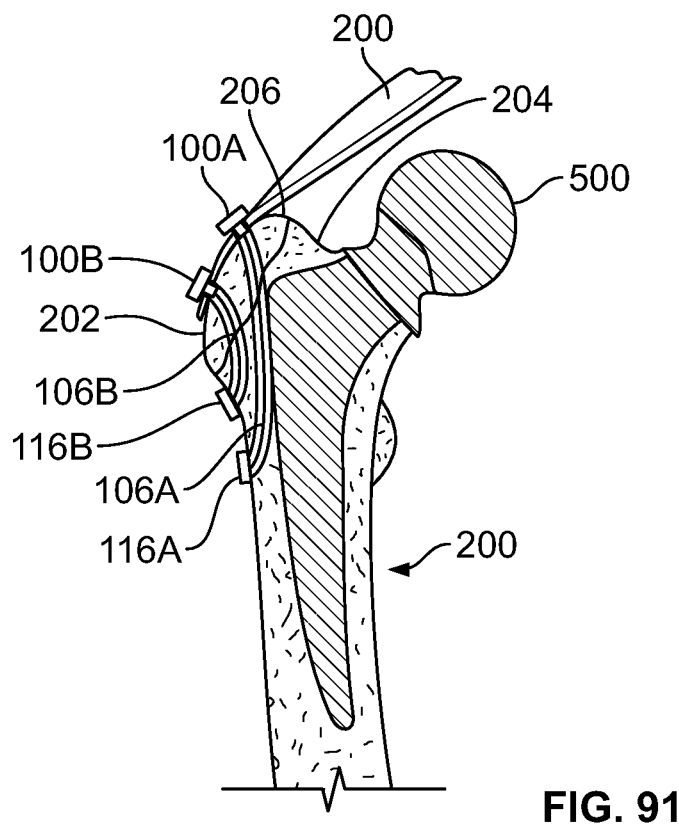
FIG. 91 illustrates section view of an embodiment, for example, including repair of an avulsion fracture with a hip replacement.

Embodiments may be used in conjunction with joint replacement 500. (FIGS. 89-91). Embodiments may be used with any joint in the body, for example a knee, hip, shoulder, ankle, toe, elbow, spine, wrist, hand, finger, and foot. Fastener 116 and elongate member 106 may be positioned around (FIG. 89) or through (FIG. 90) all or a portion of tissues 200 (i.e. knee joint) or joint replacement 500 (i.e. knee replacement). Tissue 202, 204, and/or 206 may be any combination of soft and/or hard tissues. Elongate member 106 may be connected to fixation device 100 to secure a fracture of tissues 200, for example an avulsion fracture of the tibial tubercle. Embodiments may include one or more fasteners 116, elongate members 106, and fixation devices 100. (FIG. 90). The passages through and/or around tissues 200 or joint replacement 500 may be curved or straight. Fixation devices 100 and fasteners 116 may also be secured exterior to the soft and/or hard tissues 200 of the joint. (FIG. 89) Fasteners 116 and fixation devices 100 may secure tissues from the outer surfaces covering soft and/or hard tissues. Fasteners 116 and fixation devices 100 may secure bone interosseously and be positioned internal to the joint tissues. (FIG. 90-91). Embodiments may be configured to repair any other joint of the body, for example a greater trochanter fracture near a hip replacement. (FIG. 91).

Figure 92:
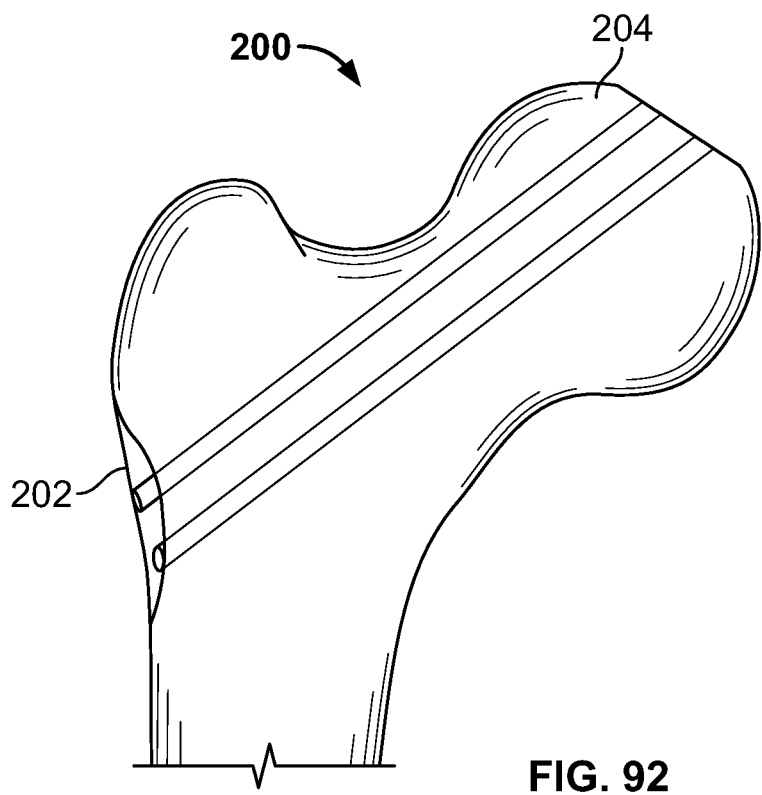
FIG. 92 illustrates an alternative embodiment, for example, an act for repairing an articular surface cartilage defect including creating one or more passages in the tissue.
Figure 93:
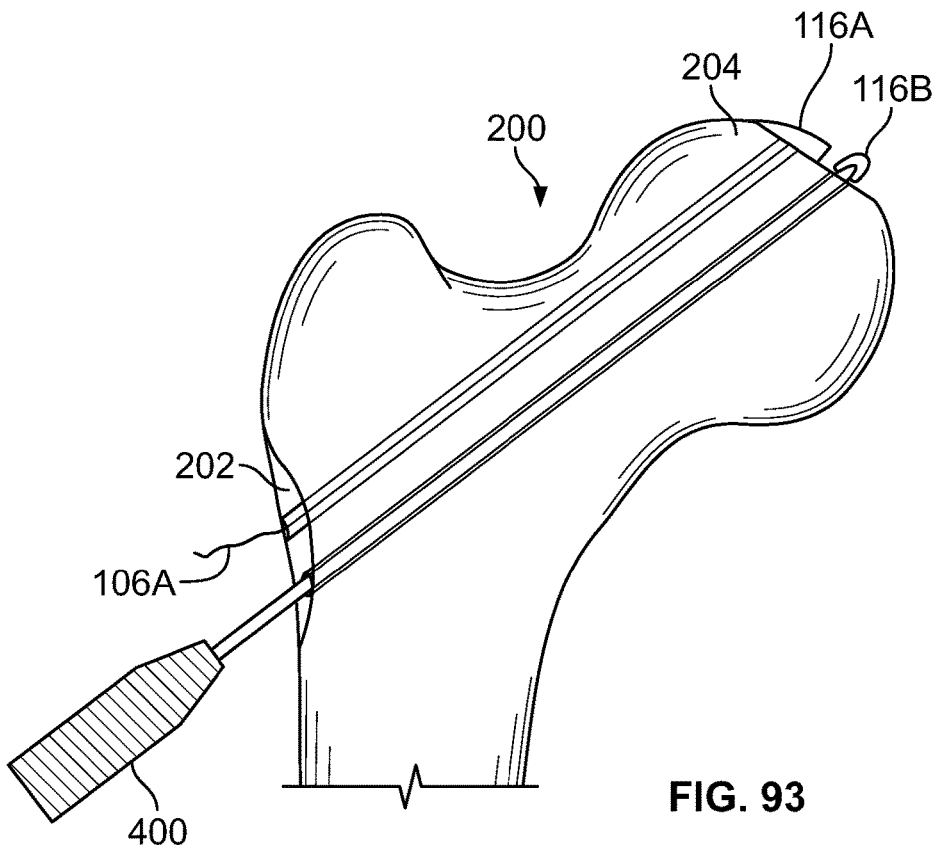
FIG. 93 illustrates an embodiment of FIG. 92, for example, including an act of inserting a fastener connected to an elongate member through the passage and positioning the fixation device at a distal area.
Figure 94:
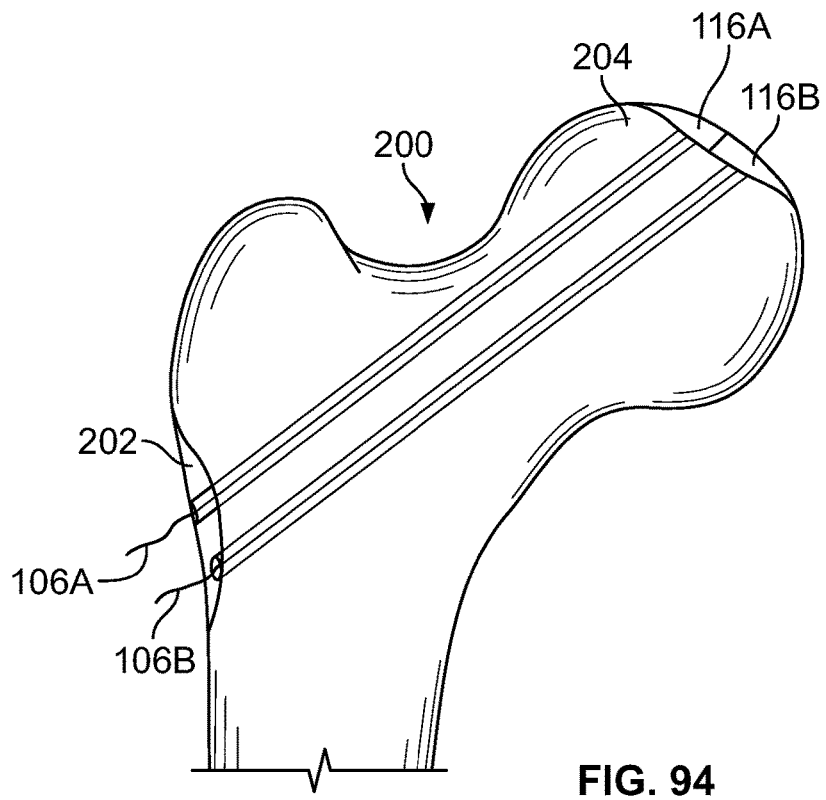
FIG. 94 illustrates an embodiment of FIG. 92, for example, including an act of deploying a fastener to approximate a natural curvature of an articular surface.
Figure 95:
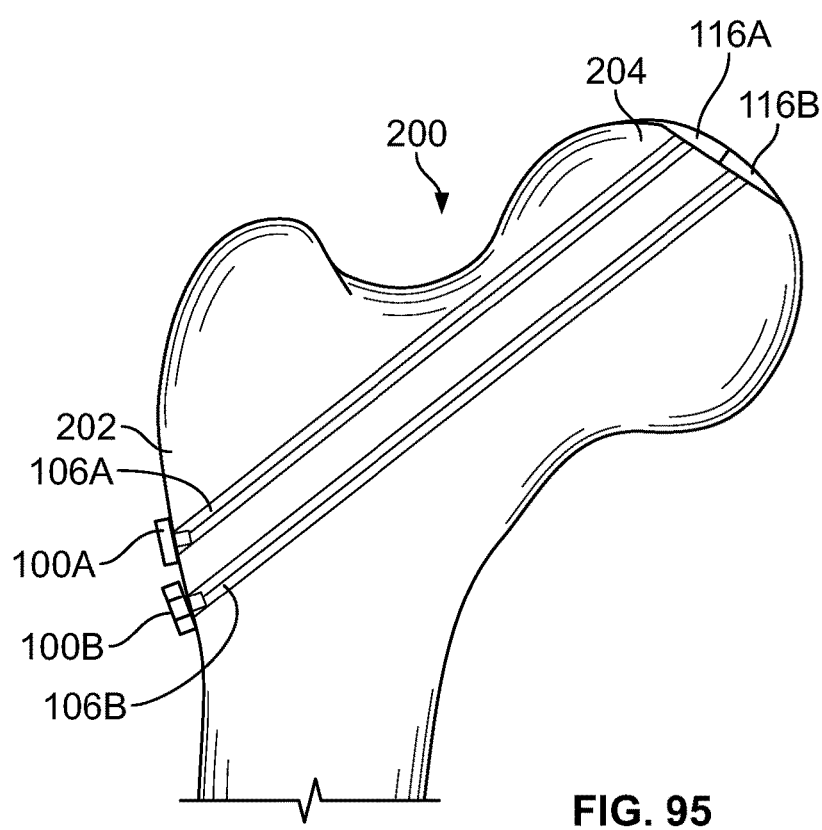
FIG. 95 illustrates an embodiment of FIG. 92, for example, including an act of securing a fastener with one or more fixation devices at a proximal area.

Further embodiments may be configured to repair tissue 200 of articular surfaces of the body, for example articular cartilage. (FIGS. 92-95). Passages may be created through tissue 200 (i.e. bone) to an articulating surface of a joint. (FIG. 92). Fasteners 116 connected to elongate members 106 may be positioned on the articular surface through the passages. (FIG. 93). Fasteners 116 may be deployed on the articular surface. (FIG. 94). Fasteners 116 may include a woven, mesh, scaffold, collagen, or any other synthetic or biologic material that encourages tissue growth to repair a tissue defect. Fastener 116 may be resorbable or permanent material. Fastener 116 may include any other material disclosed herein. Fasteners 116 may be secured to the articular cartilage surface by the attachment of an elongate member 106 and/or fixation device 100. (FIG. 95).

Figure 96:
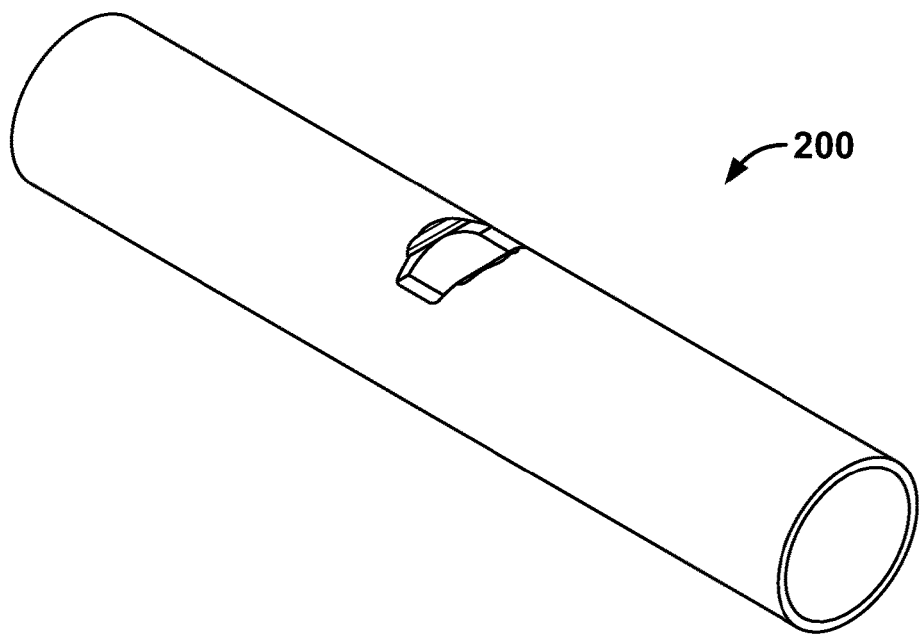
FIG. 96 illustrates an embodiment of the present disclosure, for example, including a passage with a defect.
Figure 97:
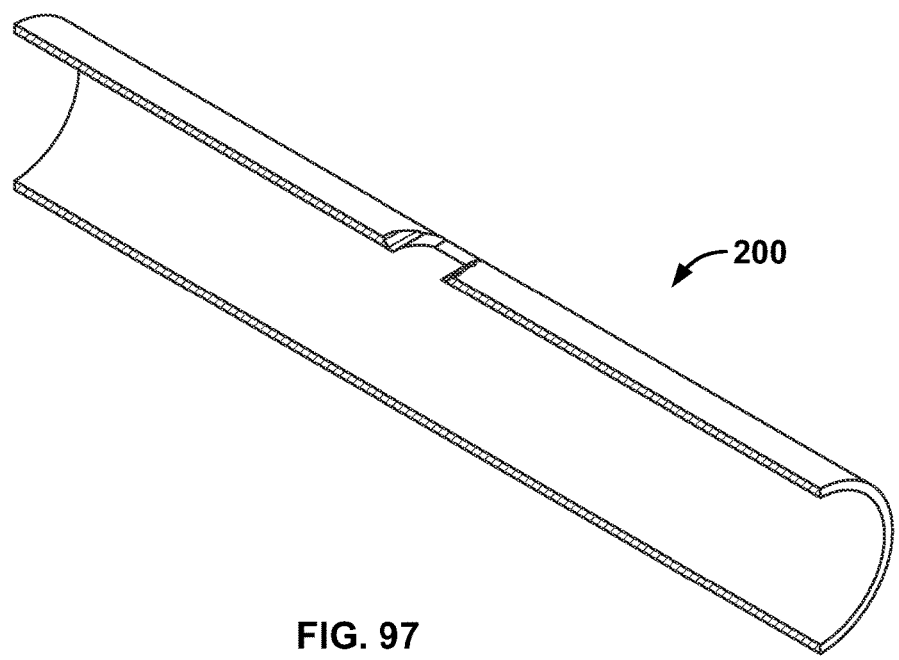
FIG. 97 illustrates a section view of an embodiment of FIG. 96.
Figure 98:
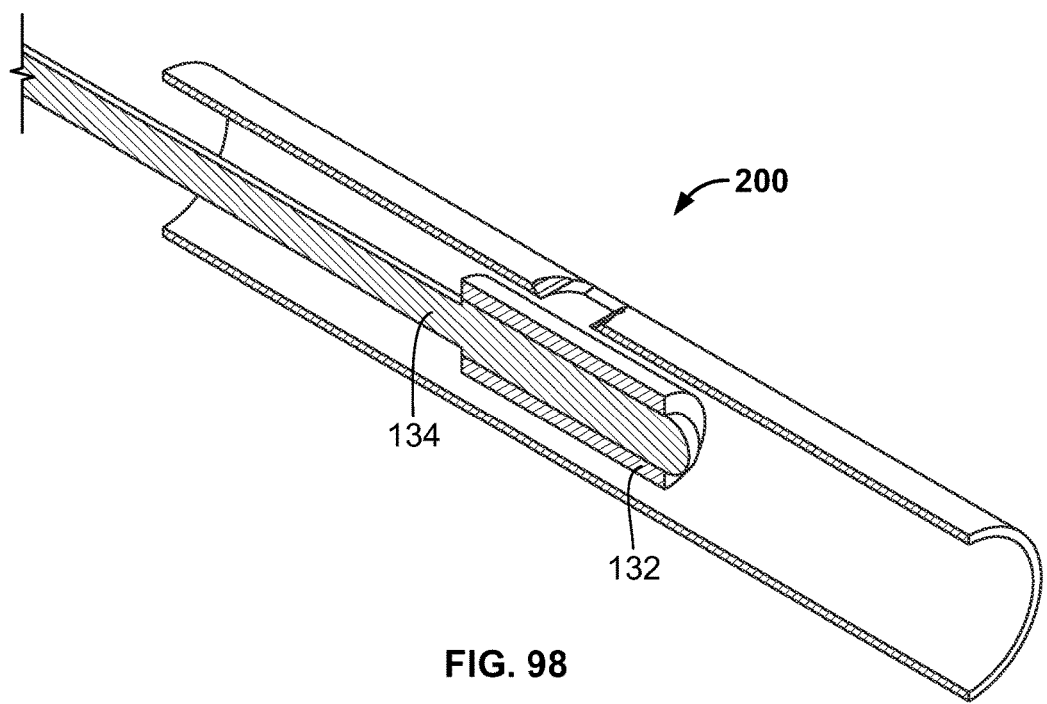
FIG. 98 illustrates an embodiment of FIG. 96, for example, including an alternative fixation device being positioned on an expandable device in the passage of FIG. 96.
Figure 99:
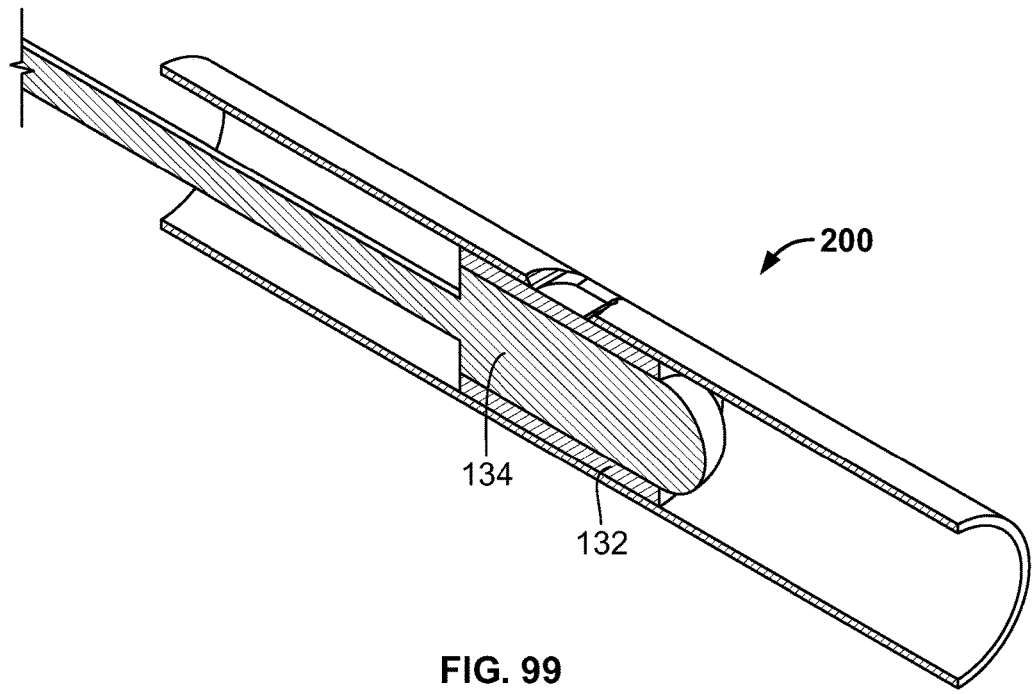
FIG. 99 illustrates an embodiment of FIG. 96, for example, including the expandable device urging radial expansion of a fixation device with an expanded configuration.
Figure 100:
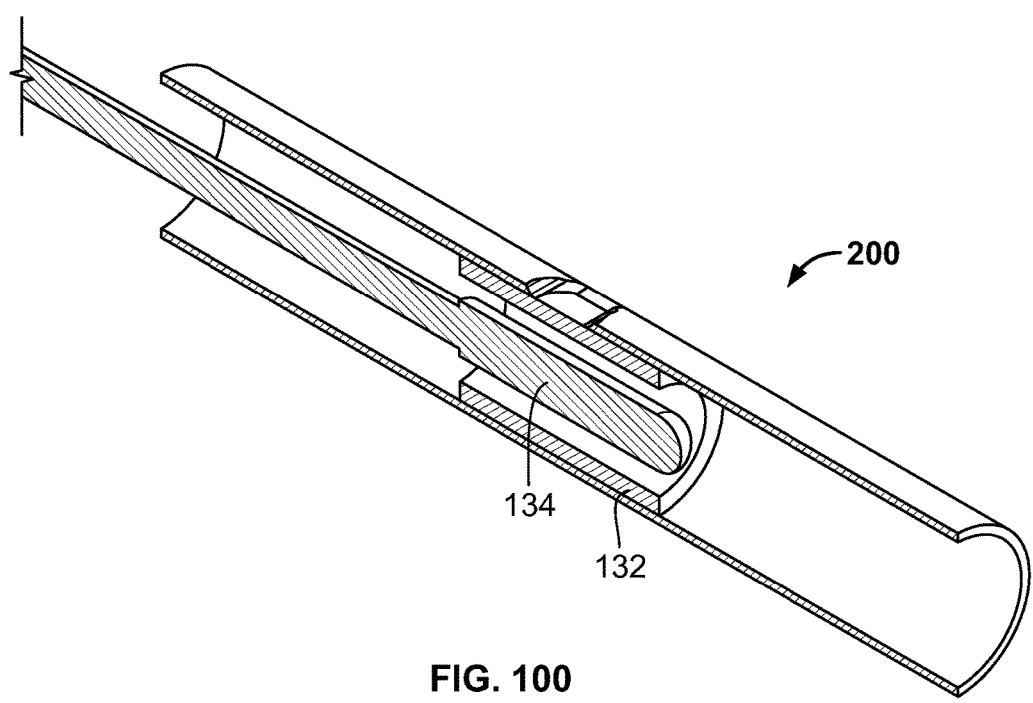
FIG. 100 illustrates an embodiment of FIG. 96, for example, deploying of the fixation device and retracting the expandable device in a contracted configuration.
Figure 101:
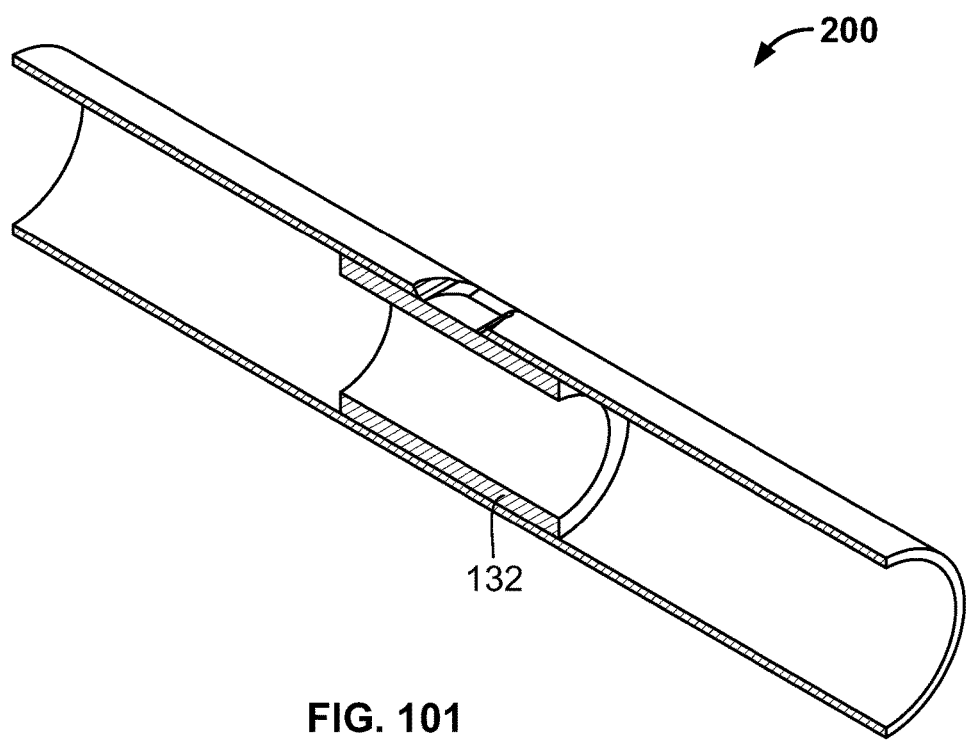
FIG. 101 illustrates an embodiment of FIG. 96, for example, the fixation device deployed and positioned against the passage.

Embodiments may be configured to repair a defect in a passage with implant 132. (FIGS. 96-101). The passage could be a natural or created passage through all or any portion of a bone, tendon, muscle, organ, blood vessel, and/or any other body tissue. (FIGS. 96-97). Implant 132 may include a mesh, scaffold, collagen, or other synthetic or biologic material that encourages tissue growth. Implant 132 may be positioned with introducer 134, which may be an expandable, inflatable, and/or balloon device. (FIG. 98). Introducer 134 may have a contracted configuration and an expanded configuration. Introducer 134 in the contracted configuration may axially position implant 132 along the passage to the location of the defect. At or near the location of the defect, introducer 134 may expand to the expanded configuration thereby radially expanding implant 132 against the defect. (FIG. 99) Introducer 134 may be radially contracted to the contracted configuration while the expanded implant 132 remains attached to the interior of the passage. (FIG. 100). The attachment may result from a mechanical attachment, mechanical and/or thermal expansion, adhesive, magnetic, ultrasonic activation, swelling, or any other method of adherence and/or expansion. Introducer 134 may be axially retracted from the passage while implant 132 substantially maintains an expanded position against the passage to repair the defect. (FIG. 101). Alternatively, implant 132 may include a biodegradable material configured to degrade and/or absorb after a period of time based on the material selected.

Figures 102, 103:
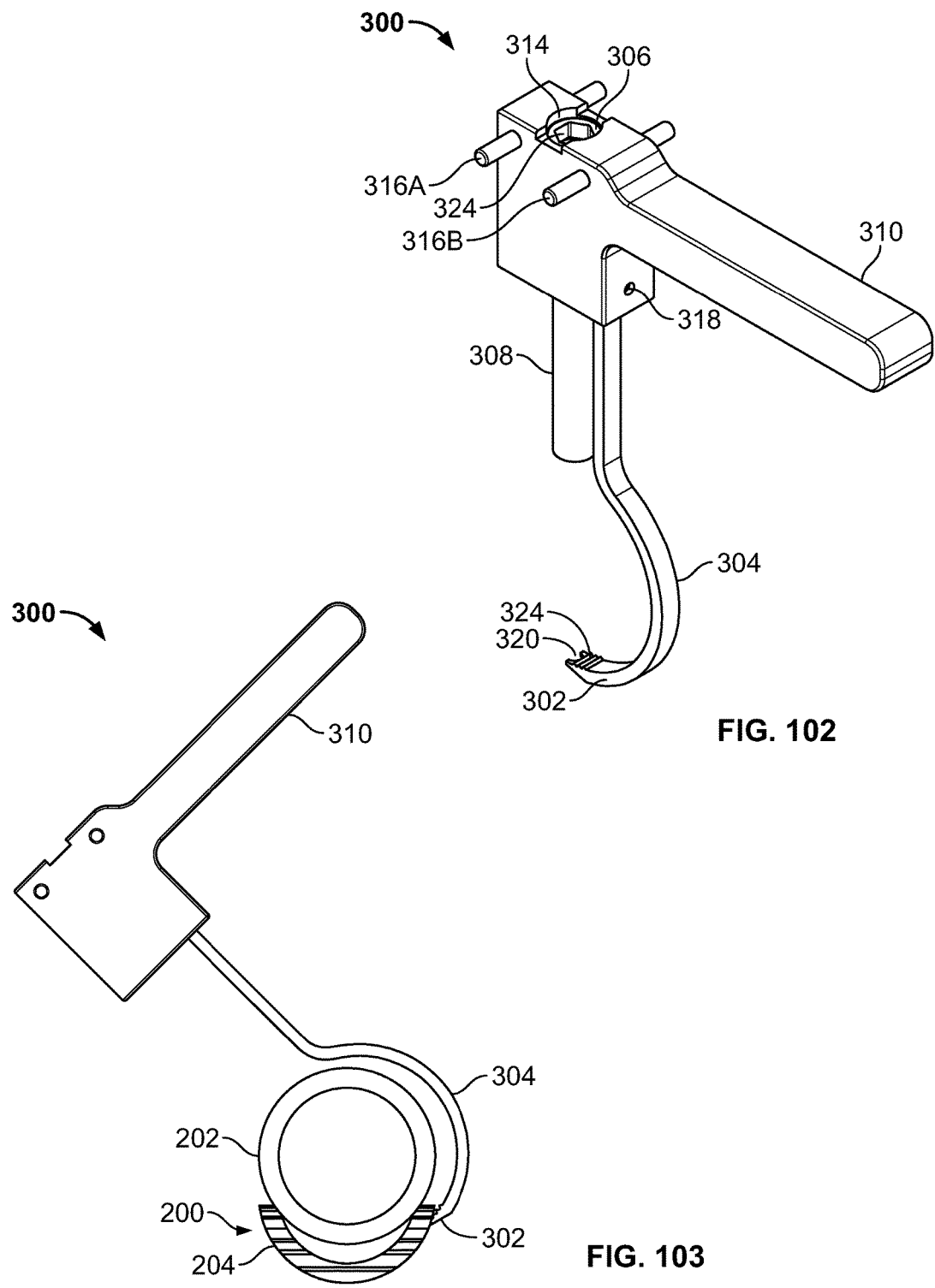
FIG. 102 illustrates an isometric view of an alternative embodiment of FIG. 58, for example, including a clamp configured to reduce a tissue fracture.
FIG. 103 illustrates a side view of the embodiment of FIG. 102, for example positioned to hook around a portion of at least two tissue fragments.

Additional embodiments may include clamp 300 and/or be configured for reduction of a fracture in conjunction with insertion of the fastener 116, elongate member 106, and fixation device 100. (FIGS. 102-109). Clamp 300 may be comprised of a leading portion 302, hook portion 304, connection 306, elongate portion 308, and/or handle 310. (FIG. 102) Hook 304 may be removable and/or replaceable with a hook 304 of a different configuration, for example straight or of a different curvature or radius. Handle 310 may include a locking mechanism 318 such as a set screw, clamp, or other feature configured to release the hook 304 for replacement hook 304 with a different configuration. A distal portion of leading portion 302 of hook 304 may include opening 320 configured to accept a drill and textured region 324 configured to grip bone fragments. Elongate portion 308 may be configured as a passageway for other instrumentation and/or a proximal clamp using connection 306 mating with bore 314 of handle 310. Connection 306 may include an attachment feature to mate with the bore 314 in handle 310, for the attachment feature may include threads, slots, clamps, or any other feature disclosed herein. Connection 306 may include a drive region 322 for an instrument (not shown) to screw the elongate portion 308 down to secure bone. (FIG. 102). Handle 310 may include posts 316 or other attachment features configured for attachment of other instruments or modular assemblies. Attachment features may include threads, clamps, internal bores and/or posts, or any other feature disclosed herein.

Figures 104, 105:
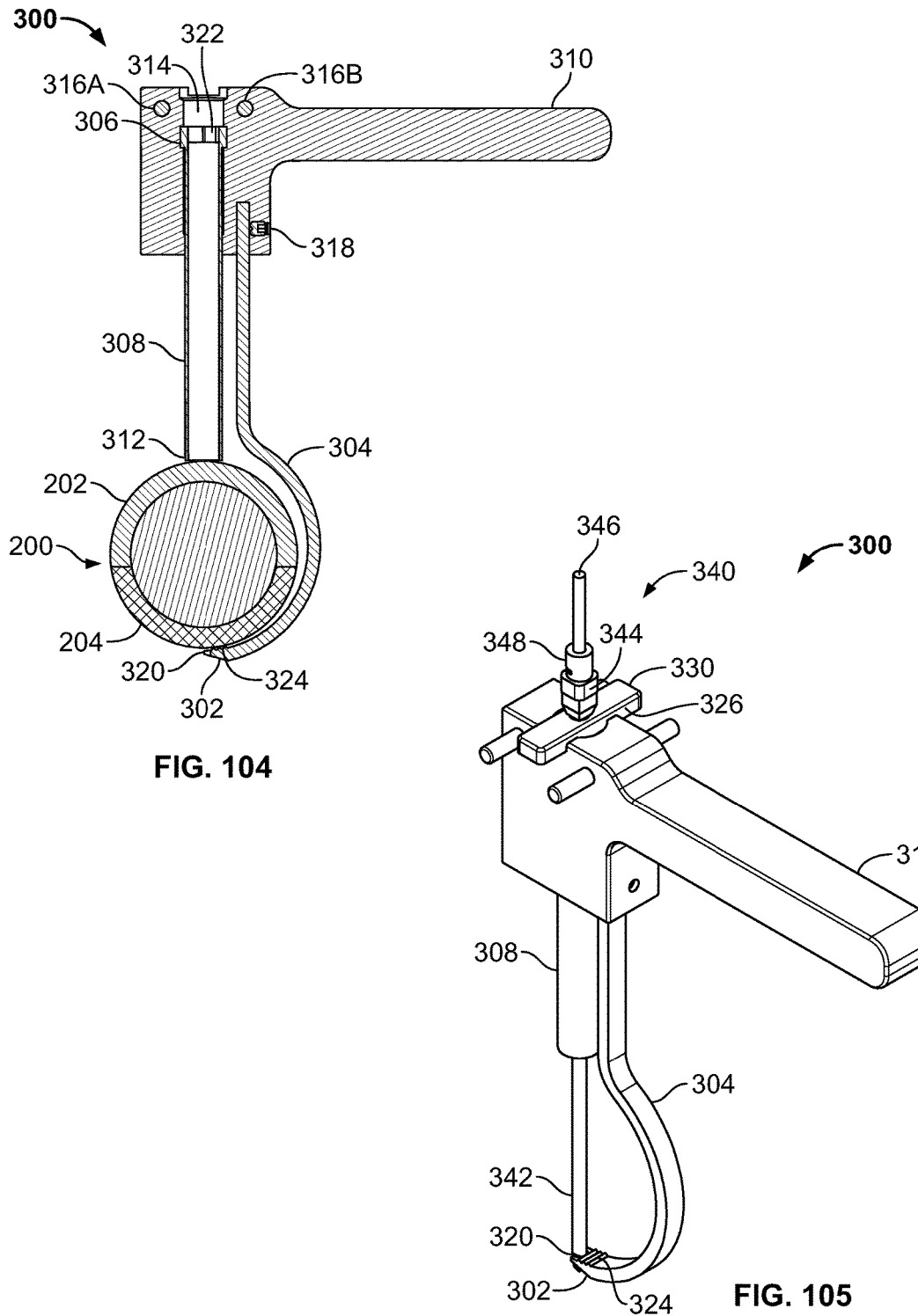
FIG. 104 illustrates a section view of the embodiment of FIG. 102, for example, urging together two tissue fragments.
FIG. 105 illustrates an isometric view of an alternative embodiment of FIG. 102, for example, including a cutting device.

Clamp 300 may be positionable around and configured to secure a fracture of tissue 200. (FIG. 103-104). Hook 304 may be configured to wrap around tissues 202 and 204. (FIG. 103-104). Leading portion 302 may be passed along and positioned around tissues 202 and 204, for example bone fragments. Leading portion 302 may be pulled back with or retracted into the handle 310 to reduce the fracture of tissue 200. Elongate portion 308 may be inserted into the threaded bore 314 in the handle and/or connection 306 may engage threads in bore 314. Elongate portion 308 may be driven by an instrument (not shown) until seat 312 contacts tissue 202, which may further reduce the fracture. After elongate portion 308 is positioned with respect to connection 306, the fracture of tissue 200 is reduced and/or secured between seat 312 and leading portion 302 of the hook 304.

Figure 106:
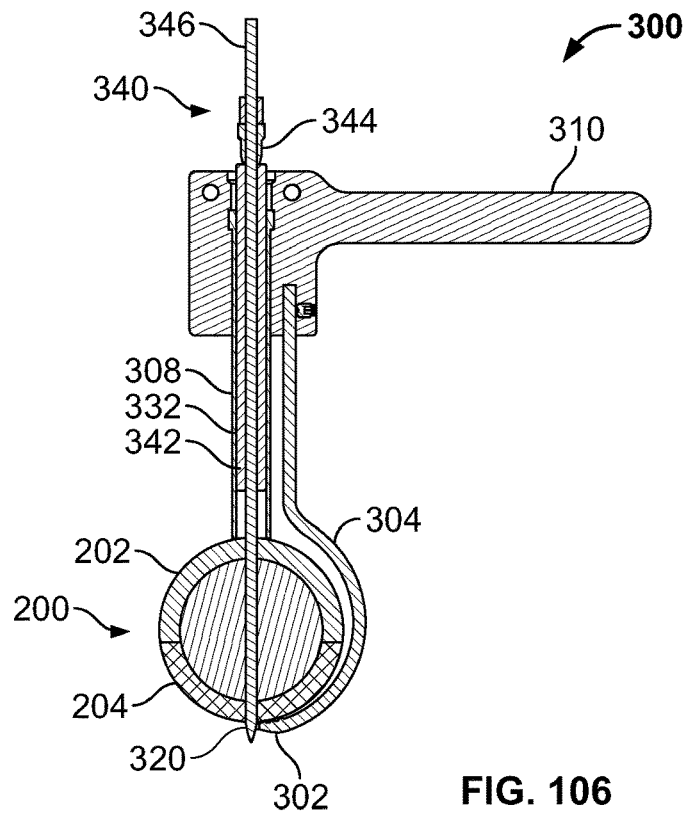
FIG. 106 illustrates a section view of an embodiment of FIG. 105, for example, including the cutting device configured to penetrate tissue of a fracture.

Clamp 300 may include drill guide 330 and/or drill assembly 340. (FIGS. 105-106). Drill guide 330 may include shaft 332. Shaft 332 may be configured to be passed into the passage of handle 310 and/or elongate portion 308, for example, until drill guide head 334 fits into slot 326 of handle 310. Drill assembly 340 may be attached to a powered drill (not shown) and/or advanced through handle 310, elongate portion 308, and/or drill guide 330. Drill assembly 340 may include two or more components, for example, including sleeve 342 and drill 346. Sleeve 342 and drill 346 may be secured together, for example, with attachment feature 344 on sleeve 342 and/or attachment feature 348 on drill 346. Attachment features 334 and/or 348 may include a keyed interlock or any other attachment feature disclosed herein. As drill assembly 340 is advanced through tissues 202 and 204, the distal portions of drill 346 and sleeve 342 may exit tissue 204 and/or pass through opening 320 of leading portion 302. After passing through the surface of tissue 304, drill assembly 340 may stop as attachment feature 344 contacts drill guide head 334. A powered drill (not shown) may then be detached from the drill assembly 340.

Figure 107:
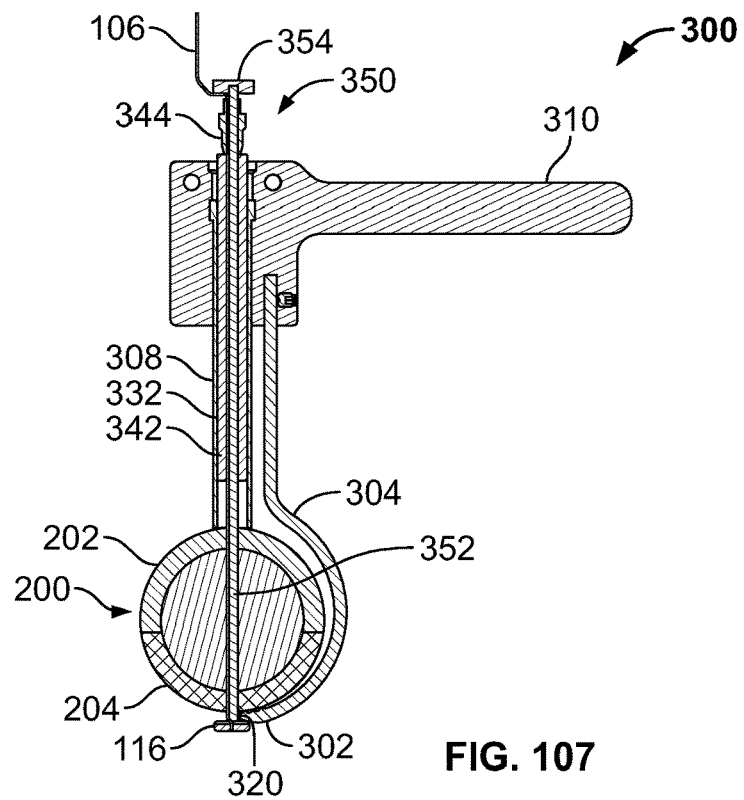
FIG. 107 illustrates a section view of an embodiment of FIG. 102, for example including positioning a fastener and/or elongate member through the tissue fracture with a pushrod.

Then, fastener 116 attached to the elongate member 106 may be positioned (FIG. 107). Drill 346 may be removed by rotating drill 346 to disengage attachment features 344 and 348. Sleeve 342 may be kept in position as the passage therein may be used for inserting fastener 116 and elongate member 106. Fastener 116 and elongate member 106 may be inserted into sleeve 342 and/or pushrod assembly 350 may be configured to advance the fastener 116 and/or elongate member 106 to and/or through the fracture of tissue 200. Shaft 352 of pushrod assembly 350 may be inserted into sleeve 342. Head 354 of the pushrod 350 may be pressed while fastener 116 and elongate member 106 are advanced through sleeve 342 and the fracture of tissue 200 until fastener 116 and elongate member 106 pass out of the sleeve 342 and onto a distal area of tissue 204. After the fastener 106 is deployed, pushrod assembly 350, sleeve 342, and drill guide 330 may be removed.

Figure 108:
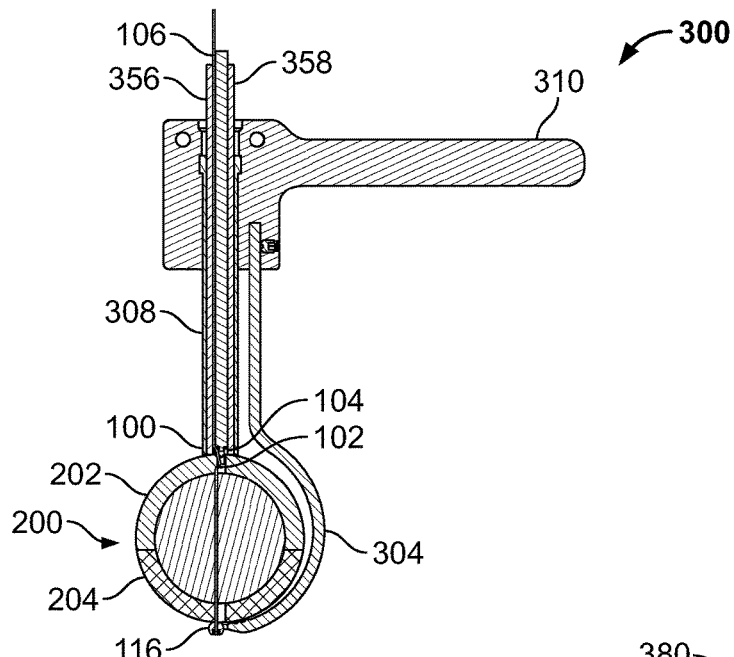
FIG. 108 illustrates a section view of an embodiment of FIG. 102, for example with the fastener positioned at a distal area and the pushrod removed.

Fixation device 100 including base component 102 and insert component 104 may be positioned with respect to elongate member 106. (FIG. 108). Base component 102 may be attached to a holder 356 with an end profile configured to receive base component 102. Elongate member 106 may be positioned through the base 102, holder 356, and base component 102 until elongate member 106 is advanced until elongate member 106 reaches the fracture of tissue 200 and/or tissue 202. Insert component 104 may be pressed or threaded onto a distal portion of insert rod 358 and is advanced through the holder 356 positioned on base component 102. Insert rod 358 may include a channel cut along its side for elongate member 106 to pass. Elongate member 106 may be tensioned to remove slack while base component 102 and insert component 104 are positioned at a proximal area of tissue 202.

Figure 109:
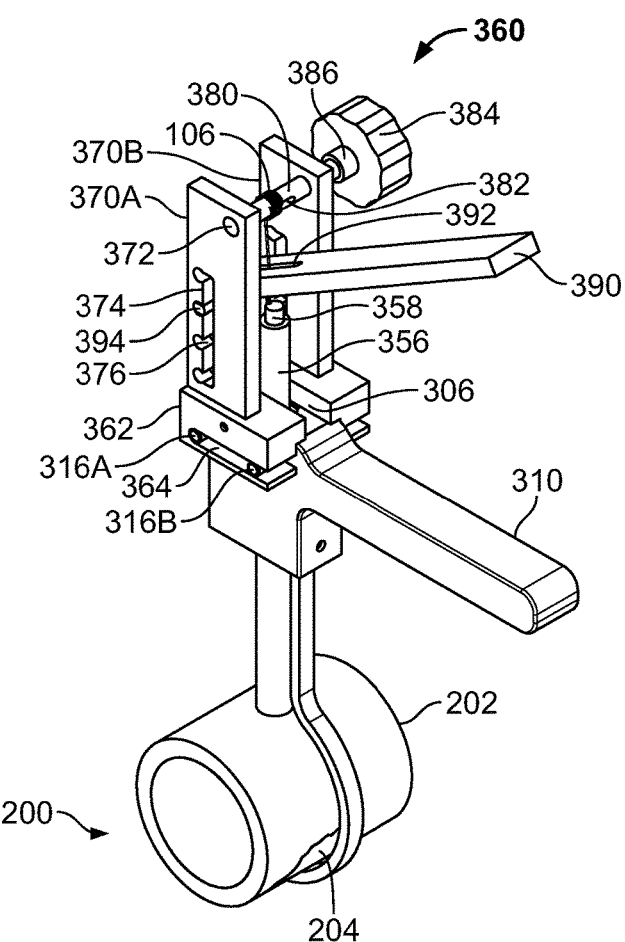
FIG. 109 illustrates an isometric view of an alternative embodiment of FIG. 102, for example, including a device configured to tension the elongate member and press the pushrod.

Clamp 300 may be used in conjunction with instrument 360. (FIG. 109). Instrument 360 may be configured for tensioning and/or deployment of elongate member 106 and/or fastener 116. Instrument 360 may be releasably attachable to clamp 300, for example, by sliding slots 364 of base bracket 362 over posts 316 of handle 310. Instrument 360 may slide onto the handle 310 and around holder 362 and insert rod 358 along top slot 366 of base bracket 362. Instrument 360 may additionally include uprights 370, tensioning rod 380 with knob 384, and press handle 390.

After instrument 360 is positioned and base bracket 362 is secured, press handle 390 may be adjusted to a desired height by rotating press handle 390 so that handle pin 394 may be moved through slots 374 in uprights 370 and into at least one of positioning holes 376. Handle pin 394 may be generally round with flats on two or more sides, for example, to allow it to be moved from positioning hole 376 and into the slot 374 in uprights 370. From slot 374, handle pin 394 may be rotated into alignment with the desired positioning hole 376. Then, handle pin 394 may be passed into the positioning hole 376, thereby locking the position of the press handle 390.

Elongate member 106 which is passed through the holder tube 356 and into a groove in insert rod 358. Insert rod 358 may be passed through the slot 392 in press handle 390 and into slot 382 in tensioning rod 380. After positioning elongate member 106, elongate member 106 may be held in tension until the tensioning rod 380 is rotated by knob 384. As knob 384 is rotated, tension may be applied to elongate member 106 to pull fastener 116 tight to secure tissue 204 of the fracture of tissue 200. Embodiments may include a tensioning mechanism, for example a clutch, ratchet, gear and pawl, spring loaded lock, anti-reversing mechanism, or any other device disclosed herein capable of holding or applying tension. The tensioning mechanism may be integrated into any portion of the device, for example tensioning rod 380, uprights 370, knob 384, and/or knob connection 386. The tensioning mechanism may be configured to apply tension and/or resist a loss of tension in the elongate member 106. The tensioning mechanism may be configured to dial in or pre-set the desired amount of tension for elongate member 106. Embodiments of the present disclosure may include any additional devices and methods disclosed U.S. Patent Application Publication Nos. 2006/0229623, titled "Tissue Fixation System and Method", 2008/0195145, titled "Tissue Fixation System and Method", and 2007/0088362, titled "Apparatus and Methods for Surgery", which are hereby incorporated by reference in their entirety.

After elongate member 106 is tensioned to reduce the fracture, press handle 390 may be squeezed and rotated toward the handle 310. This motion may drive insert rod 358 toward tissue 200, thereby pressing insert component 104 into the base component 102 and/or securing elongate member 106. After the press handle 390 is rotated, the pressure on handle 390 may be released, elongate member 106 in the tensioning rod 380 may be unwrapped or cut, and instrument 360 may be removed. After insert component 104 is pressed into the base component 102 with the elongate member 106 captured therein, insert rod 358 and holder tube 356 can be removed, thereby leaving the fixation device 100 on a proximal area of the tissue 202, fastener 116 on a distal area of tissue 204, and elongate member 106 tensioned and secured therebetween.

In addition to the embodiments of FIGS. 102-109, any instrumentation suitable to secure fixation device 100 to the elongate member 106 and/or to secure two or more tissue fragments may be utilized. Any clamping or comparable mechanism may be employed including an in-line handle and drill guide. Also, a variety of instruments configured for tensioning and deployment may attach to clamp 300 or be standalone.

Figure 110:
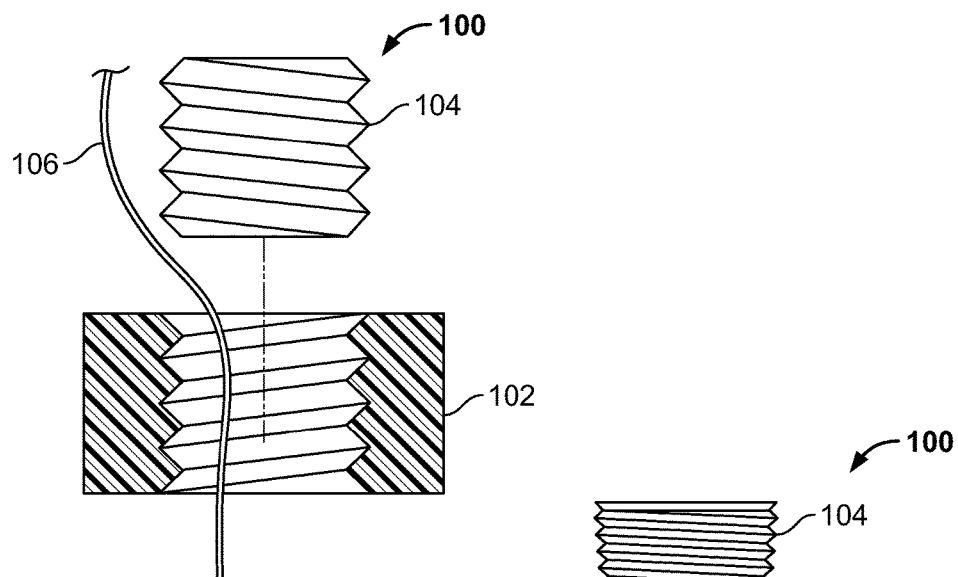
FIG. 110 illustrates a section view of an embodiment, for example, including an alternative fixation device.

As another embodiment, fixation device 100 may include a threaded insert component 104 configured to screw into threaded base component 102 to secure the elongate member 106. (FIG. 110). The threaded interface may be entirely or partially disengaged prior to receiving or tensioning elongate member 106, then may engage when elongate member 106 positioned therebetween. The threads may be rounded, dulled, softened, blunted, or otherwise configured to secure the elongate member 106 while minimizing damage to elongate member 106. Alternatively, the threaded interface may be replaced with any attachment features disclosed herein.

Figure 111:
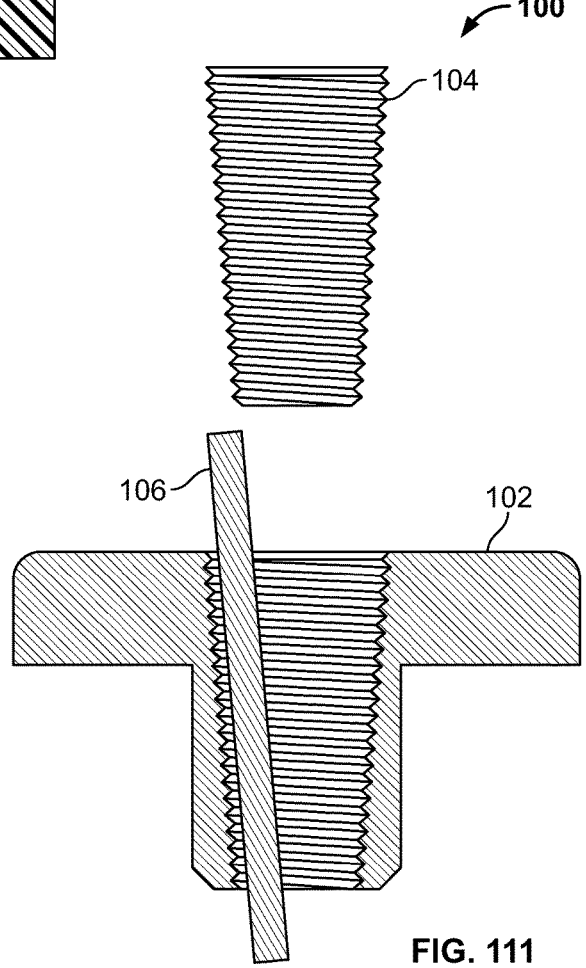
FIG. 111 illustrates a section view of an embodiment, for example, including another alternative fixation device.

Insert 104 may also be threaded at a taper angle that may or may not match a threaded taper of the base component 102. (FIG. 111) The threaded interface may secure elongate member 106. Also, the threads may be configured to act as energy directors to receive energy as an attachment feature, for example including vibratory or thermal energy. Energy may be used to join the base component 102 and insert component 104, for example, to secure the elongate member 106

Figure 112:
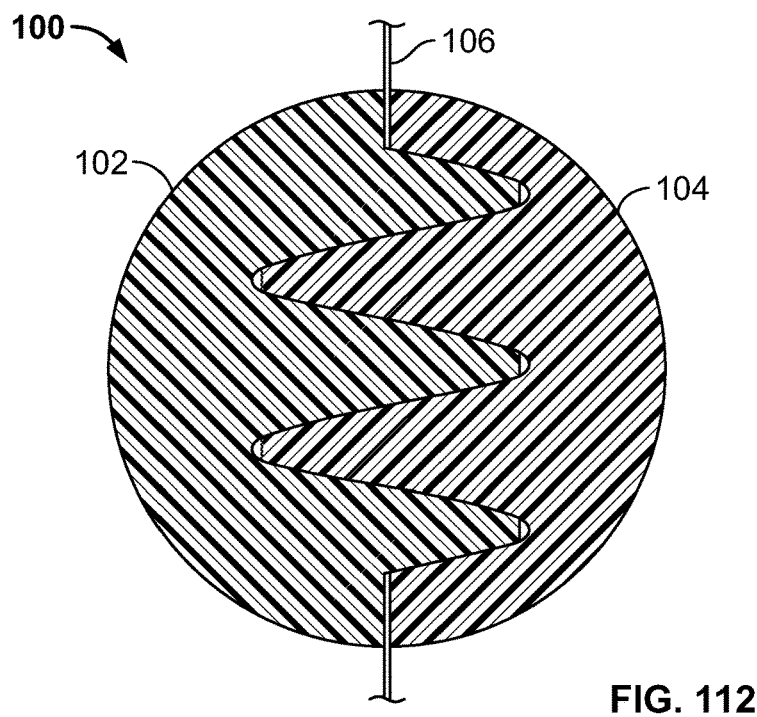
FIG. 112 illustrates a section view of an embodiment, for example, including another alternative fixation device.

Another embodiment of fixation device 100 may include a tortuous path to secure elongate member 106. (FIG. 112). Elongate member 106 may be forced into or clamped between a tortuous path between the projections base component 102 and insert component 104. This may also apply friction to elongate member 106 thereby resisting motion. Fixation device 100 could be secured by mechanical interference of the projections, mechanical interlock, Morse taper, vibratory or thermal joining, or any other attachment feature disclosed herein. Embodiments of the present disclosure may include any additional devices and methods disclosed U.S. Pat. No. 6,475,230, titled "Method and Apparatus for Securing a Suture" and U.S. Pat. No. 8,162,977, titled "Method for joining implants", which are hereby incorporated by reference in their entirety.

Figure 113:
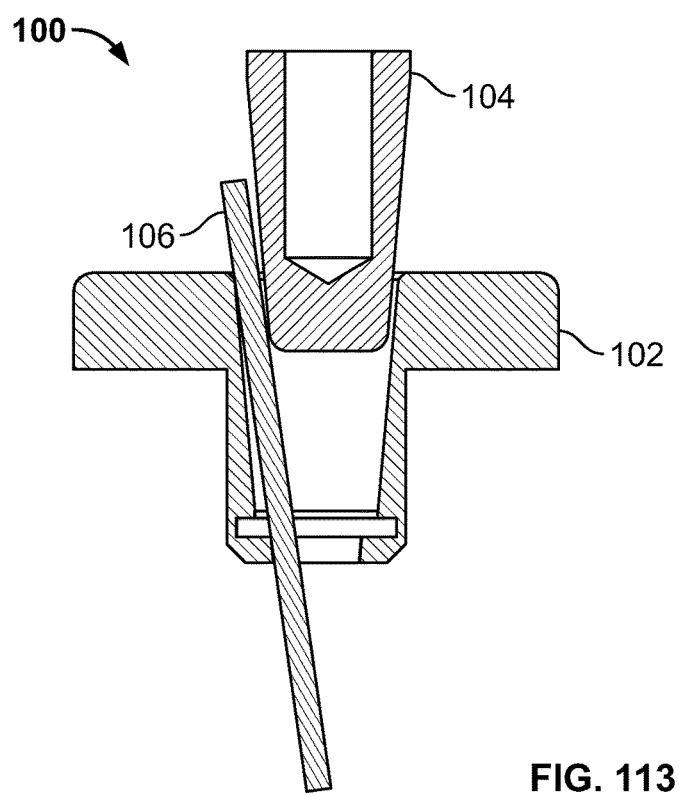
FIG. 113 illustrates a section view of an embodiment, for example, including another alternative fixation device.

Additional embodiments of fixation device 100 may include insert component 104 that may be configured to be driven into the base component 102 with energy, for example vibratory (i.e. ultrasonic) or thermal energy. (FIG. 113). The distal portion of the insert component 104 may be configured to meet the bottom of the undersized and/or tapered bore of the base 102. Insert 104 may be configured to shorten, widen, melt, and/or flow, for example, into the undercut cavities in the base component 102. The melted material may then solidify in the undercut thereby securing insert component 102 to base component 104 while locking the elongate member 106 between the walls of the components.

Embodiments may use energy to bond, assemble, secure, and/or position fixation devices and/or implants. Energy may be applied preoperatively, intraoperatively, or postoperatively. For example, vibratory energy (i.e. ultrasonic energy) may be utilized to bond fixation devices and/or implants (i.e. joint replacements) with respect to a portion of the body. Vibratory energy may be utilized to bond one or more components of the embodiments herein with respect to each other. Embodiments of the present disclosure may include any additional devices and methods disclosed in any of U.S. Pat. No. 7,967,820, titled "Methods and Devices for Trauma Welding" and U.S. Pat. No. 8,162,977, titled "Methods for Joining Implants", U.S. Patent Application Publication Nos. 2009/0024161, titled "Methods and Devices for Intracorporeal Bonding of Implants with Thermal Energy", 2010/0211120, titled "Methods and Devices for Utilizing Bondable Materials", 2012/0316472, titled "Ultrasonic Handpiece", 2012/0316473, titled "Methods and Systems for Controlling an Ultrasonic Handpiece based on a Sensed Pressure", 2012/0316474, "Methods and Systems for Controlling an Ultrasonic Handpiece based on Tuning Signals", and U.S. patent application Ser. No. 13/789,658, titled "Vibratory Energy Systems and Methods for Occluded Body Cavities", all of which are hereby incorporated by reference in their entirety.

Figure 114:
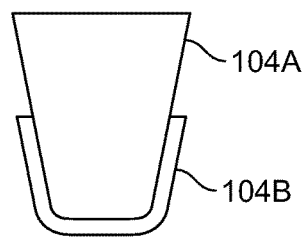
FIG. 114 illustrates a side view of an embodiment, for example, including an alternative insert component in a contracted configuration.
Figure 115:
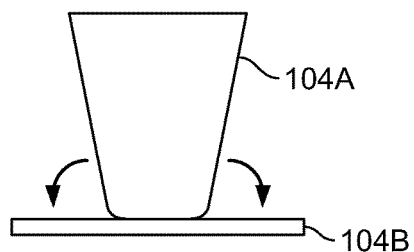
FIG. 115 illustrates a side view of an embodiment of FIG. 114, for example, including an expanded configuration.

Embodiments may include with a shape memory material. (FIGS. 114-115). For example, leading portion 104B of insert component 104 may include a shape memory portion. Insert component 104 may be pressed into a base component 102. After leading portion 104B is positioned in the passage of base component 102, the shape memory material of leading portion 104B may be activated by force or a change in temperature. Leading portion 104B may expand and/or prevent loosening and/or withdraw of the insert component 104 from base component 102, for example, secure elongate member 106.

Figure 116:
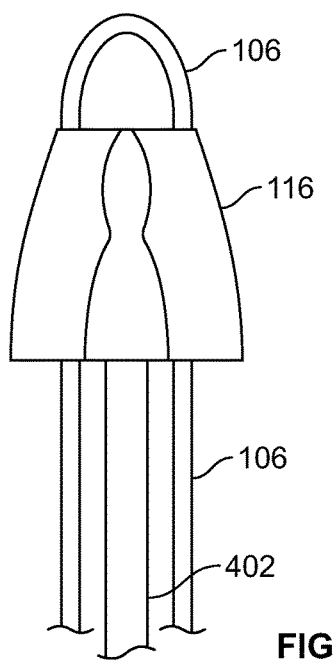
FIG. 116 illustrates a side view of an alternative embodiment, for example, including an alternative fastener positionable with an introducer.
Figure 117:
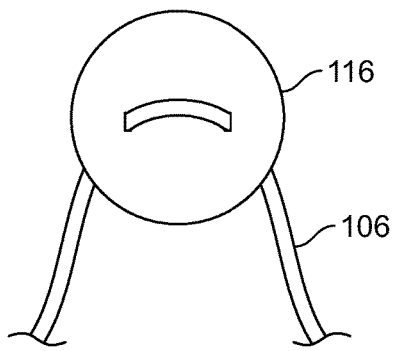
FIG. 117 illustrates an alternative embodiment of FIG. 116, for example, including an alternative fastener.
Figure 118:
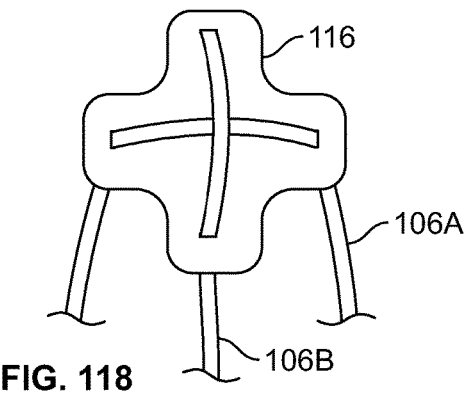
FIG. 118 illustrates an alternative embodiment of FIG. 116, for example, including another alternative fastener.

Further embodiments may include deformable materials or configurations. (FIGS. 116-118) Fastener 116 may be deformable. Fastener 116 connected to elongate member 106 may be passed through and/or positioned with introducer 402. (FIG. 116). Fastener 116 may include a circular or round shape with one or more elongate member 106 positioned through fastener 116. (FIG. 117). Fastener 116 may be in the shape of a cross or plus sign with tabs. (FIG. 118) The tabs may facilitate folding of fastener 116 into inserter 402. Also, the tabs may be configured to receive two or more elongate members 106.

Figure 119:
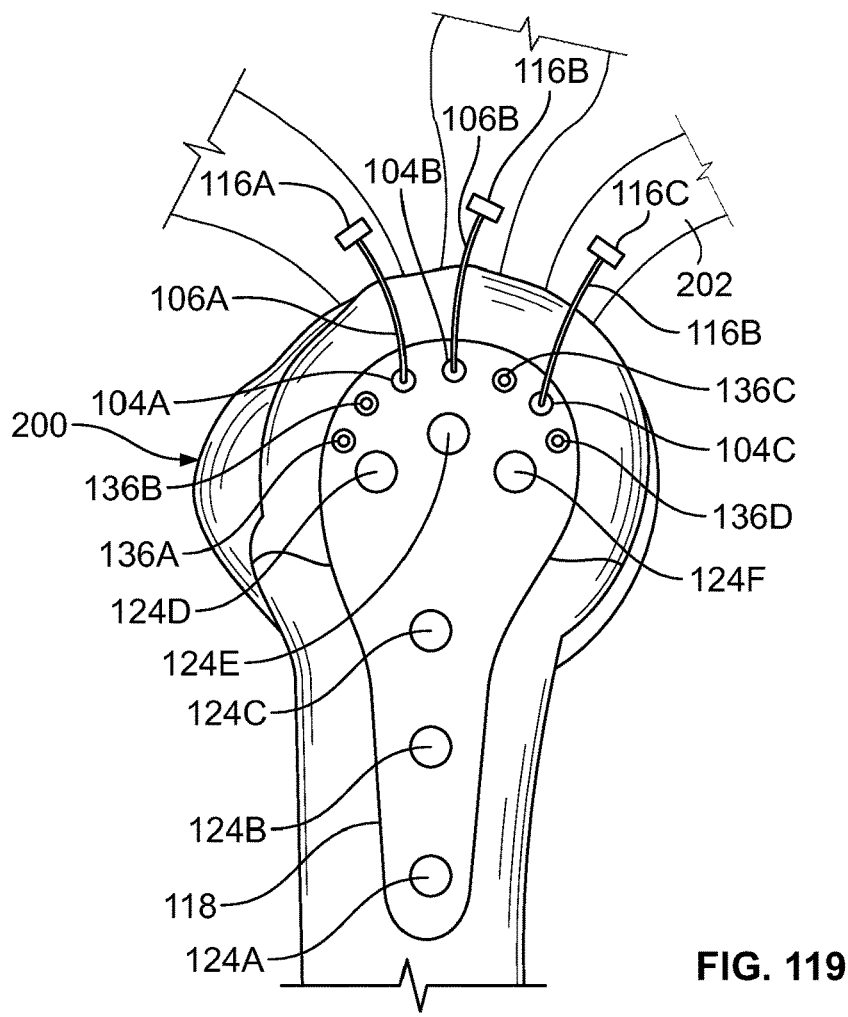
FIG. 119 illustrates an isometric view of an embodiment of FIG. 57.
Figure 120:
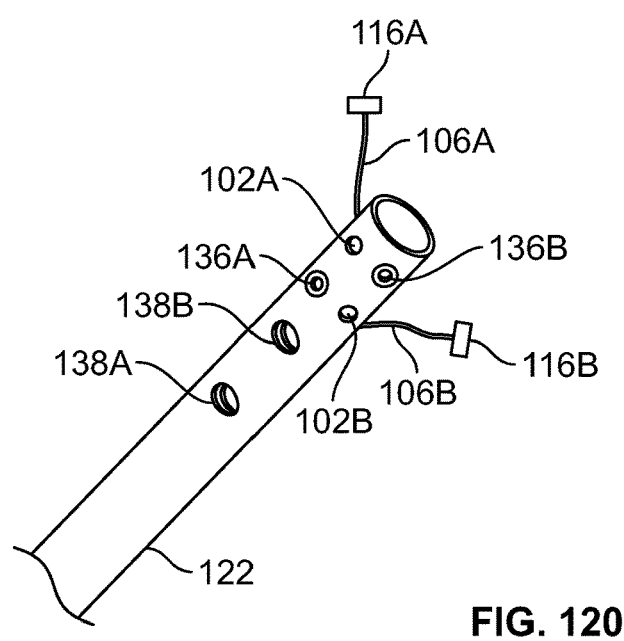
Figure 121:
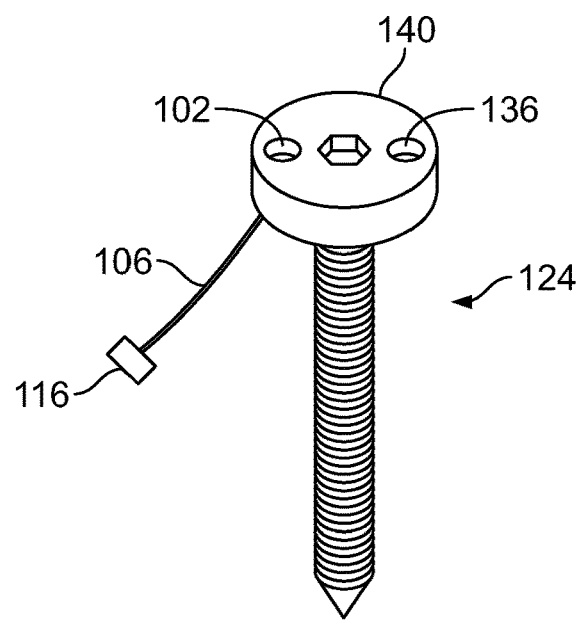

Additional embodiments may be utilized with implants, for example plates and/or screws. (FIGS. 119-121). Embodiments may be used in conjunction with a proximal humerus fracture plate similar to that shown previously in FIG. 57. Plate 118 may be secured to tissue 200 (i.e. bone) with screws 124. Smaller holes 136 may be located on or near a peripheral portion of plate 118, for example, to receive fasteners 116 attached to elongate members 106. Fasteners 116 may be used to secure tissue 200, for example a rotator cuff. Elongate members 106 may secure tissue 200 by passing through or around tissue 200, for example a humeral head. Elongate members 106 may be secured to plate 118 by insert components 104, for example, by being pressed into holes 136 of plate 118. Holes 136 may be configured to be smaller than holes for traditional screws, for example, to decrease stress concentrations. Also, holes 136 may be located in a peripheral area of plate 118, for example, to be near tissue 200 that requires fixation and to be a distance from the larger screw holes. Also, holes 136 may include a counterbore, for example, to allow for a smaller bore to receive fastener 116 and elongate member 106 while the larger bore configured to receive fixation device 100 or insert component 104 alone. Fixation device 100 or insert component 104 may be pressed into and/or flush with respect to plate 118. Additionally, fixation device 100 or base component 102 can be incorporated into the plate with the counter bore section being threaded for attachment of base component 100 or insert component 104. Hole 136 may also be tapered through all or a portion of its length as an attachment feature for interlocking with the insert 104.

All or any portion of implant 122 may include attachment features. (FIG. 120). Implant 122 may include an intramedullary rod or nail, for example, to provide internal bone fixation. Implant 122 may include holes 138, which may be threaded or include any attachment feature disclosed herein. Implant 122 may also include holes 136 near an end of implant 122 or near a peripheral area of implant 122. One, two, or more holes 138 may be configured to receive fixation device 100 or insert component 102, for example, to secure elongate members 106 connected to fasteners 116. Fasteners 116 may be used for securing tissue fragments that may not be fixated by the traditional intramedullary rods or nails and screws alone.

Implants may include screw 124. Screw 124 may include holes 136 configured to receive fastener 116, elongate member 106, fixation device 100, and/or insert component 104. (FIG. 121) Screw 124 may include head 140 with holes 136 around a peripheral area. Embodiments may include any number of holes 136, for example one, two, three, four, or more holes.

Figure 122:
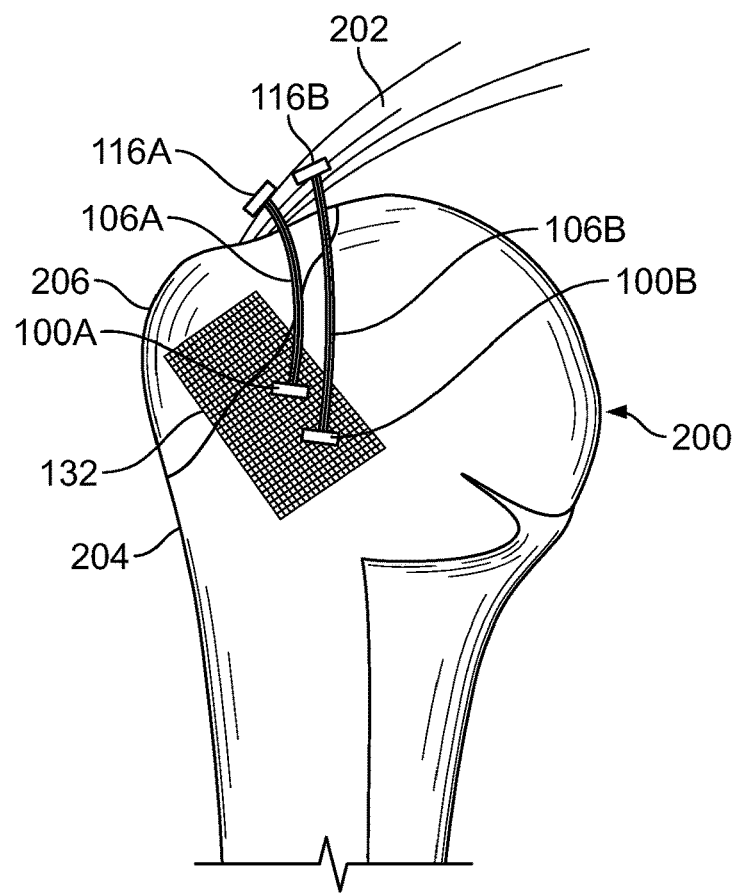

Embodiments may include scaffold or mesh 132. (FIG. 122). Scaffold 132 may include any scaffold or mesh disclosed herein. Scaffold 132 may be incorporated into repair of any portion of the body, for example repair of a humeral head fracture. Scaffold 132 may be configured to promote tissue growth and/or may be secured to the humeral head with fixation devices 100 and/or fasteners 116 connected to elongate members 106. Fasteners 116 and elongate members 106 may be passed through or over tissue 204, 206, and/or 202 (i.e. rotator cuff). This device may secure both soft tissue (i.e. rotator cuff) and hard tissue (i.e. bone). Elongate members 106 pass through the passages created in the humeral head for positioning of the fasteners 116. On the entry side of the passages, fixation devices 100 may secure elongate members 106 and scaffold 132. Scaffold 132 and elongate members 106 may be formed to contour to the tissue surfaces or shrink for improved fixation, for example upon application of energy such as thermal or vibratory energy.

In addition, embodiments may be configured for vascular anastomotic repair. Two tissue segments may be reattached to each other, for example over bone or using a scalpel or balloon. Tissue segments may include tubular, vessel, or anastomotic segments. For example, if an expandable device (i.e. an inflatable device such as a balloon) is positioned to hold the two anastomotic segments in apposition while maintaining the inner diameter, a curved introducer (i.e. awl) may place fastener 116 in a curved section across one vessel segment pulling it around the expandable device or around the scalpel in a curved path back to the second vessel segment, thereby allowing this procedure to tighten and maintain the internal dimension while the expandable device and scalpel are in position. The expandable device (i.e. balloon) may be deflated and the scalpel removed, for example, so the repair occurs around this. Embodiments may be reinforced or sealed with glue adhesive, biofilm adhesive, type adhesive, or any other method disclosed herein. The expandable device and scalpel may maintain the internal dimensions while the outer repair is performed. Embodiments herein may be used in conjunction with the devices and methods disclosed in U.S. Pat. No. 7,497,864, title "Tissue fastener and methods for using same", which is hereby incorporated by reference in its entirety.

Embodiments may be configured for guidance and/or positioning with energy, for example magnetic energy. Embodiments may include a magnet, electromagnet, and/or magnetizable materials, for example, to position the embodiments herein with a magnetic field. Magnetizable materials include ferrite particles, which may or may not be magnetized. The electromagnet may selectively provide a magnetic field with application of current. The magnetic field may emanate from any portion of the embodiments herein. The magnet, electromagnet, and/or magnetizable materials may be mounted on or included in all or any portion of the embodiments herein. A leading end portion may be utilized to position and/or guide the system. The magnetic field may emanate from a portion of the system or from an external source positioned outside the body. The polarity and/or strength of the magnetic field may be increased, decreased, or alternated to controllably guide the system, for example effector 110. Embodiments of the present disclosure may also include any devices and methods disclosed in U.S. Pat. No. 7,320,319, titled "Medicant Delivery System and Method", U.S. Patent Application Publication No. 2008/0306324, titled "Magnetic Joint Implant", and U.S. Pat. No. 6,719,765, titled "Magnetic Suturing System and Method", which are hereby incorporated by reference in their entirety Further embodiments may include a robotic system. The robotic system may position fixation devices, for example, by driving them with navigation or imaging devices (i.e. arthroscopic visualization). The robotic system may be configured for repair of tissue fragments. Embodiments may include a robotic arm. The robotic arm may include a robotic mechanism. Embodiments may be configured to position and/or guide any portion of the system. The robotic arm may include a haptic arm. The robotic arm may be automatic, programmed, user controlled, and/or remote controlled. The motion path of the robotic arm may include end points or boundaries, for example, to minimize user error. Embodiments of the present disclosure may also include any devices and methods disclosed in U.S. Patent Application Publication Nos. 2003/0181800, titled "Methods of Securing Body Tissue", and 2012/0221017, titled "Methods for Robotic Arthroplasty", which are hereby incorporated by reference in their entirety.

Embodiments may also be positioned with an imaging or guidance device. Imaging devices may be used to directly or indirectly visualize, guide and/or change the orientation or position of embodiments herein. Examples of imaging devices may include endoscopic guidance, computer assisted navigation, magnetic resonance imaging (MRI), CT scan, ultrasound, fluoroscopic, cystoscopy, endoscopic retrograde cholangiopancreatography cystoscopy (ERCP), X-ray, light detectors, metal detectors, magnetic field detectors, electromagnetic devices, or other visualization device disclosed herein. Asymmetric coating, radiopaque markers, or other features identifiable with indirect visualization may be used to identify and/or adjust orientation or position. Indirect visualization may also be used to align portions of a first device relative to a portion of the first device, a second device, or a body portion.

Additional embodiments may be configured to secure and/or stabilize the spine. For example, embodiments may be configured to repair an intervertebral disc herniation. Fixation devices 100, fastener 116, and/or elongate member 106 may be configured to move the disk herniation and repair the annulus. Elongate member 106 may be configured to secure two or more fasteners, rods, or plates relative to each other. Embodiments may be configured to repair soft tissues (i.e. ligaments) to hard tissues (i.e. bone) or be used in conjunction with any other tissues or implants disclosed herein. Embodiments of the present disclosure may include any additional devices and methods disclosed U.S. Patent Application Publication No. 2006/0089646, titled "Devices and Methods for Stabilizing Tissue and Implants", which is hereby incorporated by reference in its entirety.

Any embodiment herein may be secured using any of the features or methods disclosed herein. For example, base component 102 and insert component 104 may be secured with any internal and/or external attachment features or methods disclosed herein or known in the art. As another example, fixation devices may be integrated into a portion of a plate, independent of a plate, a portion of an implant, screw, or rod. Embodiments may be secured preoperatively, intraoperatively, or postoperatively. Embodiments may be secured with ultrasonic energy, thermal energy, radiofrequency energy, expandable or hydrophilic materials, chemical, electrical, pressure, press-fit, tapered surfaces, threaded surfaces, mechanical or non-mechanical interlocks, or any other attachment feature disclosed herein. Two or more components may be secured with an expandable ring configured to lock two or more components together.

Embodiments may have any material disclosed herein. Embodiments may be all or partially biodegradable. Embodiments may be configured with a portion being a more rigid polymer and another portion being a less rigid polymer. Any portions may be configured to adhere or stick together to resist movement of elongate member 106 (i.e. suture). Embodiments may be configured to allow elongate member 106 to slide when pulled in one direction while resisting motion or disengage elongate member 106 by pulling in the opposite direction. Embodiments may be configured with two components of a similar material but with a different modulus of elasticity, for example to secure elongate member 106 when urged together and to allow elongate member 106 to move when pulled in a first direction but not in a second direction.

One, two or more elongate members 106 may be positioned through an implant, for example a plate, screw, rod, or arthroplasty component. Embodiments may include an angled or flexible configuration. Embodiments may include a curved, smooth, or tapered edge, for example to facilitate introduction and/or minimize soft tissue damage. Embodiments may be introduced in a linear configuration and/or positioned in a non-linear or bent configuration. The implant may have attachment features (i.e. holes) specifically sized and configured for fixation devices. The attachment feature may be recessed and/or adjacent to a plate or rod so the system may be used with traditional screws. To receive a fixation device or elongate member, the attachment feature may be smaller than holes required for traditional screws. This may preserve the mechanical integrity of a plate, screw, or rod, provide improved fixation, and/or allow for fixation to and/or from varying, curved, or nonlinear paths with respect to plates, screw, rods, or other implants. Embodiments may be used to fasten an implant to hard tissue (i.e. bone) or soft tissue to an implant, for example if a ligament is pulled away from a hip or knee implant. As another example, embodiments may be used for reattachment of greater trochanteric tendons. In addition, embodiments of the present disclosure may include all or any portion of the embodiments disclosed in U.S. Pat. No. 7,837,736, titled "Minimally Invasive Surgical Systems and Methods", which is incorporated herein by reference in its entirety.

All or any portion of any embodiment herein may include any combination of the embodiments disclosed herein. This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A fixation system for securing first and second body tissue portions of a fracture, the system comprising:
    a base component having an aperture, a head portion, and a body portion, wherein the head portion extends at least partially beyond the body portion and is configured to be positioned on an outer surface of the first body tissue, and wherein the body portion has an entirely unthreaded exterior surface and is configured to be positioned in a passage extending through the first and second body tissue portions, and wherein the aperture through the base component has an at least partially tapered inner wall;
    an insert component positionable within at least a portion of the aperture in the base component, and having an at least partially tapered outer surface;
    an elongate member configured to be positioned through the passage extending through the first and second body tissue portions and the aperture of the base component, wherein the elongate member is at least one of a suture, wire, and cable; and
    an anchor configured to couple to the elongate member, the anchor configured to be positioned through the passage extending through the first and second body tissue portions, and the anchor configured to be positioned on the distal outer surface of the second body tissue,
    wherein the slidably positioned elongate member is substantially maintained against the insert component when the at least partially tapered portion of the insert component is pressed against the at least partially tapered inner wall of the aperture through the base component, deforming a portion of at least one of the base component, insert component, and elongate member to secure the first and second body tissue portions, and wherein the elongate member does not contact with at least one of an internal threaded surface of the body portion of the base component and an external threaded surface of the insert component.

2. The system of claim 1, wherein the base and insert components are pressed together to secure the elongate member.

3. The system of claim 1, wherein an interior bore of the base component and an exterior surface of the insert component are joined together by mating tapered surfaces.

4. The system of claim 1, wherein an interior taper of the base component is configured to match an exterior taper of the insert component to lock the elongate member.

5. The system of claim 1, wherein a taper is disposed between the base component and insert component to promote locking of the elongate member while it is tensioned through the passage and the insert component is pulled into the base component.

6. The system of claim 1, wherein the base component has a cylindrical portion dimensioned to a drilled hole in a proximal bone portion.

7. The system of claim 6, wherein the cylindrical portion provides additional contact length for locking the elongate member.

8. The system of claim 6, wherein the cylindrical portion is configured to minimize the height protruding above a surface of the bone portion.

9. The system of claim 6, wherein the cylindrical portion is configured to stabilize the base and insert components by maintaining a position relative to the hole in body tissue.

10. The system of claim 1, wherein the head portion of the base component includes at least one tab configured to conform to a proximal bone surface and resist the base component from being pulled into a drilled hole on the proximal bone surface.

11. The system of claim 10, wherein the head portion of the base component includes two, three, or more tabs.

12. The system of claim 10, wherein the tab surrounds the perimeter of the head portion of the base component.

13. The system of claim 1, wherein the base component includes a smooth and tapered interior surface.

14. The system of claim 1, wherein the base component includes a tapered distal portion and a threaded proximal interior portion configured to mate with the insert component.

15. The system of claim 1, wherein the insert component includes a passage configured to receive the elongate member and a distal portion configured to pinch the elongate member against the base component.

16. The system of claim 1, wherein the insert component includes threads on a proximal exterior portion for mating with threads in the base component.

17. The system of claim 1, wherein the insert component includes a square, star, or hex shaped recess for screwing the insert component into the base component.

18. The system of claim 1, wherein the insert component includes a recess configured to receive a removal tool for un-screwing the insert component from the base component.

19. The system of claim 1, wherein the insert component includes two or more finger members around a passage through the insert component that are configured to collapse and lock against the elongate member when the insert component is pressed into the base component.

20. The system of claim 1, wherein the insert component includes a tapered exterior configured to press and lock the elongate member between an exterior surface of the insert component and an interior surface of the base component.

21. The system of claim 1, wherein the insert component includes a drilled or tapped passage into a portion of a length of the insert component, the passage being configured to receive a threaded instrument.

22. The system of claim 1, wherein the insert component is configured to be removed from the base component by screwing a threaded tip tool into a passage in the insert component until the tool locks or bottoms in the insert component.

23. The system of claim 22, wherein the insert component is configured to be loosened by rotation of the tool and removed by pulling the tool.

24. The system of claim 1, further comprising a plate or rod.

25. The system of claim 24, wherein the plate or rod includes holes to receive a cannulated drill for making a passage through the fracture.

26. The system of claim 25, wherein the cannulated drill is configured to pass a fastener and elongate member through a cannulated portion of the cannulated drill.

27. The system of claim 24, wherein the plate or rod includes tapered holes configured to allow locking of the elongate member independent of the base component.

28. The system of claim 24, wherein the plate or rod includes holes or cavities.

29. The system of claim 1, wherein the base or insert component includes a metallic, polymer, or resorbable material.

30. The system of claim 29, wherein the metallic material includes stainless steel or titanium.

31. The system of claim 29, wherein the polymer material includes PEEK (polyetheretherketone).

32. The system of claim 1, wherein the base component and insert component are different materials.

33. The system of claim 1, wherein the elongate member includes a metallic material.

34. The system of claim 1, wherein the base component includes metal and the insert component includes PEEK.

* * * * *